United States Patent
Chen

(10) Patent No.: US 10,126,227 B2
(45) Date of Patent: Nov. 13, 2018

(54) FLOW CYTOMETER

(71) Applicant: IRIS INTERNATIONAL, INC., Chatsworth, CA (US)

(72) Inventor: Yong Qin Chen, San Jose, CA (US)

(73) Assignee: IRIS INTERNATIONAL, INC., Chatsworth, CA (US)

( * ) Notice: Subject to any disclaimer, the term of this patent is extended or adjusted under 35 U.S.C. 154(b) by 0 days.

(21) Appl. No.: 15/639,601

(22) Filed: Jun. 30, 2017

(65) Prior Publication Data

US 2018/0059001 A1  Mar. 1, 2018

Related U.S. Application Data

(60) Division of application No. 14/555,102, filed on Nov. 26, 2014, now Pat. No. 9,746,412, which is a (Continued)

(51) Int. Cl.
*G01N 15/14* (2006.01)
*G02B 6/26* (2006.01)
(Continued)

(52) U.S. Cl.
CPC ..... *G01N 15/1436* (2013.01); *G01N 15/1434* (2013.01); *G01N 15/1459* (2013.01);
(Continued)

(58) Field of Classification Search
CPC ........... G01N 15/1436; G01N 15/1459; G01N 15/1434; G02B 27/0025; G02B 21/361; G02B 21/04; G02B 6/26
See application file for complete search history.

(56) References Cited

U.S. PATENT DOCUMENTS 2,385,495 A   9/1945   Brian .................. 250/487.1
2,669,709 A   2/1954   Glancy et al. ............ 348/784
(Continued)

FOREIGN PATENT DOCUMENTS

CN   102087198    6/2011
CN   201917509 U  8/2011
(Continued)

OTHER PUBLICATIONS

Brogioli et al., "Heterodyne near-field scattering," *Applied Physics Letters* 81(22):4109-4111, 2002.
(Continued)

*Primary Examiner* — David Porta
*Assistant Examiner* — Mindy Vu
(74) *Attorney, Agent, or Firm* — Norton Rose Fulbright US LLP

(57) ABSTRACT

The disclosed flow cytometer includes a wavelength division multiplexer (WDM). The WDM includes an extended light source providing light that forms an object, a collimating optical element that captures light from the extended light source and projects a magnified image of the object as a first light beam, and a first focusing optical element configured to focus the first light beam to a size smaller than the object of the extended light source to a first semiconductor detector. The disclosed flow cytometer further includes a composite microscope objective to direct light emitted by a particle in a flow channel in a viewing zone of the composite microscope to the extended light source, a fluidic system and a peristaltic pump configured to supply liquid sheath and liquid sample to the flow channel, and a laser diode system to illuminate the particle in the flow channel.

20 Claims, 35 Drawing Sheets

Related U.S. Application Data continuation-in-part of application No. PCT/US2013/043453, filed on May 30, 2013.

(60) Provisional application No. 61/911,859, filed on Dec. 4, 2013, provisional application No. 61/653,245, filed on May 30, 2012, provisional application No. 61/653,328, filed on May 30, 2012, provisional application No. 61/715,819, filed on Oct. 18, 2012, provisional application No. 61/715,836, filed on Oct. 19, 2012, provisional application No. 61/816,819, filed on Apr. 29, 2013.

(51) Int. Cl.

| | | |
|---|---|---|
| *G02B 6/293* | (2006.01) | |
| *G02B 21/04* | (2006.01) | |
| *G02B 21/36* | (2006.01) | |
| *G02B 27/00* | (2006.01) | |
| *G01N 15/10* | (2006.01) | |

(52) U.S. Cl.
CPC ............ *G02B 6/26* (2013.01); *G02B 6/29365* (2013.01); *G02B 21/04* (2013.01); *G02B 21/361* (2013.01); *G02B 27/0025* (2013.01); *G01N 2015/1006* (2013.01); *G01N 2015/144* (2013.01); *G01N 2015/1452* (2013.01)

(56) References Cited

U.S. PATENT DOCUMENTS

| | | | |
|---|---|---|---|
| 2,764,147 A | 9/1956 | Bnumer | 126/247 |
| 3,199,341 A | 8/1965 | Heuer, Jr. et al. | 73/807 |
| 3,411,293 A | 11/1968 | Akins | 60/454 |
| 3,542,491 A | 11/1970 | Newman | 417/295 |
| 3,661,460 A | 5/1972 | Elking et al. | 356/36 |
| 3,726,613 A | 4/1973 | von Casimir | 417/477.1 |
| 3,826,593 A | 7/1974 | von Casimir | 417/53 |
| 3,873,204 A | 3/1975 | Friedman et al. | 356/39 |
| 3,946,239 A | 3/1976 | Salzman et al. | 250/461.2 |
| 3,953,727 A | 4/1976 | d'Auria et al. | 398/88 |
| 3,989,381 A | 11/1976 | Fulwyler | 356/39 |
| 4,073,574 A | 2/1978 | Clarke et al. | 359/728 |
| 4,188,543 A | 2/1980 | Brunsting et al. | 250/458.1 |
| 4,189,236 A | 2/1980 | Hogg et al. | 356/317 |
| 4,244,045 A | 1/1981 | Nosu et al. | 398/86 |
| 4,482,994 A | 11/1984 | Ishikawa | 398/86 |
| 315,667 A | 4/1985 | Serdinko | 417/475 |
| 4,515,274 A | 5/1985 | Hollinger et al. | 209/3.1 |
| 4,564,342 A | 1/1986 | Weber et al. | 417/477.6 |
| 4,576,556 A | 3/1986 | Thompson | 417/477.12 |
| 4,623,225 A | 11/1986 | Forkner | 359/669 |
| 4,673,289 A | 6/1987 | Gaucher | 356/72 |
| 4,727,020 A | 2/1988 | Recktenwald | 435/6.11 |
| 4,745,285 A | 5/1988 | Recktenwald et al. | 250/458.1 |
| 4,778,253 A | 10/1988 | Siga et al. | 359/819 |
| 4,834,630 A | 5/1989 | Godwin | 417/475 |
| 4,871,249 A | 10/1989 | Watson | 356/73 |
| 4,920,275 A | 4/1990 | Itoh | 250/574 |
| 4,950,136 A | 8/1990 | Haas et al. | 417/477.7 |
| 4,976,590 A | 12/1990 | Baldwin | 417/53 |
| 4,997,275 A | 3/1991 | Gaucher et al. | 356/72 |
| 5,050,963 A | 9/1991 | Murakami | 359/808 |
| 5,142,462 A | 8/1992 | Kashima | 362/268 |
| 5,157,917 A | 10/1992 | Liang et al. | |
| 5,177,641 A | 1/1993 | Kobayashi et al. | 359/820 |
| 5,230,614 A | 7/1993 | Zanger et al. | 417/477.9 |
| 5,245,318 A | 9/1993 | Tohge et al. | 340/611 |
| 5,251,060 A | 10/1993 | Uenishi et al. | 359/328 |
| 5,257,917 A | 11/1993 | Minarik et al. | 417/475 |
| 5,299,066 A | 3/1994 | Rombult | 359/819 |
| 5,317,162 A | 5/1994 | Pinsky et al. | 250/461.2 |
| 5,369,476 A | 11/1994 | Bowers et al. | 399/49 |
| 5,373,395 A | 12/1994 | Adachi | 359/652 |
| 5,396,487 A | 3/1995 | Abe et al. | 359/819 |
| 5,467,225 A | 11/1995 | Manabe | 359/661 |
| 5,470,211 A | 11/1995 | Knott et al. | 417/477.9 |
| 5,475,210 A | 12/1995 | Taguchi et al. | 250/205 |
| 5,548,395 A | 8/1996 | Kosaka | 356/73 |
| 5,583,683 A | 12/1996 | Scobey | 398/79 |
| 5,615,200 A | 3/1997 | Hoshino et al. | 369/112.04 |
| 5,746,585 A | 5/1998 | McDunn et al. | 417/477.11 |
| 5,748,372 A | 5/1998 | Kitagawa | 359/565 |
| 5,777,674 A | 7/1998 | Ohmuro | 348/338 |
| 5,781,351 A | 7/1998 | Murakami et al. | 359/808 |
| 5,786,915 A | 7/1998 | Scobey | 398/82 |
| 5,788,927 A | 8/1998 | Farrell et al. | 422/63 |
| 5,805,363 A | 9/1998 | Okuda et al. | 359/819 |
| 5,850,292 A | 12/1998 | Braun | 356/419 |
| 5,915,925 A | 6/1999 | North, Jr. | 417/36 |
| 5,971,713 A | 10/1999 | North, Jr. | 417/36 |
| 6,008,920 A | 12/1999 | Hendrix | 398/79 |
| 6,017,194 A | 1/2000 | North, Jr. | 417/36 |
| 6,102,678 A | 8/2000 | Peclat | 417/477.7 |
| 6,135,734 A | 10/2000 | Isozumi et al. | 417/542 |
| 6,159,686 A | 12/2000 | Kardos et al. | 435/6 |
| 6,200,101 B1 | 3/2001 | North, Jr. | 417/36 |
| 6,252,719 B1 | 6/2001 | Eichenbaum | 359/634 |
| 6,315,952 B1 | 11/2001 | Sklar et al. | 422/63 |
| 6,510,007 B1 | 1/2003 | Blasenheim | 359/659 |
| 6,542,306 B2 | 4/2003 | Goodman | 359/634 |
| 6,572,255 B2 | 6/2003 | Husher | 366/132 |
| 6,608,682 B2 | 8/2003 | Ortyn et al. | 356/419 |
| 6,618,143 B2 | 9/2003 | Roche et al. | 356/339 |
| 6,638,481 B2 | 10/2003 | Sklar et al. | 422/63 |
| 6,647,175 B1 | 11/2003 | LoRegio et al. | 385/24 |
| 6,683,314 B2 | 1/2004 | Oostman, Jr. et al. | 250/461.2 |
| 6,713,019 B2 | 3/2004 | Ozasa et al. | 422/82.09 |
| 6,748,133 B2 | 6/2004 | Liu et al. | 385/24 |
| 6,767,188 B2 | 7/2004 | Vrane et al. | 417/40 |
| 6,768,593 B1 | 7/2004 | Jutamulia | 359/641 |
| 6,788,409 B2 | 9/2004 | Goodwin | 356/339 |
| 6,794,671 B2 | 9/2004 | Nicoli et al. | 250/574 |
| 6,813,017 B1 | 11/2004 | Hoffman et al. | 356/317 |
| 6,839,367 B2 | 1/2005 | Nagamatsu et al. | 372/34 |
| 6,870,679 B2 | 3/2005 | Randall et al. | 359/580 |
| 6,870,976 B2 | 3/2005 | Chen et al. | 385/14 |
| 6,897,954 B2 | 5/2005 | Bishop et al. | 356/317 |
| 6,941,047 B2 | 9/2005 | Capewell et al. | 385/47 |
| 6,954,722 B2 | 10/2005 | Parks et al. | 702/194 |
| 6,975,400 B2 | 12/2005 | Ortyn et al. | 356/419 |
| 7,038,778 B2 | 5/2006 | Yamauchi | 356/419 |
| 7,072,540 B1 | 7/2006 | Szapiel et al. | 385/24 |
| 7,110,192 B2 | 9/2006 | Sauter et al. | 359/754 |
| 7,113,266 B1 | 9/2006 | Wells | 356/73 |
| 7,127,356 B2 | 10/2006 | Nicoli et al. | 702/26 |
| 7,129,505 B2 | 10/2006 | Oostman, Jr. et al. | 250/458.1 |
| 7,212,343 B1 | 5/2007 | He et al. | 359/618 |
| 7,260,328 B2 | 8/2007 | Kropp | 398/82 |
| 7,262,838 B2 | 8/2007 | Fritz | 356/73 |
| 7,268,953 B2 | 9/2007 | Matthae et al. | 359/656 |
| 7,305,018 B2 | 12/2007 | Otoma | 372/50.1 |
| 7,381,565 B2 | 6/2008 | Kurabayashi et al. | 436/63 |
| 7,385,682 B2 | 6/2008 | Chu et al. | 356/73 |
| 7,430,048 B2 | 9/2008 | Reel et al. | 356/432 |
| 7,450,229 B2 | 11/2008 | Ortyn et al. | 356/326 |
| 7,453,915 B2 | 11/2008 | Imai | 372/50.1 |
| 7,456,960 B2 | 11/2008 | Cemi et al. | 356/336 |
| 7,496,463 B2 | 2/2009 | Nicoli et al. | 702/104 |
| 7,505,131 B2 | 3/2009 | Roth | 356/317 |
| 7,507,588 B2 | 3/2009 | Mehrpouyan et al. | 436/518 |
| 7,561,267 B2 | 7/2009 | Luo et al. | 356/336 |
| 7,580,120 B2 | 8/2009 | Hamada et al. | 356/73 |
| 7,623,243 B2 | 11/2009 | Kato | 356/419 |
| 7,630,147 B1 | 12/2009 | Kar et al. | 359/716 |
| 7,645,127 B2 | 1/2010 | Hagen et al. | 417/477.12 |
| 7,668,422 B2 | 2/2010 | Kropp | 385/47 |
| 7,758,324 B2 | 6/2010 | Baumann et al. | 417/477.2 |
| 7,768,120 B2 | 8/2010 | Takashima | 257/706 |
| 7,781,227 B2 | 8/2010 | Mehrpouyan et al. | 436/523 |
| 7,787,197 B2 | 8/2010 | Chen | 359/793 |
| 7,835,000 B2 | 11/2010 | Graves et al. | 356/338 |
| 7,876,436 B2 | 1/2011 | Chu | 356/338 |

(56) References Cited

U.S. PATENT DOCUMENTS

| | | |
|---|---|---|
| 7,889,263 B2 | 2/2011 | Ortyn et al. ............... 348/335 |
| 7,894,047 B2 | 2/2011 | Hamada et al. ............ 356/39 |
| 7,952,981 B2 | 3/2011 | Suzuki ....................... 369/121 |
| 7,981,661 B2 | 7/2011 | Rich ........................... 435/286.5 |
| 8,009,189 B2 | 8/2011 | Ortyn et al. ............... 348/80 |
| 8,049,185 B2 | 11/2011 | Hayashi et al. ............ 250/459.1 |
| 8,149,525 B2 | 4/2012 | Do .............................. 359/797 |
| 8,157,547 B2 | 4/2012 | Vrielink ..................... 417/477.3 |
| 8,187,888 B2 | 5/2012 | Rich ........................... 436/63 |
| 8,213,472 B2 | 7/2012 | Hirai et al. ................. 372/36 |
| 8,229,707 B2 | 7/2012 | Olson et al. ............... 702/189 |
| 8,233,146 B2 | 7/2012 | Chen .......................... 356/246 |
| 8,253,938 B2 | 8/2012 | Vacca et al. ................ 356/337 |
| 8,270,098 B2 | 9/2012 | Fukuta et al. .............. 359/784 |
| 8,284,402 B2 | 10/2012 | Frazier et al. .............. 356/419 |
| 8,337,096 B2 | 12/2012 | Shen et al. ................. 385/89 |
| 8,345,237 B2 | 1/2013 | Tsukii et al. ............... 356/338 |
| 8,405,048 B2 | 3/2013 | Hayashi ..................... 250/458.1 |
| 8,432,541 B2 | 4/2013 | Rich ........................... 356/246 |
| 8,436,371 B2 | 5/2013 | Medendorp, Jr. et al. ..... 257/88 |
| 8,436,993 B2 | 5/2013 | Kaduchak et al. ......... 356/337 |
| 8,488,244 B1 | 7/2013 | Li et al. ..................... 359/618 |
| 8,507,279 B2 | 8/2013 | Ball et al. .................. 436/10 |
| 2002/0067895 A1 | 6/2002 | Flanders .................... 385/88 |
| 2002/0141902 A1 | 10/2002 | Ozasa et al. ............... 422/82.09 |
| 2003/0142720 A1 | 7/2003 | Bradburn et al. .......... 372/108 |
| 2004/0033010 A1* | 2/2004 | McGuire, Jr. .......... G02B 6/272 385/16 |
| 2004/0165828 A1 | 8/2004 | Capewell et al. .......... 385/47 |
| 2004/0218184 A1 | 11/2004 | Jorgenson et al. ......... 356/419 |
| 2005/0084402 A1 | 4/2005 | Vanek ........................ 417/477.3 |
| 2005/0134836 A1 | 6/2005 | Paldus et al. .............. 356/73 |
| 2006/0221325 A1 | 10/2006 | Wells ......................... 356/73 |
| 2006/0245964 A1 | 11/2006 | Koslov ....................... 417/477.1 |
| 2006/0256335 A1 | 11/2006 | Chen .......................... 356/369 |
| 2006/0292021 A1 | 12/2006 | Tu .............................. 417/477.1 |
| 2007/0124947 A1 | 6/2007 | Munroe et al. ............. 33/286 |
| 2008/0024758 A1 | 1/2008 | Tabata ........................ 356/39 |
| 2008/0241911 A1 | 10/2008 | Ueno et al. ................. 435/287.1 |
| 2009/0091746 A1 | 4/2009 | Fukuda et al. ............. 356/73 |
| 2009/0190128 A1 | 7/2009 | Cerni et al. ................ 356/336 |
| 2010/0067079 A1* | 3/2010 | Rathjen .................. G02B 26/105 359/205.1 |
| 2011/0014075 A1 | 1/2011 | Reif et al. .................. 417/477.12 |
| 2011/0032522 A1 | 2/2011 | Graves et al. .............. 356/338 |
| 2012/0156074 A1 | 6/2012 | Kusch et al. ............... 417/477.3 |
| 2012/0211679 A1 | 8/2012 | Heng et al. ................. 250/573 |
| 2012/0274925 A1 | 11/2012 | Chen et al. ................. 356/73 |
| 2012/0281204 A1 | 11/2012 | Hoshishima et al. ......... 356/72 |
| 2012/0282126 A1 | 11/2012 | Brandt et al. .............. 417/477.9 |
| 2012/0287419 A1 | 11/2012 | Sharpe et al. .............. 356/51 |
| 2013/0010181 A1 | 1/2013 | Baba .......................... 348/360 |
| 2013/0020498 A1 | 1/2013 | Ebi et al. .................... 250/435 |
| 2013/0050782 A1 | 2/2013 | Heng et al. ................. 358/494 |
| 2013/0070243 A1 | 3/2013 | Goehde ...................... 356/338 |
| 2013/0094102 A1 | 4/2013 | Baba .......................... 359/784 |
| 2013/0204538 A1 | 8/2013 | Rich ........................... 702/21 |

FOREIGN PATENT DOCUMENTS

| | | |
|---|---|---|
| CN | 201936066 U | 8/2011 |
| CN | 201984209 U | 9/2011 |
| CN | 102818794 | 12/2012 |
| CN | 102818795 | 12/2012 |
| CN | 102818796 | 12/2012 |
| EP | 459764 A2 | 12/1991 |
| EP | 459764 B1 | 12/1996 |
| EP | 757346 A1 | 2/1997 |
| EP | 758755 A2 | 2/1997 |
| EP | 0889319 | 1/1999 |
| EP | 757346 B1 | 11/2001 |
| EP | 1953526 | 8/2008 |
| EP | 1004907 | 4/2009 |
| EP | 2381475 | 3/2015 |
| JP | S55-144226 | 11/1980 |
| JP | S61-184427 | 8/1986 |
| JP | H03-197641 | 8/1991 |
| JP | H04-184241 | 7/1992 |
| JP | H05-119035 | 5/1993 |
| JP | 05333245 | 12/1993 |
| JP | 829726 | 2/1996 |
| JP | H09-502794 | 3/1997 |
| JP | H10-73528 | 3/1998 |
| JP | 2003-505707 | 2/2003 |
| JP | 2004-500572 | 1/2004 |
| JP | 2004-341204 | 12/2004 |
| JP | 2008-534960 | 8/2008 |
| JP | 2010-085194 | 4/2010 |
| JP | 2012-026837 | 2/2012 |
| WO | WO 9307471 | 4/1993 |
| WO | WO 9316368 | 8/1993 |
| WO | WO 9429695 | 12/1994 |
| WO | WO 9714066 A2 | 4/1997 |
| WO | WO 0057173 | 9/2000 |
| WO | WO 0127590 | 4/2001 |
| WO | WO 0140764 | 6/2001 |
| WO | WO 03012403 | 2/2003 |
| WO | WO 2005033654 | 4/2005 |
| WO | WO 2006013316 | 2/2006 |
| WO | WO 2009095358 | 8/2009 |
| WO | WO 2009098867 | 8/2009 |
| WO | WO 2011026942 | 3/2011 |
| WO | WO 2012056217 | 5/2012 |
| WO | WO 2012177367 | 12/2012 |
| WO | WO 2013013229 | 1/2013 |
| WO | WO 2013093035 | 6/2013 |
| WO | WO 2013/181453 | 12/2013 |

OTHER PUBLICATIONS

Extended European Search Report for EP 13796734.5, dated Mar. 18, 2016.
Goda et al., "Serial time-encoded amplified imaging for observation of fast dynamic phenomena," *Nature* 458:1145-1149. 2009.
International Search Report and Written Opinion for PCT/US2013/043453 dated Dec. 20, 2013.
International Search Report and Written Opinion for PCT/US2014/067682 dated Apr. 9, 2015.
Office Action issued in Chinese Patent Application No. 201380039184.6, dated Feb. 12, 2018.
Office Action issued in Japanese Patent Application No. 2015-515208, dated May 29, 2017 (English Translation Provided).
Office Action issued in Japanese Patent Application No. 2015-515208, dated May 2, 2018.
Office Action issued in Japanese Patent Application No. 2016-216891, dated Dec. 4, 2017 (English Translation).
Schmidt, B., "Ein lichtstarkes komafreies Spiegelsystem," *Mitteilungen der Haburger Sternwarte in Bergedorf* 7(36):15-17, 1932.
Smiley, C. H., "The Schmidt Camera," *Popular Astronomy* 44:415-421, 1936.

\* cited by examiner

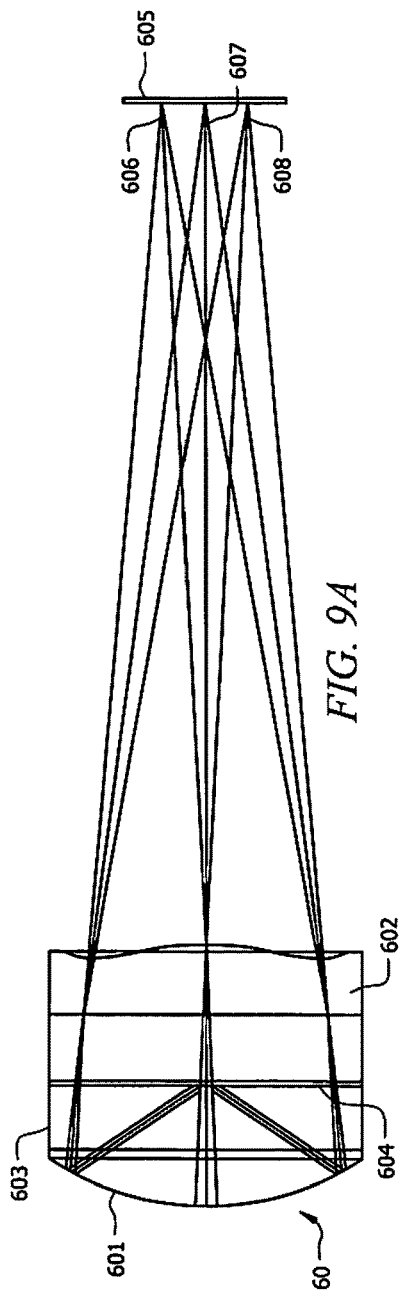
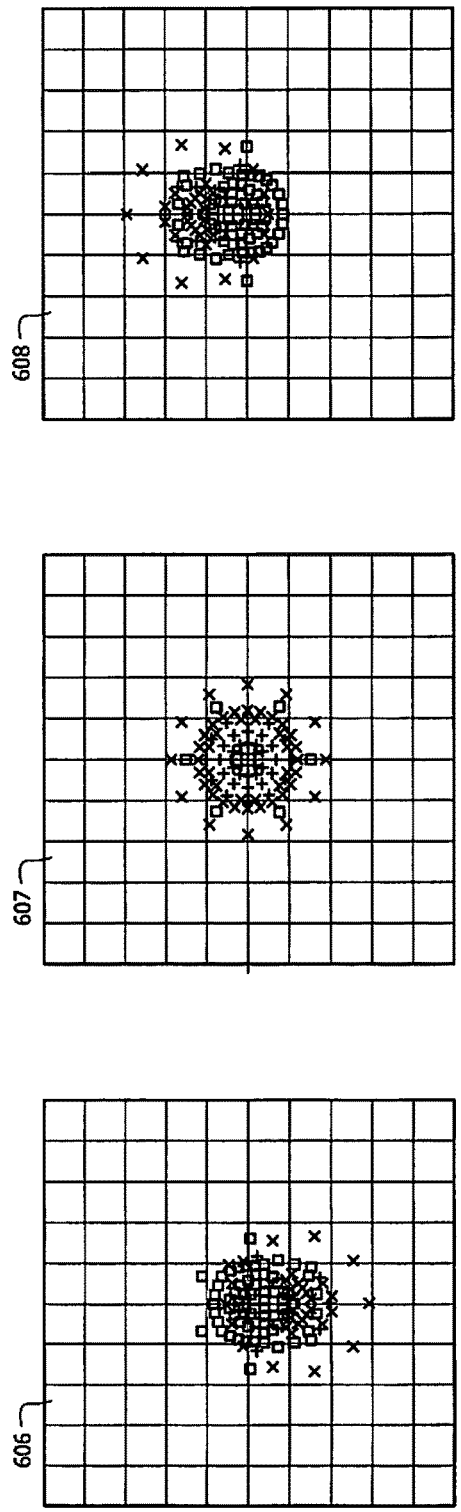

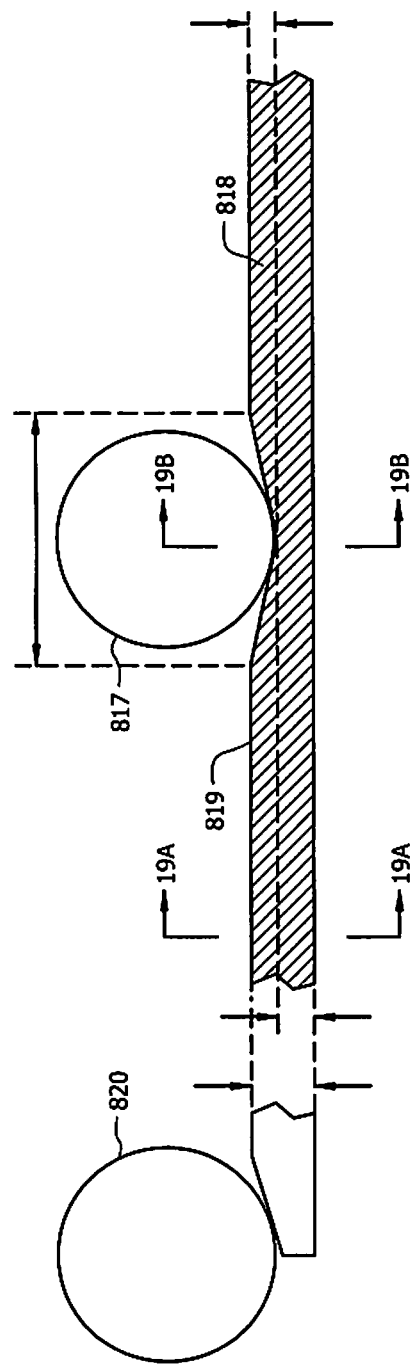
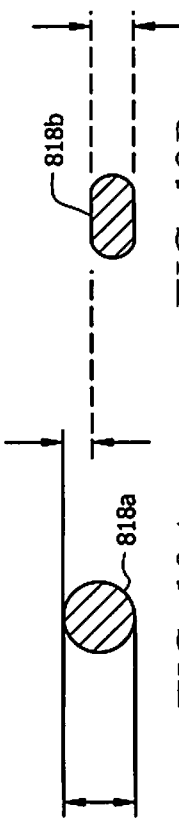
FIG. 19
FIG. 19A
FIG. 19B

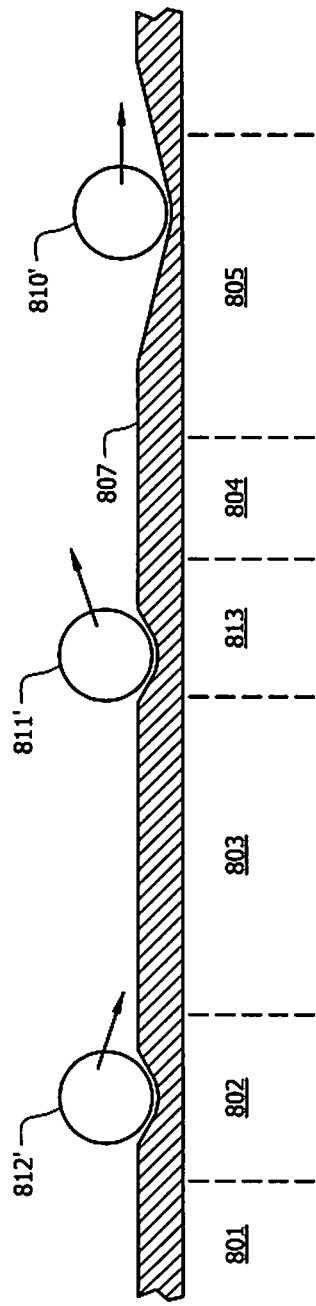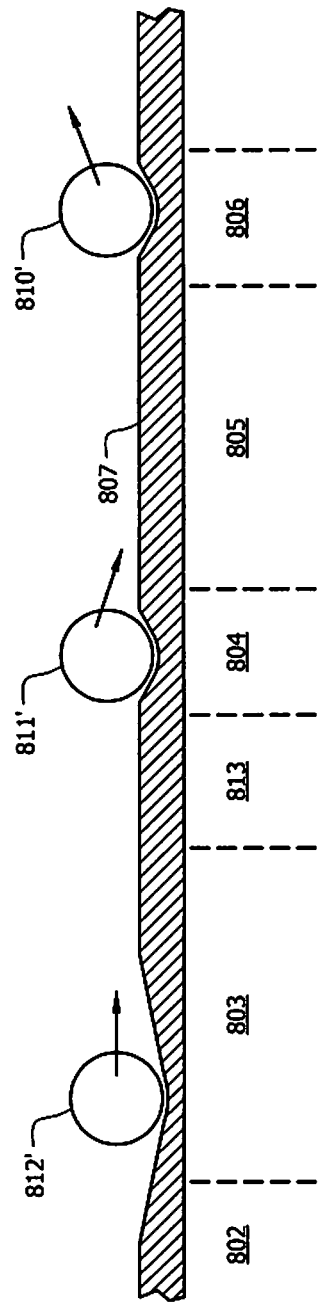

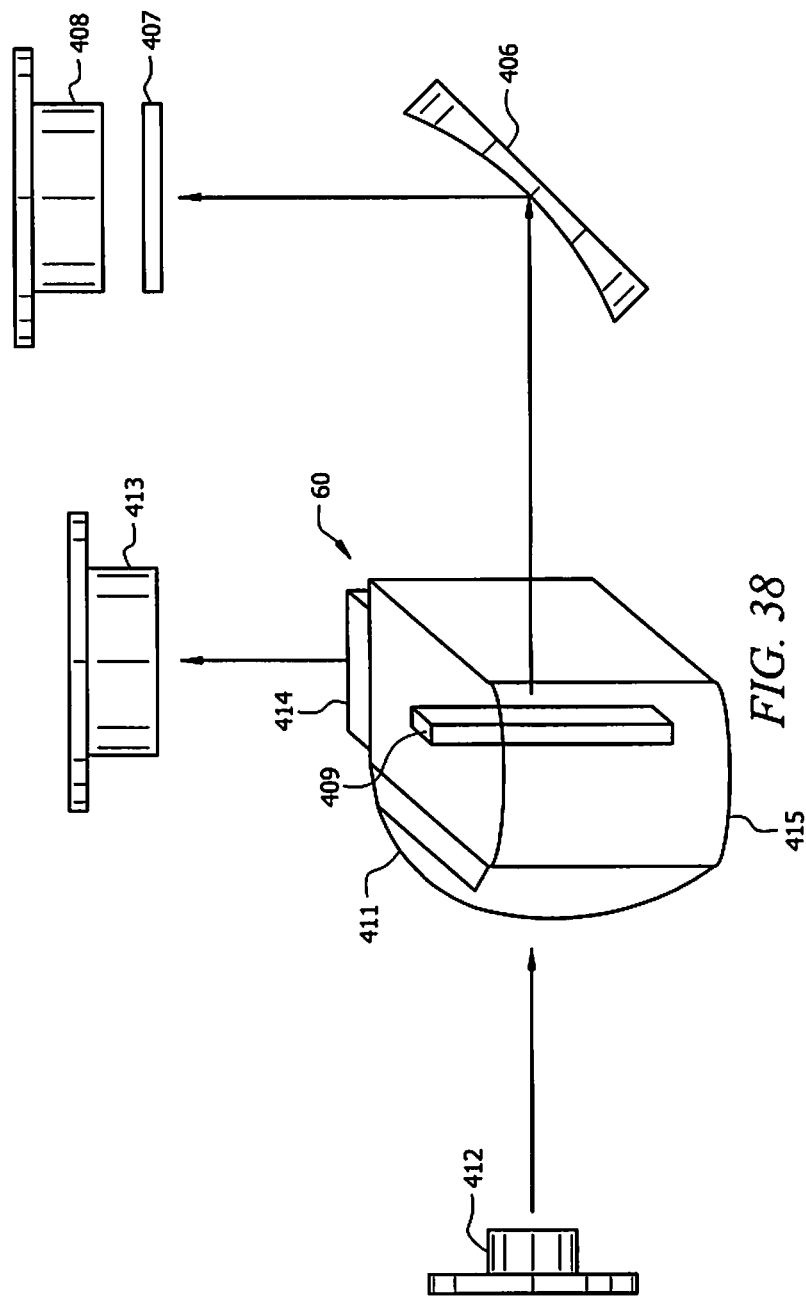

FLOW CYTOMETER

CROSS-REFERENCE TO RELATED APPLICATIONS

This application is a divisional of U.S. patent application Ser. No. 14/555,102 filed Nov. 26, 2014, which claims the benefit of priority of U.S. Provisional Patent Application Ser. No. 61/911,859 entitled "Flow Cytometer," filed on Dec. 4, 2013. U.S. patent application Ser. No. 14/555,102 is also a continuation-in-part of International Patent Application Serial No. PCT/US2013/043453 entitled "Flow Cytometer," filed on May 30, 2013, which claims the benefit of priority under 35 U.S.C. 119 to U.S. Provisional Patent Application Ser. No. 61/653,245 entitled "Pulseless Peristaltic Pump," filed on May 30, 2012, U.S. Provisional Patent Application Ser. No. 61/653,328 entitled "Composite Microscope Objective with a Dispersion Compensation Plate," filed on May 30, 2012, U.S. Provisional Patent Application Ser. No. 61/715,819 entitled "Wavelength Division Multiplexing for Extended Light Source," filed on Oct. 18, 2012, U.S. Provisional Patent Application Ser. No. 61/715,836 entitled "Diode Laser Based Optical Excitation System," filed on Oct. 19, 2012, and U.S. Provisional Patent Application Ser. No. 61/816,819 entitled "A Simple Fluidic System for Supplying Pulsation Free Liquid to Flow Cell," filed on Apr. 29, 2013. All of the above-identified applications are incorporated herein by reference in their entirety.

BACKGROUND

Technical Field

The present disclosure relates generally to the technical field of flow cytometry and, more particularly, to the structure and operation of an improved flow cytometer together with various individual subassemblies included therein.

Background

Flow cytometry is a biophysical technique employed in cell counting, sorting, biomarker detection and protein engineering. In flow cytometry, cells suspended in a stream of liquid pass through an electronic detection apparatus. Flow cytometry allows simultaneous multiparametric analysis of physical and/or chemical characteristics of up to thousands of cells per second.

Flow cytometry has various applications including in the fields of molecular biology, pathology, immunology, plant biology and marine biology. Flow cytometry also has broad application in medicine (especially in transplantation, hematology, tumor immunology and chemotherapy, prenatal diagnosis, genetics and sperm sorting for sex preselection). In marine biology, the autofluorescent properties of photosynthetic plankton can be exploited by flow cytometry in characterizing abundance and community composition. In protein engineering, flow cytometry is used in conjunction with yeast display and bacterial display to identify cell surface-displayed protein variants with desired properties. A common variation of flow cytometry is physically sorting particles based on their properties thereby purifying a population of interest.

SUMMARY OF DISCLOSURE

The present disclosure provides an improved flow cytometer together with various improved components included therein, as well as component groups with interacting components.

In certain embodiments, the present disclosure provides a simple and reliable diode laser based optical system capable of delivering a focused laser beam of elliptical cross section with a Gaussian like intensity distribution along its minor axis and a width along major axis optimized for flow cytometric applications.

In certain embodiments, the present disclosure provides an imaging quality microscope objective that is easy to manufacture and has long working distance, large numerical aperture, large field of view and minimal chromatic aberration.

In certain embodiments, the present disclosure provides a simple fluidics system for flow cytometers that is not only reliable, compact and easy to manufacture, but also capable of supporting velocity critical applications such as in instruments with multiple spatially separated excitation laser beams or in droplet sorters.

In certain embodiments, the present disclosure provides a simple design for a peristaltic pump providing a pulseless liquid flow.

In certain embodiments, the present disclosure provides a peristaltic pump with minimal pulsation.

In certain embodiments, the present disclosure provides a peristaltic pump that is simple to manufacture and operate.

In certain embodiments, the present disclosure provides a device capable of collimating a light beam from an extended light source over an extended distance without significantly expanding the beam diameter.

In certain embodiments, the present disclosure provides a Wavelength Division Multiplexing (WDM) system to separate a light beam into multiple colored bands. The WDM system may be compatible with low noise semiconductor detectors. In addition, due to the diversity of fluorescent probes, the WDM system may be reconfigurable.

According to an exemplary embodiment, a flow cytometer may include:

1. a Laser Diode (LD) based optical subsystem for impinging a beam of light upon particles passing through a viewing zone;

2. a composite microscope objective for gathering and imaging light scattered from or fluoresced by particles passing through the viewing zone;

3. a fluidic subsystem for supplying a liquid sheath flow to the viewing zone;

4. a peristaltic pump for injecting a liquid sample flow carrying particles that pass together with the liquid sheath flow through the viewing zone;

5. a multimode optical fiber that receives scattered and fluoresced light from the viewing zone that the composite microscope objective gathers images; and 6. a wavelength division multiplexer for optically separating light received via the optical fiber into color bands.

According to an exemplary embodiment, the LD based optical subsystem for illuminating particles passing through the flow cytometer's viewing zone may generally include:

1. a laser diode oriented with its slow axis parallel to the direction of flow;

2. a collimating lens that converts the diverging beam from the LD into a collimated beam of elliptical shape with its major axis perpendicular to the flow;

3. a focusing lens system that reduces the laser beam at the viewing zone to an optimal width in the direction perpendicular to the flow; and 4. finally a high power cylindrical focusing element placed in the proximity of the viewing zone with its axis perpendicular to the direction of flow.

The high power cylindrical focusing element may transpose the far field profile of the LD along its slow axis to its Fourier conjugate at the viewing zone along the direction of flow, while maintains the transverse beam profile, such that the laser beam profile at the viewing zone is optimal for flow cytometric applications.

According to an exemplary embodiment, the composite microscope objective may generally include:

1. a concave spherical mirror;
2. a transparent aberration compensation plate with the flow cytometer's a viewing zone being located between the mirror and the plate. Scatter and fluorescence light emitted from particles in the viewing zone is collected by the mirror and reflected back toward the compensation plate. Optical aberrations originating from the mirror are significantly reduced after light passes through the compensation plate. In one embodiment of the present disclosure, the viewing zone may be located inside a flow cell provided by rectangular glass cuvette with a small rectangular channel through which a particle carrying liquid flows. The concave mirror may be made of an optically transparent material, such as glass or optical quality plastics, of plano-convex shape with a highly-reflective coating on the convex side for internal reflection. The plano-side of the mirror may be either gel-coupled or bonded to one side surface of the cuvette. The plano-aspheric compensation plate may be made of a transparent material, such as glass or optical quality plastics, with the plano side gel-coupled or bonded to the opposite side of the cuvette. The plano-convex shaped mirror and the aspheric compensation plate may also be formed integrally with the cuvette. In yet another embodiment of the present disclosure, the viewing zone may be in a jet stream with both the concave mirror and the compensation plate being free standing from the viewing zone, and the mirror may be a front surface concave mirror.

According to an exemplary embodiment, the fluidic system may generally include a sheath liquid reservoir from which a liquid pump draws sheath liquid. Sheath liquid then flows from the liquid pump to an inlet of a T-coupling. One outlet arm of the T-coupling connects to a bypass that returns a fraction of the pumped sheath liquid back to the sheath liquid reservoir with the returned sheath liquid flowing into air within the sheath liquid reservoir. A second outlet arm of the T-coupling connects to a sheath route that includes a reservoir capsule followed by a particle filter and then the flow cell. The sheath liquid exiting the flow cell then goes to the waste tank. The fluidic resistance along the bypass is designed to be lower than the fluidic resistance along the sheath route. Consequently, only a small fraction of the sheath liquid goes through the flow cell. Note that typical sheath flow rate in flow cytometric applications is a few tens of milliliter per minute. The bypass therefore permits using higher flow rate liquid pumps that not only are much less expensive and more reliable, but also operates at higher pulsation frequency which is much easier to attenuate. Since the exit of the bypass route connects to air, it also serves as a large fluidic capacitor for significantly reducing pulsation in sheath liquid flowing along the sheath route. During operation, the inlet portion of the filter cartridge is filled with air. Therefore, the filter cartridge also serves as a fluidic capacitor, for further reducing pulsation in the sheath liquid at the flow cell to negligible level. Due to the large fluidic resistance at the flow cell, the air trapped near the inlet of the filter cartridge becomes compressed. If the liquid pump is turned off, the compressed air in filter cartridge being pushed back towards the sheath liquid reservoir becomes stored in the reservoir capsule whose size is chosen to prevent the trapped air from reaching the T-coupling.

According to an exemplary embodiment, the peristaltic pump may generally include a plurality of rollers located at the periphery of a rotor that moves the rollers circularly inside a housing's arcuate curved track and a compressible tube that the rollers compress against the track. In one embodiment of the present disclosure, the track of the peristaltic pump's housing may have one recess so the compressible tube is progressively decompressed to full expansion then compressed to full closure every time one of the rollers moves past the recess. The location and shape of the recess maintains the total volume of liquid within the compressible tube from the recess to the pump's outlet substantially invariant. The effect of tube expansion as a roller moves past the pump's outlet is compensated by the tube compression when a different other roller immediately upstream of the pump outlet moves into the recess' compressing section. In another embodiment of the present disclosure, the track of the pump housing may contain a plurality of recesses, providing for a plurality of roller upstream of the pump outlet to progressively modify the tube compression in multiple sections along the compressible tube. The locations and shapes of the plurality of recesses are designed such that the modification of tube compression at these sections substantially compensates the effect due to the tube expansion near the pump outlet. In yet another embodiment of the present disclosure, the compressible tube is kept fully closed underneath the roller except in the inlet and exit sections. A variable speed motor may be used to drive the pump. When a roller reaches the exit section, the motor's rotation may programmatically speed up to compensate for the tube's expansion.

According to an exemplary embodiment, a wavelength division multiplexer ("WDM") may include at least two optical elements. The first optical element collimates a beam of light received from an extended light source, such as the light from a pinhole or from a multimode optical fiber. The first optical element magnifies the extended light source, for example, as defined by the pinhole, or the core of the multimode optical fiber, to an image having a size similar to the effective cross section of the first optical element thereby creating a collimated light beam between the first optical element and its image. A second optical element is positioned near the image, and relays the first optical element with unit magnification down the optical path. In this way, the second optical element effectively doubles the collimated path length. Additional optical elements in the same 1:1 image relay configuration may also be included to further extend the collimated optical path. The cascaded unit-magnification image relay architecture of the present disclosure extends the collimated optical path length without large beam expansion. As a result, WDM techniques well-established in the optical communication industry can be readily adapted for fluorescence light detection. In particular, multiple colored bands present in the beam of light can be separated using dichroic filters located along the optical path with the separated light being tightly focused into small spots compatible with low noise semiconductor photodetectors.

In one embodiment of a WDM, the first optical element is a lens and the second element is a concave mirror, although it is apparent to those skilled in the art that other types of refractive and/or reflective optical components may also be used to achieve the same design goal. The optical path in the WDM of the present disclosure may be folded using dichroic filters. In one embodiment of the present disclosure, the light path may be folded into a zig-zag configuration. To facilitate the flow cytometer's reliable reconfiguration, each dichroic filter may be bonded to a mechanical holder having a reference surface that is optically parallel to the filter's reflective surface. As a result, all of the WDM's filters can be accurately positioned along the optical path by referencing the filter's holder against a common optical flat. In another embodiment of the present disclosure, the collimated beam passing through the dichroic filter is further branched out into multiple colored bands using secondary dichroic filters. It is apparent to those skilled in the art that dichroic filters may be inserted anywhere along the long, narrow and collimated beam path afforded by the present disclosure's relay imaging to thereby permit delivering a tightly focused beam to photo detectors using a variety of optical configurations, such as the star configuration discussed in U.S. Pat. No. 6,683,314, the branched configuration discussed in U.S. Pat. No. 4,727,020 and other types of WDM optical configuration widely practiced in the optical communication industry. Instead of concave mirrors, the WDM may be replaced by curved dichroic filters to further increase the number of colored bands selected by the WDM.

According to some exemplary embodiments, an optical system for impinging beams of light into a viewing zone in which a sample flow carrying objects and a sheath flow pass through includes a first light source for emitting a first beam of light along a first beam path to illuminate objects in the viewing zone at a first location, a second light source for emitting a second beam of light along a second beam path to illuminate objects in the viewing zone at a second location, a beam compressing optical element for reducing widths of the first and second beams of light on their major axes to a width less than the width of the sheath flow, and a first chromatic compensation element located on at least one of the first beam path and the second beam path for compensating chromatic aberration in the viewing zone such that the first location and the second locations are on a common plane parallel to the direction of the sample flow. The wavelength of the second light source is different from the wavelength of the first light source. The chromatic compensation allows compensating the properties of the different paths, resulting e.g. from the different wavelengths, the different path lengths, different locations in the flow path etc. This applies also for multiple compensating elements in different paths, in particular when using two, three or more wavelengths for illumination.

According to some exemplary embodiments, an optical system includes a first light source for emitting a first beam of light to illuminate objects at a first location in a viewing zone, a composite microscope objective for imaging light scattered from and fluoresced by the objects at the first location in the viewing zone at an image plane external to the composite microscope, and a beam splitter for reflecting or transmitting scattered and fluoresced light, wherein the light source and the image plane are on two sides of the beam splitter. The composite microscope includes a concave mirror and an aberration corrector plate. The aberration corrector plate is an aspheric lens that has a first zone with negative optical power and a second zone with positive optical power radially inside the first zone. The viewing zone is positioned between the concave mirror and the aberration corrector plate. This allows a compact build-up, as the illumination and the detection of light scattered from and fluoresced by the objects in the viewing zone may be conducted from the same side of the microscope objective.

According to some exemplary embodiments, an axial light detection system includes a concave mirror for reflecting light that propagates from a viewing zone, and a detector for measuring axial light loss produced by an object in the viewing zone by detecting light reflected by the concave mirror. This allows an effective detection of light loss which may serve as a base for better interpretation of the measured values.

According to some exemplary embodiments, a power monitoring system for adjusting power of a light source includes a first light source for emitting a first beam of light, a second light source for emitting a second beam of light, a first dichroic filter for reflecting the first beam of light and passing the second beam of light, a second dichroic filter for reflecting the second beam of light, a first detector for measuring residual power of the first and second beams of light downstream of the first dichroic filter on a time-division multiplexing basis, and a control unit coupled with the first detector and the first and second light sources, wherein the control unit adjusts power of one or more of the first and second light sources based on measured residual power of the first and second beams of light by the first detector. This allows an effective detection of light power which may serve as a base for better interpretation of the measured values, as well as an effective control procedure, in particular when controlling or adaption respective light sources.

According to another exemplary embodiment, an optical system includes an objective adapted for imaging light scattered from and fluoresced by an illuminated object within a viewing zone, an optical transmission member for propagating light received from the aspheric lens, a wavelength division multiplexer (WDM) for receiving light propagated by the optical transmission member. The objective includes an aspheric lens with a first zone with negative optical power and a second zone inside the first zone with positive optical power, and a concave mirror for reflecting light scattered from and fluoresced by the illuminated object through the aspheric lens, wherein the viewing zone is located between said concave mirror and the aspheric lens. The WDM includes a first optical element that produces a beam of light with an image of substantially the same size as the effective size of said first optical element, at least one dichroic filter located between said first optical element and said image, a second optical element located in one of said branches, and an image relay optical element located near the image produced by said first optical element in the other branch. The dichroic filter separates the beam of light into two branches of distinctive colors. The beam of light in said branch is focused to a spot by said second optical element. The image relay optical element produces an image of said first optical element at substantially unit magnification. This allows an adapted combined operation of the microscope objective and the WDM, as well as the optical coupling there between. In particular the microscope objective and the WDM as well as the optical coupling may be adapted to match to each other with respect to wavelength and other parameters.

According to another exemplary embodiment, an optical system includes a light source for emitting a beam of light to illuminate an object in a viewing zone, a concave mirror for receiving and reflecting light scattered from and fluoresced by the illuminated object, an aspheric lens with a first zone with negative optical power and a second zone inside the first zone with positive optical power, wherein light reflected by the concave mirror passes through the aspheric lens, and wherein the viewing zone is located between said concave mirror and the aspheric lens, an optical transmission member for receiving and propagating light from the aspheric lens, and a multiplexer for receiving light from the optical transmission member and separating the light into at least two colors. This allows an adapted combined operation of the illumination system, the microscope objective and the WDM, as well as the optical coupling there between. In particular the illumination system, the microscope objective and the WDM as well as the optical coupling may be adapted to match to each other with respect to wavelength and other parameters.

According to another exemplary embodiment, an apparatus for imaging light scattered from and fluoresced by an illuminated object within a viewing zone includes a fluid delivery system for delivering an object to a viewing zone, a light source for illuminating the object in the viewing zone, a concave mirror located on one side of the viewing zone for reflecting light scattered from and fluoresced by the illuminated object, and an aspheric lens located on another side of the viewing zone for receiving the light reflected by the concave mirror and forming an image at an image plane, the aspheric lens having a first zone with negative optical power and a second zone radially inside the first zone with positive optical power. This allows an adapted combined operation of the fluid delivery system, the illumination system, and the microscope objective. In particular the fluid delivery system, the illumination system, and the microscope objective may be adapted to match to each other with respect to wavelength and other parameters.

According to other exemplary embodiments, an optical method for impinging beams of light into a viewing zone includes directing a first beam of light to illuminate objects in a viewing zone to produce scattered and fluoresced light, reflecting the scattered and fluoresced light using a concave mirror toward an aberration corrector plate, correcting aberrations in the reflected light with the aberration corrector plate, wherein the aberration corrector plate has a first zone with negative optical power a second zone radially inside the first zone with positive optical power, and reflecting or transmitting the corrected light using a beam splitter.

According to other exemplary embodiments, an optical method for detecting light includes reflecting light that propagates from a viewing zone using a concave mirror, and measuring axial light loss produced by an object in the viewing zone by detecting light reflected by the concave mirror.

According to other exemplary embodiments, a method of gathering and imaging light scattered from or fluoresced by objects in a viewing includes delivering an object to a viewing zone, illuminating the object in the viewing zone to produce scattered and fluoresced light, reflecting the scattered and fluoresced light using a concave mirror toward a transparent aberration corrector plate, and correcting spherical aberrations in the reflected light with the transparent aberration corrector plate, wherein the transparent aberration corrector plate has a first zone with negative optical power and a second zone radially inside the first zone with positive optical power.

According to other exemplary embodiments, a composite microscope objective adapted for imaging light scattered from and fluoresced by an object present within a viewing zone, comprises a viewing zone, a concave mirror arrangement, an exit area and an illumination beam forming arrangement, wherein the viewing zone is arranged between the concave mirror arrangement and the exit area, and wherein the concave mirror is arranged to reflect scattered and fluoresced light impinging from an object present in the viewing zone to the exit area, and wherein the illumination beam forming arrangement is arranged so that an illumination beam entering the illumination beam forming arrangement is pre-definitely formed at the viewing zone. According to other exemplary embodiments there may be provided an aberration corrector plate, in particular an aspheric lens in the exit area. This allows an effective build-up of the microscope objective. It should be noted that the aberration corrector plate is not necessary when providing a concave mirror shape allowing a sufficient imaging of the light scattered and fluoresced from an object in the viewing zone. If required an aberration corrector plate, in particular an aspheric lens may be arranged in the exit area.

According to other exemplary embodiments a wavelength division multiplexer (WDM) for separating light emitted from a light source into multiple colored bands comprises an imaging optical arrangement, a dichroic filter arrangement, a semiconductor photo detector, and a focusing optical arrangement, wherein the imaging optical arrangement forms a beam of light from the light emitted from a light source and produces an image of substantially the same size as the effective size of said imaging optical arrangement, and wherein the dichroic filter arrangement is located between said imaging optical arrangement and said image, and separates the beam of light into a first branch and a second branch of distinctive colors, and wherein the semiconductor photo detector is located in the first branch, and wherein the focusing optical arrangement is located between the dichroic filter arrangement and the semiconductor photo detector so as to focus the beam of light onto the semiconductor photo detector. Thus, an effective detection arrangement may be provided, which may be operated with a semiconductor detector. The semiconductor detector may be a semiconductor photo detector. The semiconductor detector may be an avalanche photo diode or a carbon nanotube detector. Thus, a reduced signal to noise ratio can be achieved.

In first aspect of the disclosure, a flow cytometer includes a laser diode (LD) based optical subsystem for directing a beam of light into a viewing zone of said flow cytometer through which a sample liquid carrying particles flows, the sample liquid being hydrodynamically focused within the viewing zone by a liquid sheath flow that also flows through the viewing zone, a composite microscope objective for imaging light scattered from and fluoresced by a particle present within the viewing zone, a fluidic subsystem for supplying the liquid sheath flow to the viewing zone, the liquid sheath flow lacking pulsations, a peristaltic pump for supplying the sample liquid carrying the particles, the sample liquid being hydrodynamically focused within the viewing zone by the liquid sheath flow, a peristaltic pump for supplying the sample liquid carrying the particles, the sample liquid being hydrodynamically focused within the viewing zone by the liquid sheath flow, and a wavelength division multiplexer (WDM) for separating into multiple colored bands a beam of light emitted initially from the viewing zone and imaged by the composite microscope objective into an optical fiber for transmission to the WDM. The LD based optical subsystem may include a LD for emitting a diverging beam of light from an edge thereof, the diverging beam of light having an elliptically shaped cross-sectional profile with both a major axis and a minor axis, a collimating lens for converting the diverging beam of light emitted from said LD into a collimated elliptical beam of light, wherein the minor axis of said collimated elliptical beam of light is oriented parallel to a direction in which particles pass through the viewing zone, a beam compressing optical element for reducing the size of said elliptical beam of light at the viewing zone whereby a width of said major axis of said elliptical beam of light oriented perpendicular to the direction in which particles pass through the viewing zone is less than a width of said liquid sheath flow, a cylindrical focusing element positioned adjacent to the viewing zone with an axis of said cylindrical focusing element being oriented perpendicular to the direction in which particles pass through the viewing zone whereby said minor axis of said beam of light becomes focused at the viewing zone, and the size of said major axis of said elliptical beam of light at the viewing zone remains essentially unchanged. The composite microscope objective may include a concave mirror upon which scattered and fluoresced light impinges and an aberration corrector plate made of optically transparent material. The aberration corrector plate is an aspheric lens that has a first zone of said aberration corrector plate having negative optical power outside a neutral zone and a second zone of said aberration corrector plate inside the neutral zone having positive optical power light. The neutral zone is the thinnest portion of the aberration corrector plate. Light reflected from the concave mirror passes through said aberration corrector plate. The viewing zone of said flow cytometer is located between said concave mirror and said aberration corrector plate. The fluidic subsystem may include a liquid pump for supplying liquid drawn from a reservoir and a T-coupling having at least one (1) inlet and two (2) outlets. The inlet of said T-coupling receives liquid from said liquid pump. A first fraction of the liquid received by the inlet flows via a first one of the outlets and via a bypass conduit back to the reservoir. A second fraction of the liquid received by the inlet flows via a second one of the outlets and via a particle filter to the viewing zone of said flow cytometer. The peristaltic pump may include a pump housing having a arcuate curved track formed therein that extends between a pump inlet and a pump outlet, a plurality of rollers that are attached to a rotor, the rollers having a substantially equal angular spacing between each pair of immediately adjacent rollers, the rotor being rotatable together with the rollers attached thereto inside said pump housing, and a compressible tube sandwiched between said rollers and the arcuate curved track of said pump housing. The arcuate curved track includes an exit section and at least one pumping section along the arcuate curved track between the pump inlet and the pump outlet. As a roller rolls through the exit section, said compressible tube adjacent to said roller progressively expands from fully closed at a beginning of said exit section to fully open at the pump outlet where said roller breaks contact with said compressible tube. Said compressible tube is compressed to fully closed by at least one of said rollers. The wavelength division multiplexer (WDM) may include a collimating optical element that magnifies an to produce an image of substantially the same size as the effective size of said collimating optical element, at least one dichroic filter located between said collimating optical element and said image, said dichroic filter separating the collimated beam of light into two (2) branches of distinctive colors, a focusing optical element located in one of said branches, the beam of light in said branch being focused to a spot having a diameter of less than 1.0 mm by said focusing optical element, and an image relay optical element located near the image produced by said collimating optical element in the other branch, said image relay optical element producing an image of said collimating optical element at substantially unit magnification.

In second aspect of the disclosure, said cuvette may have a rectangularly-shaped cross-section, and the viewing zone of the flow cytometer is located within a channel having a rectangularly-shaped cross-section that is located within said cuvette.

In third aspect of the disclosure, said cuvette may have a tubularly-shaped cross-section, and the viewing zone of the flow cytometer is located within a channel having a circularly-shaped cross-section that is located within said cuvette.

In fourth aspect of the disclosure, the sample liquid and the liquid sheath flow form a jet stream in which the viewing zone of the flow cytometer is located.

In fifth aspect of the disclosure, said cylindrical focusing element is in optical contact with an entrance face of said rectangularly-shaped cuvette.

In sixth aspect of the disclosure, said cylindrical focusing element is separated from said rectangularly-shaped cuvette.

In seventh aspect of the disclosure, said cylindrical focusing element is separated from said tubularly-shaped cuvette.

In eighth aspect of the present disclosure, said cylindrical focusing element is separated from said jet stream.

In ninth aspect of the present disclosure, the flow cytometer further comprises a polarization conditioning element through which said collimated elliptical beam of light passes.

In tenth aspect of the present disclosure, an optical image of the viewing zone is formed outside the composite microscope objective.

In eleventh aspect of the present disclosure, the viewing zone is located within a flow channel included in a rectangularly-shaped cuvette made of optically transparent material.

In twelfth aspect of the present disclosure, said concave mirror is a plano-concave back surface mirror made from an optically transparent material.

In thirteenth aspect of the present disclosure, the plano-surface of said plano-concave back surface mirror is optically coupled to a flat surface of said cuvette.

In fourteenth aspect of the present disclosure, an optical adhesive material accomplishes the optical coupling.

In fifteenth aspect of the present disclosure, an index matching gel accomplishes the optical coupling.

In sixteenth aspect of the present disclosure, an index matching fluid accomplishes the optical coupling.

In seventeenth aspect of the present disclosure, optical contact bonding accomplishes the optical coupling.

In eighteenth aspect of the present disclosure, the plano-concave back surface mirror formed integrally with said cuvette means.

In nineteenth aspect of the present disclosure, said aberration corrector plate is a plano-aspherical lens.

In twentieth aspect of the present disclosure, a plano-surface of said aberration corrector plate is optically coupled to a flat surface of said cuvette opposite of said plano-concave back surface mirror.

In twenty-first aspect of the present disclosure, an index matching gel accomplishes the optical coupling.

In twenty-second aspect of the present disclosure, an index matching fluid accomplishes the optical coupling.

In twenty-third aspect of the present disclosure, optical contact bonding accomplishes the optical coupling.

In twenty-fourth aspect of the present disclosure, the plano-aspherical lens is formed integrally with said cuvette.

In twenty-fifth aspect of the present disclosure, said aberration corrector plate is detached from said cuvette.

In twenty-sixth aspect of the present disclosure, the viewing zone is inside a jet stream.

In twenty-seventh aspect of the present disclosure, said concave mirror is a front surface mirror.

In twenty-eighth aspect of the present disclosure, the viewing zone is located on a surface of a flat, transparent substrate.

In twenty-ninth aspect of the present disclosure, said concave mirror is a plano-concave back surface mirror made from an optically transparent material.

In thirtieth aspect of the present disclosure, the plano-surface of said plano-concave back surface mirror is optically coupled to said flat, transparent substrate.

In thirty-first aspect of the present disclosure, an optical adhesive material accomplishes the optical coupling.

In thirty-second aspect of the present disclosure, an index matching gel accomplishes the optical coupling.

In thirty-third aspect of the present disclosure, an index matching fluid accomplishes the optical coupling.

In thirty-fourth aspect of the present disclosure, optical contact bonding accomplishes the optical coupling.

In thirty-fifth aspect of the present disclosure, said plano-concave back surface mirror is formed integrally with said flat, transparent substrate.

In thirty-sixth aspect of the present disclosure, said aberration corrector plate is detached from said flat, transparent substrate.

In thirty-seventh aspect of the present disclosure, the particle filter has inlet thereto for receiving liquid from the T-coupling, the inlet of the particle filter being disposed so that air becomes trapped within the particle filter at the inlet thereto.

In thirty-eighth aspect of the present disclosure when said liquid pump is turned off air cannot enter into the bypass conduit.

In thirty-ninth aspect of the present disclosure, the flow cytometer further comprises a small capsule disposed between the second one of the outlets of said T-coupling and the particle filter for storing air ejected from the particle filter when the liquid pump is turned off.

In fortieth aspect of the present disclosure, the flow cytometer further comprises a length of tubing disposed between the second one of the outlets of said T-coupling and the particle filter for storing air ejected from the particle filter when the liquid pump is turned off.

In forty-first aspect of the present disclosure, the flow cytometer further comprises an adjustable valve located in the bypass conduit between the first one of the outlets of the T-coupling and the reservoir for restricting liquid flow therebetween.

In forty-second aspect of the present disclosure, the flow cytometer further comprises an adjustable valve located between the second one of the outlets of the T-coupling and the viewing zone for restricting liquid flow therebetween.

In forty-third aspect of the present disclosure, the throughput of the liquid pump is adjustable.

In forty-fourth aspect of the present disclosure, the arcuate curved track of said pump housing includes at least two (2) pumping sections, the arcuate curved track further including at least one recess section located between said pumping sections along the arcuate curved track, and said compressible tube at said recess section becoming decompressed to full expansion then compressed to fully closed when one (1) of said rollers rolls through said recess section.

In forty-fifth aspect of the present disclosure, the peristaltic pump includes a plurality of recess sections along said arcuate curved track upstream of the pump outlet, the angular spacing between the compression part of said recess section adjacent to the pump outlet and said exit section of said arcuate curved track being substantially the same as the angular spacing between each pair of immediately adjacent rollers.

In forty-sixth aspect of the present disclosure, said compression part of said recess section adjacent to the pump outlet has a shape complementing a shape of said exit section of said arcuate curved track to maintain the total fluid volume inside a section of said compressible tube extending from said recess section to the pump outlet substantially invariant when one of said rollers progressively rolls off said exit section of the arcuate curved track.

In forty-seventh aspect of the present disclosure, the peristaltic pump includes a plurality of recess sections respectively interspersed between immediately adjacent pairs of a plurality of pumping sections.

In forty-eighth aspect of the present disclosure, both angular spacing between adjacent pairs of recess sections, and angular spacing between said exit section of said arcuate curved track and an adjacent recess section to said exit section are substantially the same as the angular spacing between each pair of immediately adjacent rollers.

In forty-ninth aspect of the present disclosure, shapes of a plurality of recess sections of said arcuate curved track complement a shape of said exit section of said arcuate curved track to maintain a fluid volume in sections of said compressible tube at the plurality of recess sections and said exit section substantially invariant when one of said rollers progressively rolls off said exit section of the arcuate curved track.

In fiftieth aspect of the present disclosure, a speed of said rotor is programmably controlled to vary substantially in inverse proportion to the fluid volume change rate in said compressible tube due to its changing compression near the exit section of said arcuate curved track.

In fifty-first aspect of the present disclosure, at least one additional dichroic filter is located between said image relay optical element and the image produced by said image relay optical element, said dichroic filter producing two (2) branches of the beam of light having distinctive colors.

In fifty-second aspect of the present disclosure, another focusing optical element is located in one of said branches and focuses the beam of light in the branch into a spot having a diameter of less than 1.0 mm.

In fifty-third aspect of the present disclosure, wherein successive combinations of said image relay optical element, dichroic filter, and focusing optical element are cascaded to produce additional focused spots having a diameter of less than 1.0 mm for multiple colored bands of said beam of light.

In fifty-fourth aspect of the present disclosure, the dichroic filter is assembled using a template that include two (2) optically flat glass plates bonded together in optical contact, and the dichroic filter is bonded to a filter holder using the template such that a coated filter surface of the dichroic filter is indented and optically parallel to a reference surface of the filter holder.

In fifty-fifth aspect of the present disclosure, the reference surface of the filter holder rests against an optically flat surface of an reference block included in the WDM thereby providing consistent optical alignment when installing the dichroic filter into the WDM.

In fifty-sixth aspect of the present disclosure, the LD based optical subsystem includes a LD for emitting a diverging beam of light from an edge thereof, the diverging beam of light having an elliptically shaped cross-sectional profile with both a major axis and a minor axis, a collimating lens for converting the diverging beam of light emitted from said LD into a collimated elliptical beam of light, wherein the minor axis of said collimated elliptical beam of light is oriented parallel to a direction in which particles pass through the viewing zone, a beam compressing optical element for reducing the size of said elliptical beam of light at the viewing zone whereby a width of said major axis of said elliptical beam of light oriented perpendicular to the direction in which particles pass through the viewing zone is less than a width of said liquid sheath flow, a cylindrical focusing element positioned adjacent to the viewing zone with an axis of said cylindrical focusing element being oriented perpendicular to the direction in which particles pass through the viewing zone whereby said minor axis of said beam of light becomes focused at the viewing zone, and the size of said major axis of said elliptical beam of light at the viewing zone remains essentially unchanged.

In fifty-seventh aspect of the present disclosure, the optical subsystem may further comprise a cuvette having a rectangularly-shaped cross-section, and the viewing zone may be located within a channel having a rectangularly-shaped cross-section that is located within said cuvette.

In fifty-eighth aspect of the present disclosure, the optical subsystem further comprises a cuvette having a tubularly-shaped cross-section, and the viewing zone is located within a channel having a circularly-shaped cross-section that is located within said cuvette.

In fifty-ninth aspect of the present disclosure, the sample liquid and the liquid sheath flow form a jet stream in which the viewing zone is located.

In sixtieth aspect of the present disclosure, cylindrical focusing element is in optical contact with an entrance face of said rectangularly-shaped cuvette.

In sixty-first aspect of the present disclosure, said cylindrical focusing element is separated from said rectangularly-shaped cuvette.

In sixty-second aspect of the present disclosure, said cylindrical focusing element is separated from said tubularly-shaped cuvette.

In sixty-third aspect of the present disclosure, said cylindrical focusing element is separated from said jet stream.

In sixty-fourth aspect of the present disclosure, the optical subsystem (50) further comprises a polarization conditioning element through which said collimated elliptical beam of light passes.

In sixty-fifth aspect of the present disclosure, a method for delivering an elliptically shaped beam of light using a LD based optical subsystem (50), the beam of light having a smooth profile at a focus of a minor axis thereof that is located at a viewing zone through which a sample liquid flows, the sample liquid being hydrodynamically focused within the viewing zone by a liquid sheath flow that also flows through the viewing zone, the method includes the steps of: providing a LD that emits a diverging beam of light from an edge thereof, the diverging beam of light having an elliptically shaped cross-sectional profile with both a major axis and a minor axis, impinging the diverging beam of light emitted by the LD upon a collimating lens for converting the diverging beam of light emitted therefrom into a collimated elliptical beam of light wherein the minor axis of said collimated elliptical beam of light is oriented parallel to a direction in which sample liquid passes through the viewing zone, after passing through said collimating lens, impinging the collimated elliptical beam of light upon an beam compressing optical element for reducing the size of said elliptical beam of light at the viewing zone whereby a width of said major axis of said elliptical beam of light oriented perpendicular to the direction in which sample liquid passes through the viewing zone becomes less than a width of said liquid sheath flow, and after passing through said beam compressing optical element, impinging the beam of light upon a cylindrical focusing element positioned adjacent to the viewing zone with an axis of said cylindrical focusing element being oriented perpendicular to the direction in which sample liquid passes through the viewing zone whereby said minor axis of said beam of light becomes focused at the viewing zone, and the size of said major axis of said elliptical beam of light at the viewing zone remains essentially unchanged.

In sixty-sixth aspect of the present disclosure, the viewing zone is located within a channel having a rectangularly-shaped cross-section that is located within a cuvette.

In sixty-seventh aspect of the present disclosure, the viewing zone is located within a channel having a circularly-shaped cross-section that is located within a cuvette.

In sixty-eighth aspect of the present disclosure, the viewing zone is located within a jet stream.

In sixty-ninth aspect of the present disclosure, the method further comprises a step of establishing an optical contact between said cylindrical focusing element and an entrance face of said cuvette.

In seventieth aspect of the present disclosure, the method further comprises a step of establishing a spacing between said cylindrical focusing element and said cuvette.

In seventy-first aspect of the present disclosure, the method further comprises a step of establishing a spacing between said cylindrical focusing element and said cuvette.

In seventy-second aspect of the present disclosure, the method further comprise a step of establishing a spacing between said cylindrical focusing element and said jet stream.

In seventy-third aspect of the present disclosure, the method further comprises a step of inserting a polarization conditioning element between the collimating lens and the beam compressing optical element whereby the collimated elliptical beam of light passes through the polarization conditioning element.

In seventy-fourth aspect of the present disclosure, The composite microscope objective includes a concave mirror upon which scattered and fluoresced light impinges and an aberration corrector plate made of optically transparent material. The aberration corrector plate is an aspheric lens that has a first zone of said aberration corrector plate having negative optical power outside a neutral zone and a second zone of said aberration corrector plate inside the neutral zone having positive optical power light. The neutral zone is the thinnest portion of the aberration corrector plate. Light reflected from the concave mirror passes through said aberration corrector plate. The viewing zone of said flow cytometer is located between said concave mirror and said aberration corrector plate.

In seventy-fifth aspect of the present disclosure, an optical image of the viewing zone is formed outside the composite microscope objective.

In seventy-sixth aspect of the present disclosure, the viewing zone is located within a flow channel included in a rectangularly-shaped cuvette made of optically transparent material.

In seventy-seventh aspect of the present disclosure, said concave mirror is a plano-concave back surface mirror made from an optically transparent material.

In seventy-eighth aspect of the present disclosure, a plano-surface of said plano-concave back surface mirror is optically coupled to a flat surface of said cuvette.

In seventy-ninth aspect of the present disclosure, an optical adhesive material accomplishes the optical coupling.

In eightieth aspect of the present disclosure an index matching gel accomplishes the optical coupling.

In eighty-first aspect of the present disclosure, an index matching fluid accomplishes the optical coupling.

In eighty-second aspect of the present disclosure, optical contact bonding accomplishes the optical coupling.

In eighty-third aspect of the present disclosure, the plano-concave back surface mirror formed integrally with said cuvette means.

In eighty-fourth aspect of the present disclosure, said aberration corrector plate is a plano-aspherical lens.

In eighty-fifth aspect of the present disclosure, a plano-surface of said aberration corrector plate is optically coupled to a flat surface of said cuvette opposite of said plano-concave back surface mirror.

In eighty-sixth aspect of the present disclosure, an index matching gel accomplishes the optical coupling.

In eighty-seventh aspect of the present disclosure, an index matching fluid accomplishes the optical coupling.

In eighty-eighth aspect of the present disclosure, optical contact bonding accomplishes the optical coupling.

In eighty-ninth aspect of the present disclosure, the plano-aspherical lens is formed integrally with said cuvette.

In ninetieth aspect of the present disclosure said aberration corrector plate is detached from said cuvette.

In ninety-first aspect of the present disclosure, the viewing zone is inside a jet stream.

In ninety-second aspect of the present disclosure, said concave mirror is a front surface mirror.

In ninety-third aspect of the present disclosure, the viewing zone is located on a surface of a flat, transparent substrate.

In ninety-fourth aspect of the present disclosure, said concave mirror is a plano-concave back surface mirror made from an optically transparent material.

In ninety-fifth aspect of the present disclosure, a plano-surface of said plano-concave back surface mirror is optically coupled to said flat, transparent substrate.

In ninety-sixth aspect of the present disclosure, an optical adhesive material accomplishes the optical coupling.

In ninety-seventh aspect of the present disclosure, an index matching gel accomplishes the optical coupling.

In ninety-eighth aspect of the present disclosure, an index matching fluid accomplishes the optical coupling.

In ninety-ninth aspect of the present disclosure, optical contact bonding accomplishes the optical coupling.

In one hundredth aspect of the present disclosure, said plano-concave back surface mirror is formed integrally with said flat, transparent substrate.

In one hundred first aspect of the present disclosure, said aberration corrector plate is detached from said flat, transparent substrate.

In one hundred second aspect of the present disclosure, a method for characterizing microscopic species using a microscope objective device includes a concave mirror, an aberration corrector plate made of optically transparent material, and a viewing zone located in between said concave mirror and said aberration corrector plate. The aberration corrector plate is an aspheric lens that has a first zone of said aberration corrector plate having negative optical power outside a neutral zone and a second zone of said aberration corrector plate inside the neutral zone having positive optical power light. The neutral zone is the thinnest portion of the aberration corrector plate.

In one hundred third aspect of the present disclosure, an optical image of the viewing zone is formed outside the device.

In one hundred fourth aspect of the present disclosure, the viewing zone is located within a flow channel contained in a rectangularly-shaped cuvette means made of optically transparent material.

In one hundred fifth aspect of the present disclosure, said concave mirror is a plano-concave back surface mirror made from an optically transparent material.

In one hundred sixth aspect of the present disclosure, a plano-surface of said plano-concave back surface mirror means is optically coupled to a flat surface of said cuvette means.

In one hundred seventh aspect of the present disclosure, an optical adhesive material accomplishes the optical coupling.

In one hundred eighth aspect of the present disclosure, an index matching gel accomplishes the optical coupling.

In one hundred ninth aspect of the present disclosure, an index matching fluid accomplishes the optical coupling.

In one hundred tenth aspect of the present disclosure, optical contact bonding accomplishes the optical coupling.

In one hundred eleventh aspect of the present disclosure the plano-concave back surface mirror is formed integrally with said cuvette.

In one hundred twelfth aspect of the present disclosure, said aberration corrector plate is a plano-aspherical lens.

In one hundred thirteenth aspect of the present disclosure, a plano-surface of said aberration corrector plate is optically coupled to a flat surface of said cuvette means opposite of said concave mirror.

In one hundred fourteenth aspect of the present disclosure an index matching gel accomplishes the optical coupling.

In one hundred fifteenth aspect of the present disclosure, an index matching fluid accomplishes the optical coupling.

In one hundred sixteenth aspect of the present disclosure, optical contact bonding accomplishes the optical coupling.

In one hundred seventeenth aspect of the present disclosure, the plano-aspherical lens is formed integrally with said cuvette.

In one hundred eighteenth aspect of the present disclosure, said aberration corrector plate is detached from said cuvette.

In one hundred nineteenth aspect of the present disclosure, the viewing zone is inside a jet stream.

In one hundred twentieth aspect of the present disclosure, said concave mirror is a front surface mirror.

In one hundred twenty-first aspect of the present disclosure, the viewing zone is located on a surface of a flat, transparent substrate.

In one hundred twenty-second aspect of the present disclosure said concave mirror is a plano-concave back surface mirror made from an optically transparent material.

In one hundred twenty-third aspect of the present disclosure, a plano-surface of said plano-concave back surface mirror means is optically coupled to said flat, transparent substrate.

In one hundred twenty-fourth aspect of the present disclosure, an optical adhesive material accomplishes the optical coupling.

In one hundred twenty-fifth aspect of the present disclosure, an index matching gel accomplishes the optical coupling.

In one hundred twenty-sixth aspect of the present disclosure, an index matching fluid accomplishes the optical coupling.

In one hundred twenty-seventh aspect of the present disclosure, optical contact bonding accomplishes the optical coupling.

In one hundred twenty-eighth aspect of the present disclosure, said plano-concave back surface mirror is formed integrally with said flat, transparent substrate.

In one hundred twenty-ninth aspect of the present disclosure, said aberration corrector plate is detached from said flat, transparent substrate.

In one hundred thirtieth aspect of the present disclosure, a fluidic subsystem for supplying a liquid flow pulsation free to an outlet of the fluidic subsystem includes a liquid pump for supplying liquid drawn from a reservoir and a T-coupling having at least one inlet and two outlets. The inlet of said T-coupling receives liquid from said liquid pump. A first fraction of the liquid received by the inlet flows via a first one of the outlets and via a bypass conduit back to the reservoir. A second fraction of the liquid received by the inlet flows via a second one of the outlets and via a particle filter to the viewing zone of said flow cytometer.

In one hundred thirty-first aspect of the present disclosure, the particle filter has an inlet thereto for receiving liquid from the T-coupling, the inlet of the particle filter being disposed so that air becomes trapped within the particle filter at the inlet thereto.

In one hundred thirty-second aspect of the present disclosure, when said liquid pump is turned off air cannot enter into the bypass conduit.

In one hundred thirty-third aspect of the present disclosure, the fluidic subsystem further comprises a small capsule disposed between the second one of the outlets of said T-coupling and the particle filter for storing air ejected from the particle filter when the liquid pump is turned off.

In one hundred thirty-fourth aspect of the present disclosure, the fluidic subsystem further comprises a length of tubing disposed between the second one of the outlets of said T-coupling and the particle filter for storing air ejected from the particle filter when the liquid pump is turned off.

In one hundred thirty-fifth aspect of the present disclosure, the fluidic subsystem further comprises an adjustable valve located in the bypass conduit between the first one of the outlets of the T-coupling and the reservoir for restricting liquid flow therebetween.

In one hundred thirty-sixth aspect of the present disclosure, the fluidic subsystem further comprises an adjustable valve located between the second one of the outlets of the T-coupling and the outlet of the fluidic subsystem for restricting liquid flow therebetween.

In one hundred thirty-seventh aspect of the present disclosure, the throughput of the liquid pump is adjustable.

In one hundred thirty-eighth aspect of the present disclosure, a method for supplying a liquid flow pulsation free to an outlet of the fluidic subsystem includes a liquid pump for supplying liquid drawn from a reservoir and a T-coupling having at least one (1) inlet and two (2) outlets. The inlet of said T-coupling receives liquid from said liquid pump. A first fraction of the liquid received by the inlet flows via a first one of the outlets and via a bypass conduit back to the reservoir. A second fraction of the liquid received by the inlet flows via a second one of the outlets and via a particle filter to the viewing zone of said flow cytometer.

In one hundred thirty-ninth aspect of the present disclosure, during normal operation certain amount of air is trapped near the inlet portion of said filter cartridge means.

In one hundred fortieth aspect of the present disclosure said reservoir means holds sufficient amount of liquid such that when said pump means is turned off, portion of the tubing between said T-coupling means and said reservoir means is still filled with liquid, preventing said trapped air from leaking into said bypass means.

In one hundred forty-first aspect of the present disclosure, said reservoir means is a capsule.

In one hundred forty-second aspect of the present disclosure, said reservoir means is a piece of tubing.

In one hundred forty-third aspect of the present disclosure an adjustable flow restrictor means is placed in the bypass route.

In one hundred forty-fourth aspect of the present disclosure an adjustable flow restrictor means is placed in the sheath route.

In one hundred forty-fifth aspect of the present disclosure, the throughput of the sheath pump is adjustable.

In one hundred forty-sixth aspect of the present disclosure, a peristaltic pump includes a pump housing having an arcuate curved track formed therein that extends between a pump inlet and a pump outlet, a plurality of rollers that are attached to a rotor, the rollers having a substantially equal angular spacing between each pair of immediately adjacent rollers, the rotor being rotatable together with the rollers attached thereto inside said pump housing, and a compressible tube sandwiched between said rollers and the arcuate curved track of said pump housing. The arcuate curved track includes an exit section and at least one pumping section along the arcuate curved track between the pump inlet and the pump outlet. As a roller rolls through the exit section, said compressible tube adjacent to said roller progressively expands from fully closed at a beginning of said exit section to fully open at the pump outlet where said roller breaks contact with said compressible tube. Said compressible tube is compressed to fully closed by at least one of said rollers.

In one hundred forty-seventh aspect of the present disclosure, the arcuate curved track of said pump housing includes at least two (2) pumping sections, the arcuate curved track further including at least one recess section located between said pumping sections along the arcuate curved track, and wherein said compressible tube at said recess section becomes decompressed to full expansion then compressed to fully closed when one (1) of said rollers rolls through said recess section.

In one hundred forty-eighth aspect of the present disclosure, the peristaltic pump includes a plurality of recess sections along said arcuate curved track upstream of the pump outlet, the angular spacing between the compression part of said recess section adjacent to the pump outlet and said exit section of said arcuate curved track being substantially the same as the angular spacing between each pair of immediately adjacent rollers.

In one hundred forty-ninth aspect of the present disclosure, said compression part of said recess section adjacent to the pump outlet has a shape complementing a shape of said exit section of said arcuate curved track to maintain the total fluid volume inside a section of said compressible tube extending from said recess section to the pump outlet substantially invariant when one of said rollers progressively rolls off said exit section of the arcuate curved track.

In one hundred fiftieth aspect of the present disclosure, the peristaltic pump has a plurality of recess sections respectively interspersed between immediately adjacent pairs of a plurality of pumping sections.

In one hundred fifty-first aspect of the present disclosure, both angular spacing between adjacent pairs of recess sections, and angular spacing between said exit section of said arcuate curved track and an adjacent recess section to said exit section are substantially the same as the angular spacing between each pair of immediately adjacent roller.

In one hundred fifty-second aspect of the present disclosure, shapes of a plurality of recess sections of said arcuate curved track complement a shape of said exit section of said arcuate curved track to maintain a fluid volume in sections of said compressible tube at the plurality of recess sections and said exit section substantially invariant when one of said rollers progressively rolls off said exit section of the arcuate curved track.

In one hundred fifty-third aspect of the present disclosure, a speed of said rotor is programmably controlled to vary substantially in inverse proportion to the fluid volume change rate in said compressible tube due to its changing compression near the exit section of said arcuate curved track.

In one hundred fifty-fourth aspect of the present disclosure, a method for delivering liquid using a peristaltic pump includes a pump housing having a arcuate curved track formed therein that extends between a pump inlet and a pump outlet, a plurality of rollers that are attached to a rotor, the rollers having a substantially equal angular spacing between each pair of immediately adjacent rollers, the rotor being rotatable together with the rollers attached thereto inside said pump housing, and a compressible tube sandwiched between said rollers and the arcuate curved track of said pump housing. The arcuate curved track includes an exit section and at least one pumping section along the arcuate curved track between the pump inlet and the pump outlet. As a roller rolls through the exit section, said compressible tube adjacent to said roller progressively expands from fully closed at a beginning of said exit section to fully open at the pump outlet where said roller breaks contact with said compressible tube. Said compressible tube is compressed to fully closed by at least one of said rollers.

In one hundred fifty-fifth aspect of the present disclosure the arcuate curved track of said pump housing includes at least two (2) pumping sections, the arcuate curved track further including at least one recess section located between said pumping sections along the arcuate curved track, and wherein said compressible tube at said recess section becomes decompressed to full expansion then compressed to fully closed when one (1) of said rollers rolls through said recess section.

In one hundred fifty-sixth aspect of the present disclosure, the peristaltic pump includes a plurality of recess sections along said arcuate curved track upstream of the pump outlet; The angular spacing between the compression part of said recess section adjacent to the pump outlet and said exit section of said arcuate curved track being substantially the same as the angular spacing between each pair of immediately adjacent rollers.

In one hundred fifty-seventh aspect of the present disclosure, said compression part of said recess section adjacent to the pump outlet has a shape complementing a shape of said exit section of said arcuate curved track to maintain the total fluid volume inside a section of said compressible tube extending from said recess section to the pump outlet substantially invariant when one of said rollers progressively rolls off said exit section of the arcuate curved track.

In one hundred fifty-eighth aspect of the present disclosure, the pump has a plurality of recess sections respectively interspersed between immediately adjacent pairs of a plurality of pumping sections.

In one hundred fifty-ninth aspect of the present disclosure, both angular spacing between adjacent pairs of recess sections, and angular spacing between said exit section of said arcuate curved track and an adjacent recess section to said exit section are substantially the same as the angular spacing between each pair of immediately adjacent roller.

In one hundred sixtieth aspect of the present disclosure, shapes of a plurality of recess sections of said arcuate curved track complement a shape of said exit section of said arcuate curved track to maintain a fluid volume in sections of said compressible tube at the plurality of recess sections and said exit section substantially invariant when one of said rollers progressively rolls off said exit section of the arcuate curved track.

In one hundred sixty-first aspect of the present disclosure, a speed of said rotor of the peristaltic pump is programmably controlled to vary substantially in inverse proportion to the fluid volume change rate in said compressible tube due to its changing compression near the exit section of said arcuate curved track.

In one hundred sixty-second aspect of the present disclosure, the wavelength division multiplexer (WDM) includes a collimating optical element that magnifies an to produce an image of substantially the same size as the effective size of said collimating optical element, at least one dichroic filter located between said collimating optical element and said image, said dichroic filter separating the collimated beam of light into two (2) branches of distinctive colors, a focusing optical element located in one of said branches, the beam of light in said branch being focused to a spot having a diameter of less than 1.0 mm by said focusing optical element, and an image relay optical element located near the image produced by said collimating optical element in the other branch, said image relay optical element producing an image of said collimating optical element at substantially unit magnification.

In one hundred sixty-third aspect of the present disclosure, at least one additional dichroic filter is located between said image relay optical element and the image produced by said image relay optical element, wherein said dichroic filter produces two (2) branches of the beam of light having distinctive colors.

In one hundred sixty-fourth aspect of the present disclosure, another focusing optical element is located in one of said branches and focuses the beam of light in the branch into a spot having a diameter of less than 1.0 mm.

In one hundred sixty-fifth aspect of the present disclosure, successive combinations of said image relay optical element, dichroic filter and focusing optical element are cascaded to produce additional focused spots having a diameter of less than 1.0 mm for multiple colored bands of said beam of light.

In one hundred sixty-sixth aspect of the present disclosure, the dichroic filter is assembled using a template that include two (2) optically flat glass plates bonded together in optical contact, and wherein the dichroic filter is bonded to a filter holder using the template such that a coated filter surface of the dichroic filter is indented and optically parallel to a reference surface of the filter holder.

In one hundred sixty-seventh aspect of the present disclosure, the reference surface of the filter holder rests against an optically flat surface of an reference block included in the WDM thereby providing consistent optical alignment when installing the dichroic filter into the WDM.

In one hundred sixty-eighth aspect of the present disclosure, a method for separating beam of light into colored bands using a WDM includes a collimating optical element that magnifies an to produce an image of substantially the same size as the effective size of said collimating optical element, at least one dichroic filter located between said collimating optical element and said image, said dichroic filter separating the collimated beam of light into two (2) branches of distinctive colors, a focusing optical element located in one of said branches, the beam of light in said branch being focused to a spot having a diameter of less than 1.0 mm by said focusing optical element, and an image relay optical element located near the image produced by said collimating optical element in the other branch, said image relay optical element producing an image of said collimating optical element at substantially unit magnification.

In one hundred sixty-ninth aspect of the present disclosure, at least one additional dichroic filter may be located between said image relay optical element and the image produced by said image relay optical element, wherein said dichroic filter produces two (2) branches of beam of light having distinctive colors.

In one hundred seventieth aspect of the present disclosure, another focusing optical element is located in one of said branches and focuses the beam of light in the branch into a spot having a diameter of less than 1.0 mm.

In one hundred seventy-first aspect of the present disclosure, successive combinations of said image relay optical element, dichroic filter and focusing optical element are cascaded to produce additional focused spots having a diameter of less than 1.0 mm for multiple colored bands of said beam of light.

In one hundred seventy-second aspect of the present disclosure, the dichroic filter is assembled using a template that include two (2) optically flat glass plates bonded together in optical contact, and wherein the dichroic filter is bonded to a filter holder using the template such that a coated filter surface of the dichroic filter is indented and optically parallel to a reference surface of the filter holder.

In one hundred seventy-third aspect of the present disclosure, the reference surface of the filter holder rests against an optically flat surface of an reference block included in the WDM thereby providing consistent optical alignment when installing the dichroic filter into the WDM.

In one aspect of the disclosure, a flow cytometer having a wavelength division multiplexer (WDM), which includes an extended light source providing light that forms an object, a collimating optical element that captures light from the extended light source and projects a magnified image of the object as a first light beam, and a first focusing optical element configured to focus the first light beam to a size smaller than the object of the extended light source to a first semiconductor detector.

In an additional aspect of the disclosure, a flow cytometer includes a viewing zone where a particle in a flow stream is illuminated by light, and a composite microscope objective. The composite microscope objective further includes a concave mirror configured to gather light scattered from or fluoresced by the illuminated particle and to reflect the light back towards the viewing zone, and an aberration corrector plate configured to reduce optical aberrations in the reflected light caused by the concave mirror.

In an additional aspect of the disclosure, a flow cytometer having a fluidic system, which includes a liquid pump for supplying liquid drawn from a reservoir, and a T-coupling having at least one inlet and two outlets. The inlet of the T-coupling receives the liquid from the liquid pump. The first fraction of the liquid received by the inlet flows via a first one of the outlets and via a bypass conduit back to the reservoir. The second fraction of the liquid received by the inlet flows via a second one of the outlets and via a particle filter to the outlet of the fluidic system.

In an additional aspect of the disclosure, a flow cytometer having a peristaltic pump, which includes a pump housing having an arcuate curved track formed therein that extends between a pump inlet and a pump outlet, a plurality of rollers that are attached to a rotor, the rollers having a substantially equal angular spacing between each pair of immediately adjacent rollers, the rotor being rotatable together with the rollers attached thereto inside the pump housing, a compressible tube sandwiched between the rollers and the arcuate curved track of the pump housing, and a recess section located between the at least two pumping sections. The compressible tube at the recess section is not fully closed. The arcuate curved track further includes an exit section and at least two pumping sections along the arcuate curved track between the pump inlet and the pump outlet. As one of the plurality of rollers rolls through the exit section, the compressible tube adjacent to the roller progressively expands from fully closed at a beginning of the exit section to fully open at the pump outlet where the roller breaks contact with the compressible tube. The compressible tube is compressed to fully closed by at least one of the plurality of rollers at the at least two pumping sections.

In an additional aspect of the disclosure, a flow cytometer having a laser diode (LD) system, which includes a LD for emitting a diverging beam of light from an edge thereof, the diverging beam of light having an elliptically shaped cross-sectional profile with both a major axis and a minor axis, a collimating lens for converting the diverging beam of light emitted from the LD into a collimated elliptical beam of light, the minor axis of the collimated elliptical beam of light being oriented parallel to a direction in which particles pass through a viewing zone, a beam compressing optical element for reducing the size of the elliptical beam of light at the viewing zone whereby a width of the elliptical beam of light oriented perpendicular to the direction in which the particles pass through the viewing zone is less than a width of a liquid sheath flow, and a cylindrical focusing element positioned adjacent to the viewing zone with an axis of the cylindrical focusing element being oriented perpendicular to the direction in which the particles pass through the viewing zone whereby the minor axis of the elliptical beam of light becomes focused at the viewing zone; and the size of the major axis of the elliptical beam of light at the viewing zone remains essentially unchanged.

The foregoing has outlined rather broadly the features and technical advantages of the present application in order that the detailed description that follows may be better understood. Additional features and advantages will be described hereinafter which form the subject of the claims. It should be appreciated by those skilled in the art that the conception and specific aspect disclosed may be readily utilized as a basis for modifying or designing other structures for carrying out the same purposes of the present application. It should also be realized by those skilled in the art that such equivalent constructions do not depart from the spirit and scope of the present application and the appended claims. The novel features which are believed to be characteristic of aspects, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present claims.

a) a LD based optical illumination subsystem;

b) a composite microscope objective upon which light emitted from the LD based optical illumination subsystem impinges, the composite microscope objective having a fluid-passing channel formed therethrough with a particle illumination viewing zone located inside a cuvette thereof;

c) a fluidic system for supplying a pulsation free flow of sheath liquid to the fluid-passing channel formed through the composite microscope objective;

d) a peristaltic pump for introducing a pulsation free flow of sample liquid that carries cells or particles to be analyzed into the sheath flow of liquid supplied by the fluidic system; and e) a wavelength division multiplexer ("WDM") having a zig-zag configuration for separating a beam of light into several different colored bands, the WDM receiving light via an optical fiber that is scattered from cells or particles as they pass through the composite microscope objective's fluid passing channel and are illuminated therein by light emitted from the LD based optical illumination subsystem.

Figure 2:
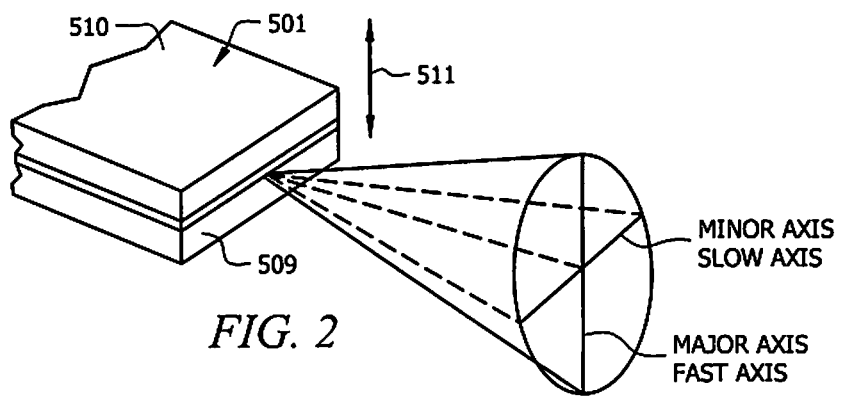

FIG. 2 is a schematic view depicting a typical high power edge emitting LD that illustrates the fast and slow axes of light emitted therefrom.

Figure 2A:
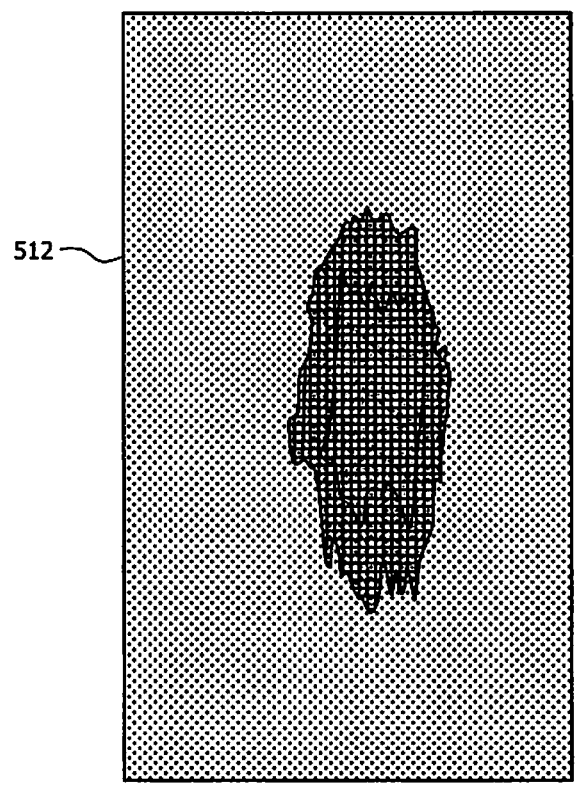

FIG. 2A shows a typical far field profile for a laser beam emitted from the LD chip depicted in FIG. 2.

Figure 3A:
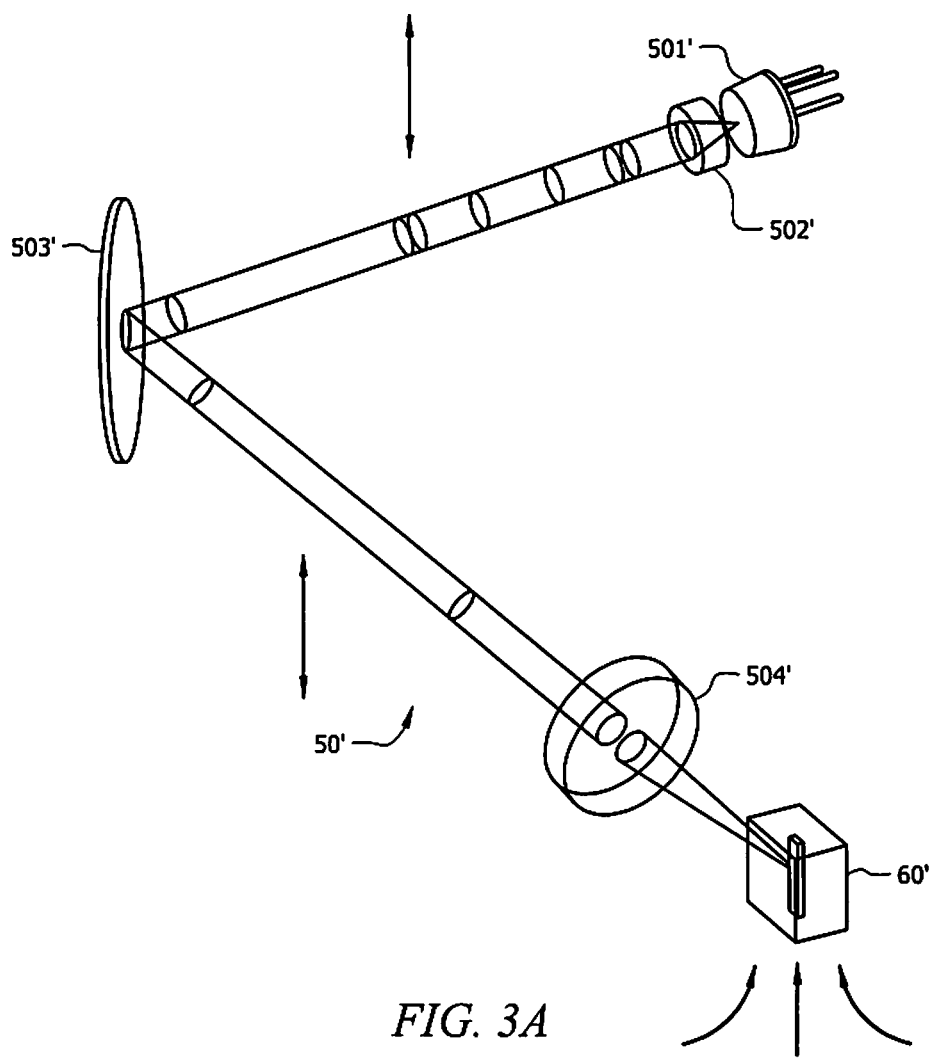

FIG. 3A depicts a 3-dimensional view of a conventional LD based optical illumination subsystem for flow cytometric instruments together with the system's flow cell.

Figure 3B:
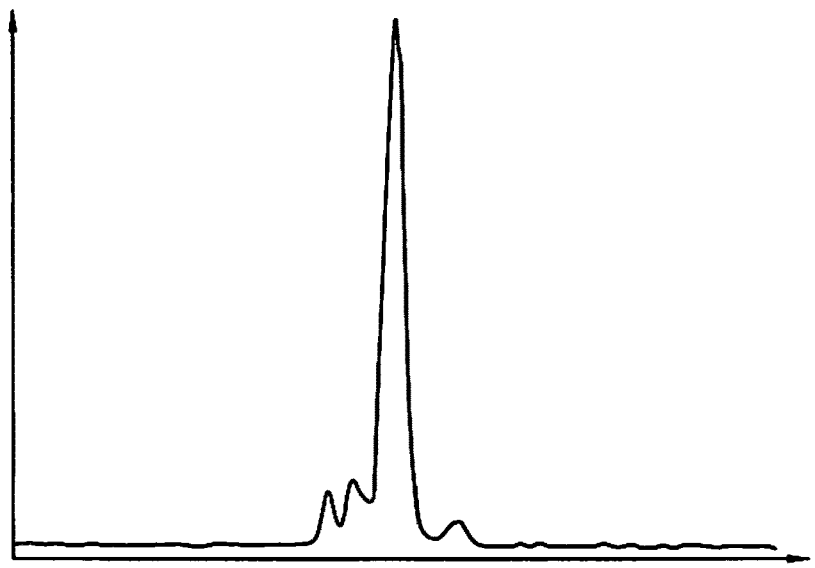

FIG. 3B depicts a typical time dependent profile of light scattering from a cell or particle passing through the laser beam depicted in FIG. 3A at the focus thereof within the system's flow cell.

Figure 4A:
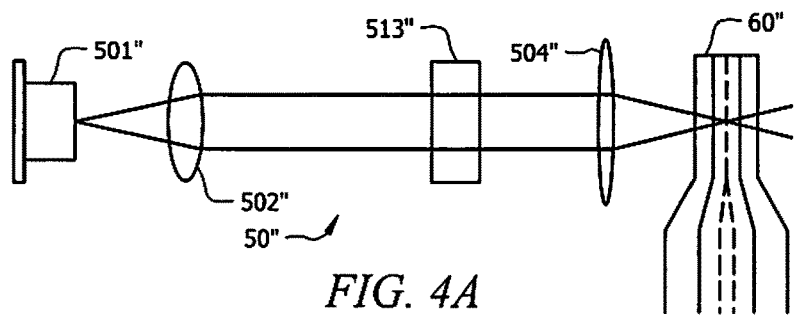

FIG. 4A is an elevational view of an alternative prior art LD based optical illumination subsystem configuration across the liquid flowing through the fluid-passing channel with the beam profile at the focus thereof in the flow cytometer system's viewing zone.

Figure 4B:
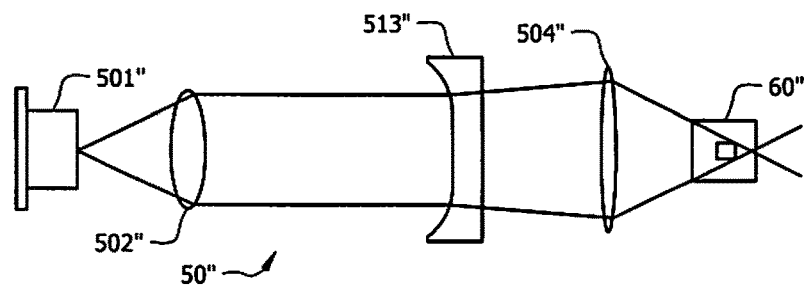

FIG. 4B is a plan view along the liquid flowing through the fluid-passing channel of the alternative prior art LD based optical illumination subsystem depicted in FIG. 4A.

Figure 1:
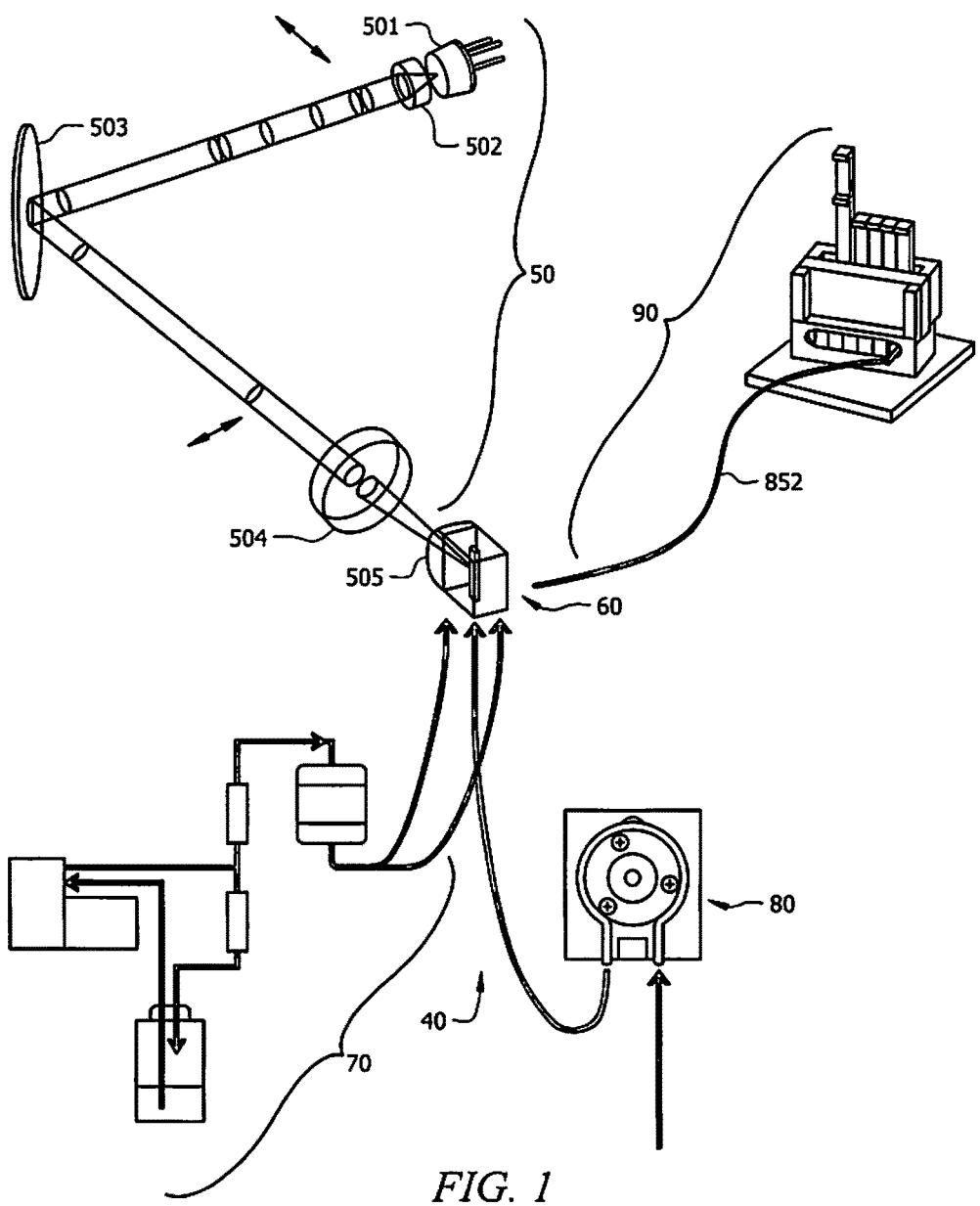
FIG. 1 is a diagram schematically illustrating an embodiment of a flow cytometer in accordance with the present disclosure that includes.
Figure 5A:
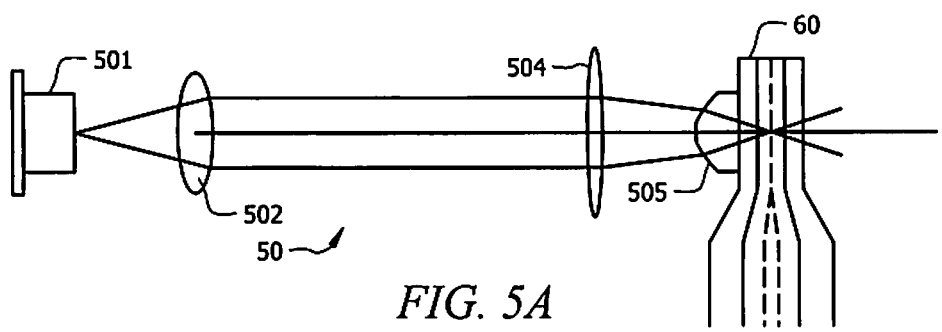

FIG. 5A is an elevational view across liquid flowing through the fluid-passing channel of the composite microscope objective depicted in FIG. 1, wherein the LD's slow axis oriented transversely to the liquid flow in accordance with one aspect of the present disclosure.

Figure 5B:
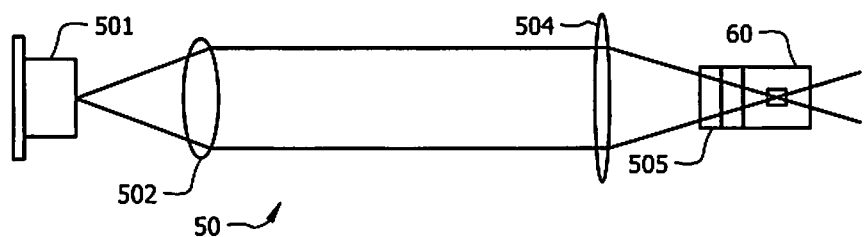

FIG. 5B is a plan view along liquid flowing through the fluid-passing channel of the composite microscope objective depicted in FIG. 1, wherein the LD's slow axis oriented transversely to the liquid flow in accordance with one aspect of the present disclosure.

Figure 5C:
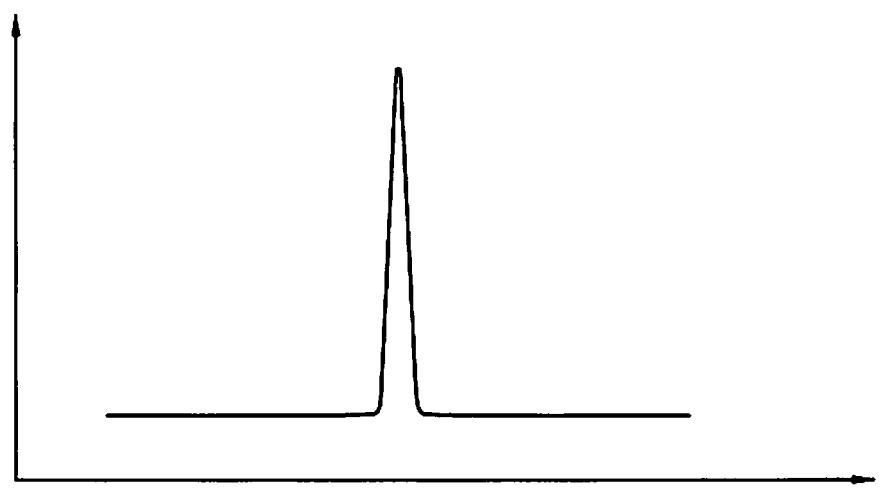

FIG. 5C depicts a typical time dependent profile of light scattering from a cell or particle passing through the fluid passing channel of the composite microscope objective depicted in FIG. 1.

Figure 5D:
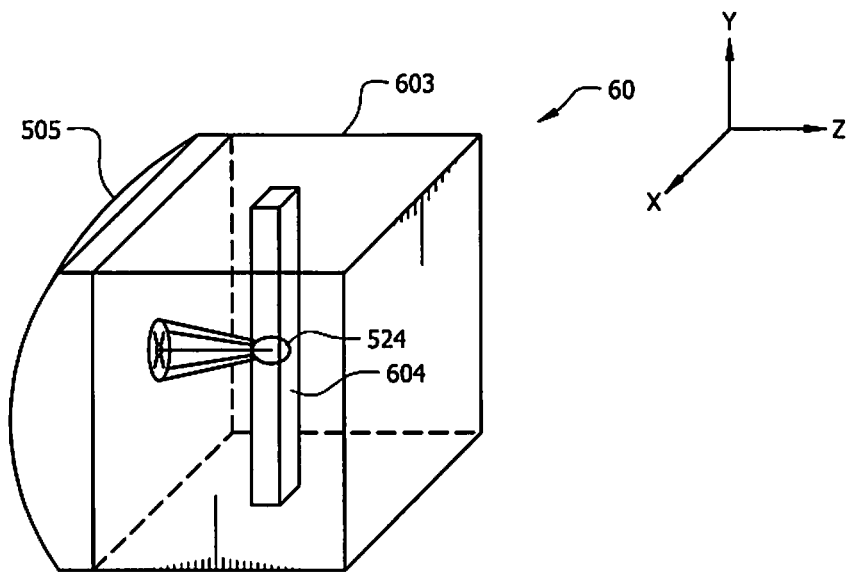

FIG. 5D depicts a perspective view of the cylindrical lens of the LD based optical subsystem coupled with the composite microscope objective in accordance with one aspect of the present disclosure.

Figure 5E:
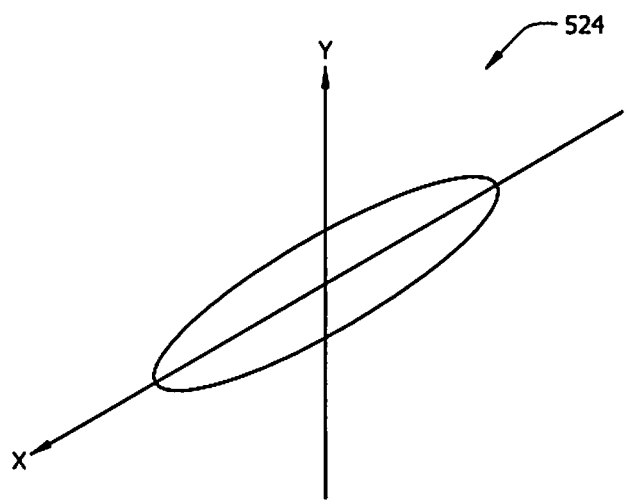

FIG. 5E depicts an enlarged view of the beam profile shown in FIG. 5D.

Figure 6:
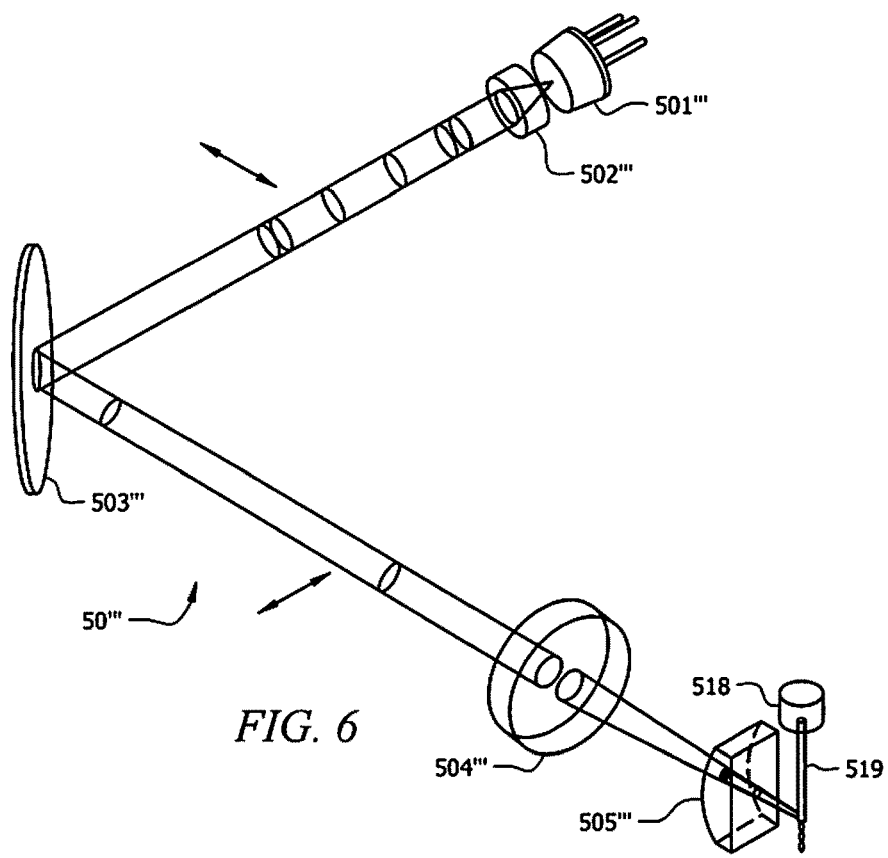

FIG. 6 is a perspective view of an alternative embodiment of a LD based optical illumination subsystem in accordance with one aspect of the present disclosure adapted for use in a flow cytometer system in which a jet stream of liquid passes through the viewing zone.

Figure 6A:
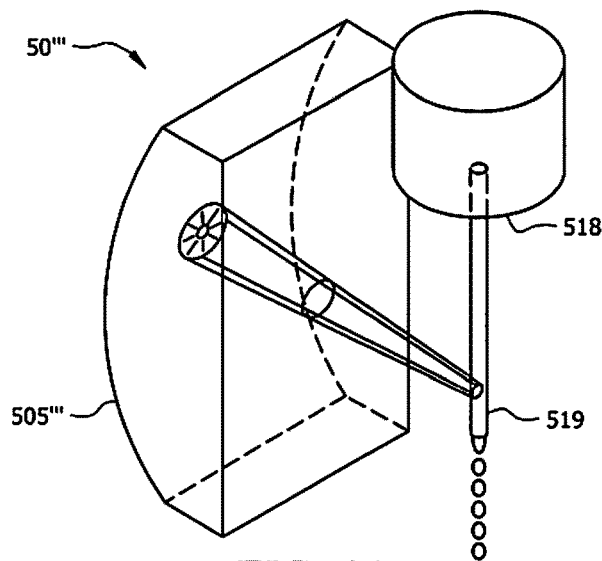

FIG. 6A is an enlarged perspective view of the alternative embodiment of a LD based optical illumination subsystem of FIG. 6 depicting in greater detail the jet stream of liquid passes through the viewing zone.

Figure 7:
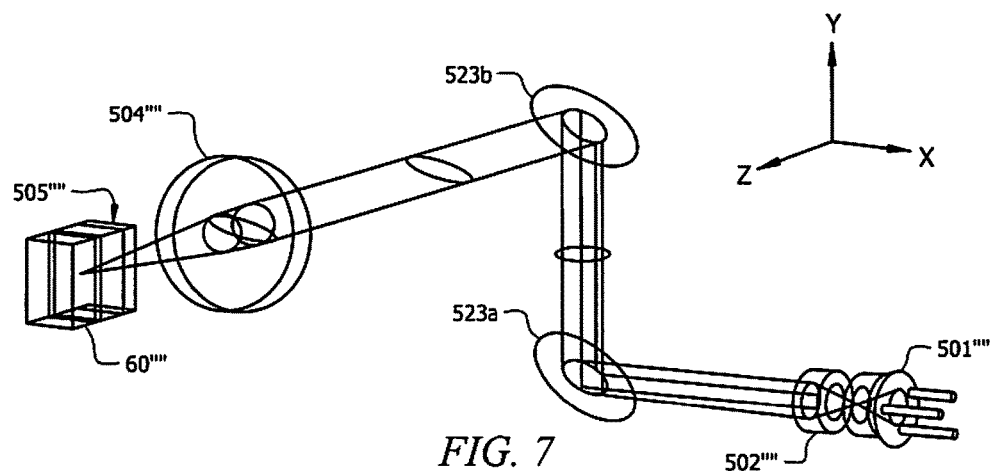

FIG. 7 is a perspective view of an alternative embodiment of a LD based optical illumination subsystem in accordance with one aspect of the present disclosure adapted for use in a flow cytometer system which orients the LD's slow axis parallel to the direction of liquid flowing through the fluid-passing channel of the composite microscope objective depicted in FIG. 1.

Figure 8:
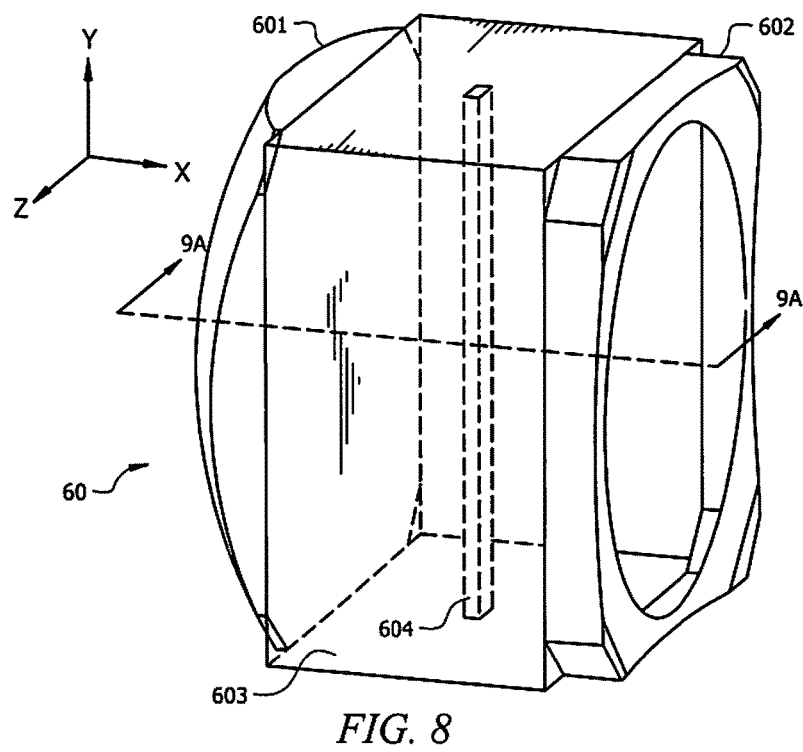

FIG. 8 is a perspective view of a composite microscope objective in accordance with one aspect of the present disclosure adapted for use in the flow cytometer system depicted in FIG. 1, the composite microscope objective having a fluid-passing channel formed therethrough with the particle illumination viewing zone located inside a cuvette therein.

Figure 8A:
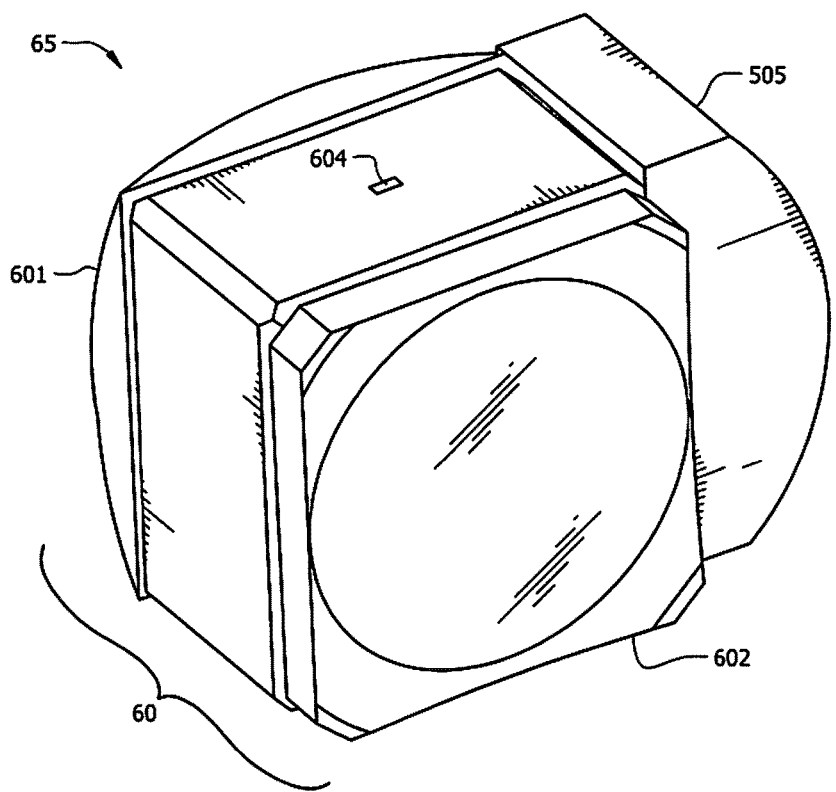

FIG. 8A is a perspective view of a combined microscope objective in accordance with one aspect of the present disclosure.

Figure 8B:
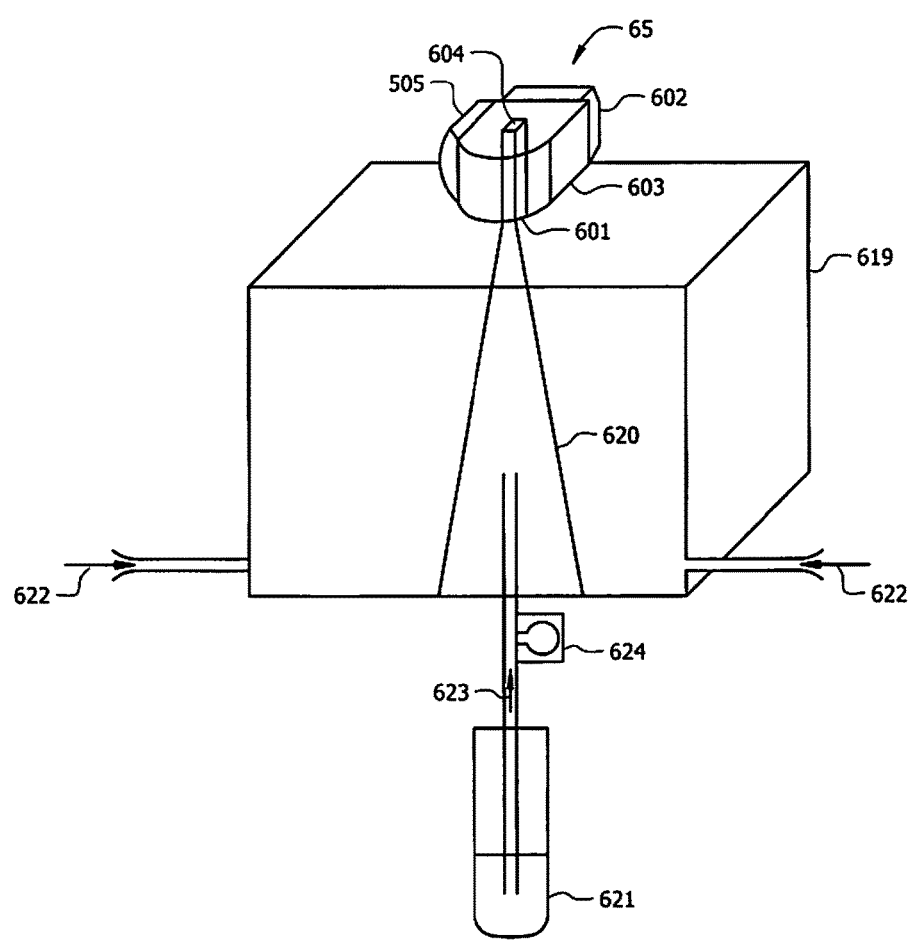

FIG. 8B illustrates the combined microscope objective depicted in FIG. 8A coupled with a flow cell in accordance with one aspect of the present disclosure.

FIG. 9A is a cross-sectional elevational view of the composite microscope objective taken along the line 9A-9A in FIG. 8 that includes ray traces from three (3) spatially separated locations in the viewing zone to an image plane for the objective illustrating scatter and fluorescence emission propagation.

FIGS. 9B1-9B3 are spot diagrams near the image plane depicted in FIG. 9A for the three (3) spatially separated light emission locations depicted in FIG. 9A.

Figure 10:
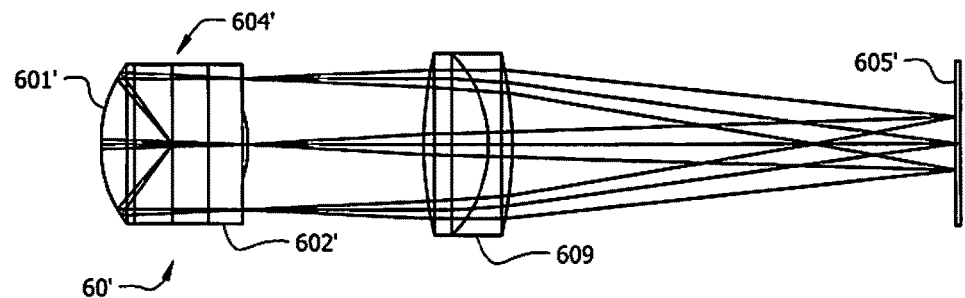

FIG. 10 is a cross-sectional elevational view similar to that of FIG. 9A for an alternative embodiment composite microscope objective in accordance with one aspect of the present disclosure that includes ray traces from three (3) spatially separated locations in a viewing zone therein to an image plane for the objective illustrating scatter and fluorescence emission propagation.

Figure 11:
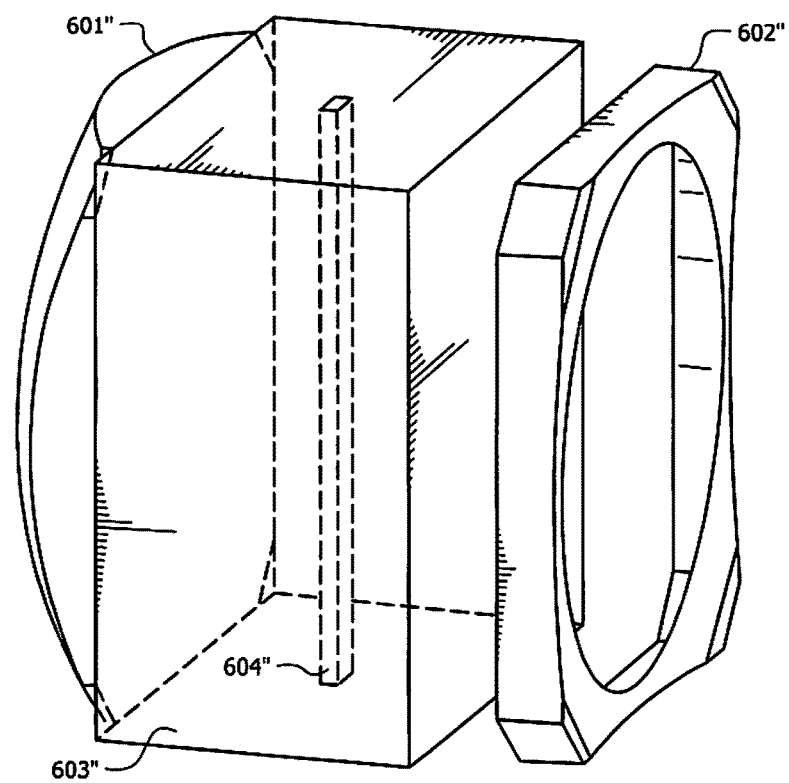

FIG. 11 is a perspective view of yet another alternative embodiment a composite microscope objective in accordance with one aspect of the present disclosure adapted for use in the flow cytometer system depicted in FIG. 1, the alternative embodiment composite microscope objective having a fluid-passing channel formed therethrough with the particle illumination viewing zone located inside a cuvette therein.

Figure 12:
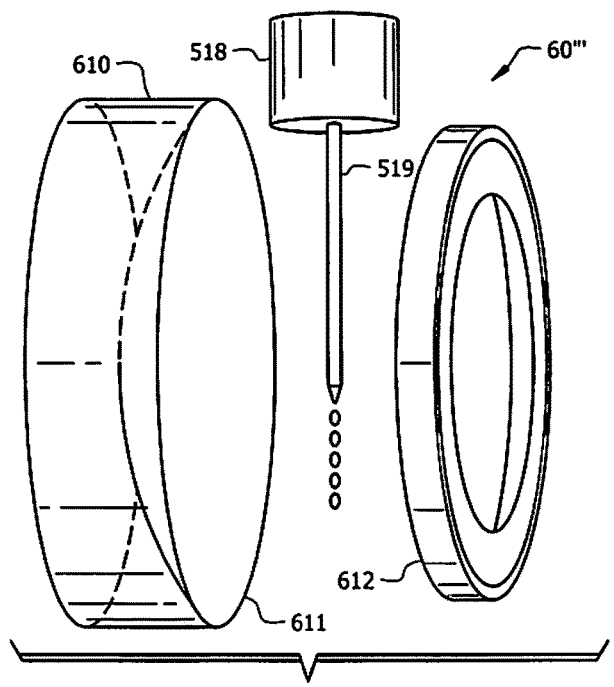

FIG. 12 is a perspective view of an embodiment of a composite microscope objective in accordance with one aspect of the present disclosure adapted for use in the flow cytometer system depicted in FIG. 1, adapted for use wherein a viewing zone is located inside the jet stream depicted in FIGS. 6 and 6A.

Figure 13:
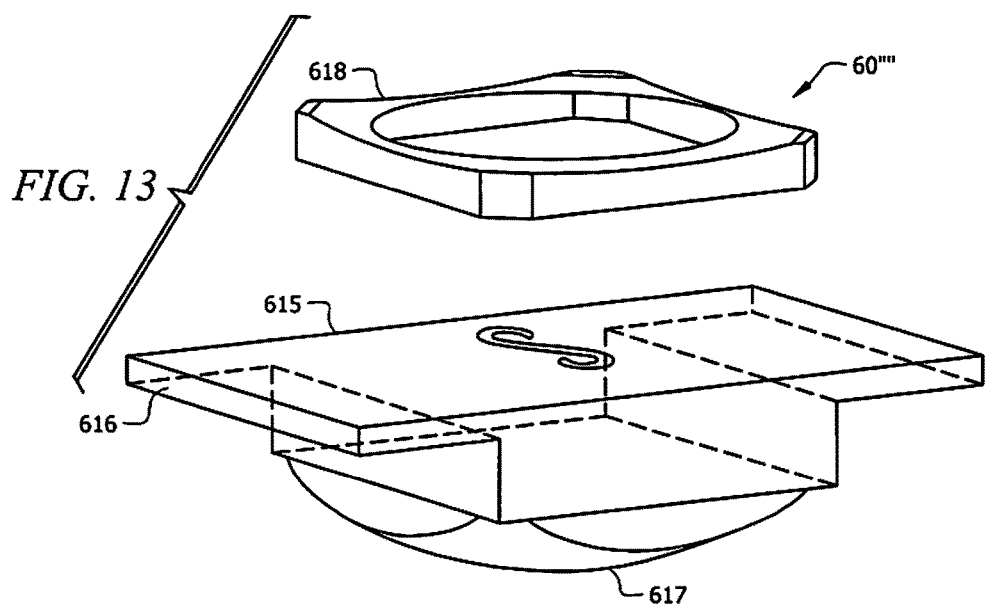

FIG. 13 is a perspective view of an embodiment of a composite microscope objective in accordance with one aspect of the present disclosure adapted for use wherein a viewing zone is located on the surface of a microscope slide.

Figure 14:
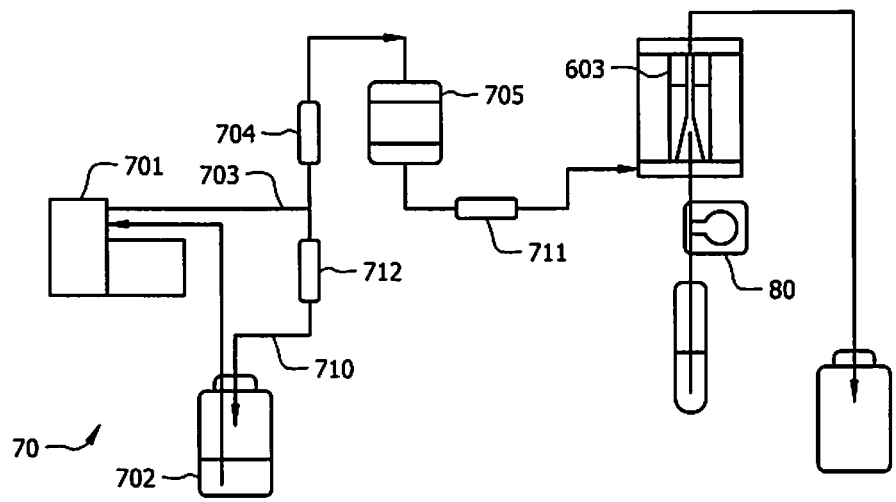

FIG. 14 is a schematic diagram depicting a fluidic system in accordance with one aspect of the present disclosure for supplying stable liquid sheath flow to a flow cytometer flow cell that includes:

1. a small capsule located between a sheath liquid pump and the flow cell; and 2. a particle filter located between the small capsule and the flow cell, both the particle filter and the small capsule providing air reservoirs for dampening pump pulsations.

Figure 15:
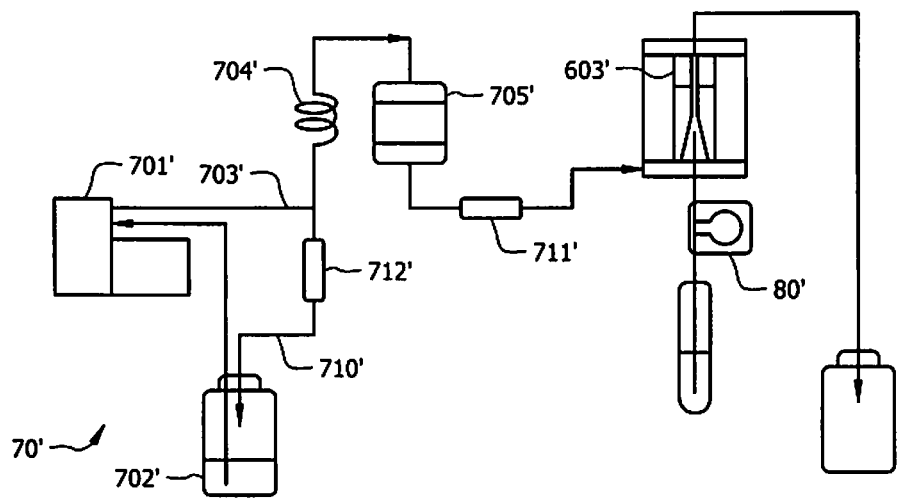

FIG. 15 is a schematic diagram depicting an embodiment of a fluidic subsystem similar to that illustrated in FIG. 14 that replaces the small capsule with a length of tubing for providing an air reservoir.

Figure 16A:
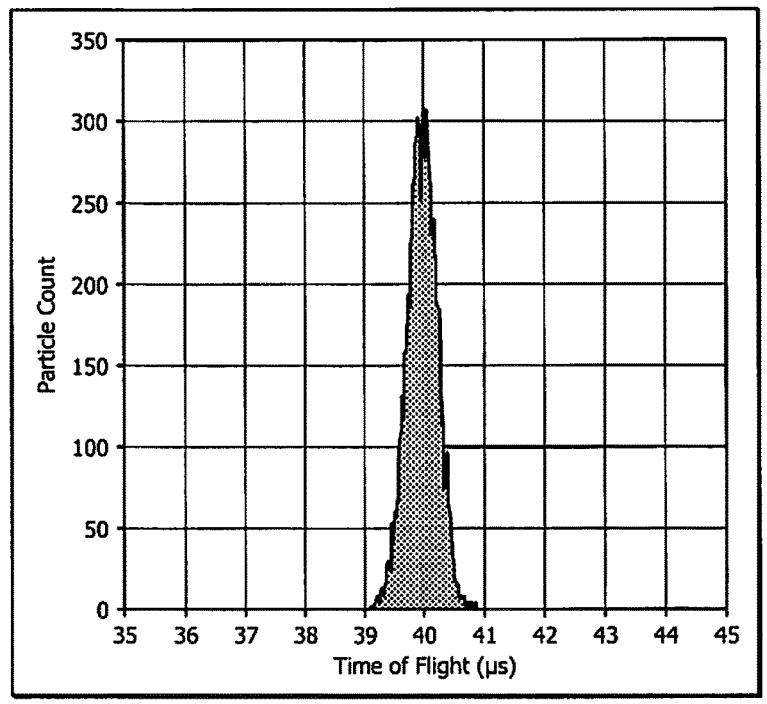
Figure 16B:
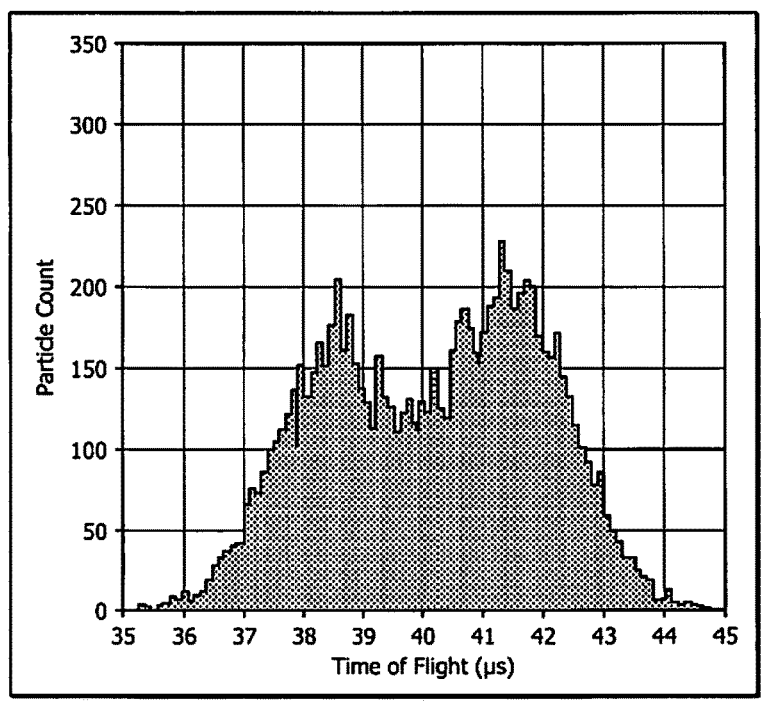

FIGS. 16A and 16B are histograms that compare measured particle flight times at the flow cell when the inlet portion of the particle filter has air trapped therein (FIG. 16A), and when there is no air within the fluidic subsystem between the sheath liquid pump and the flow cell (FIG. 16B).

Figure 17:
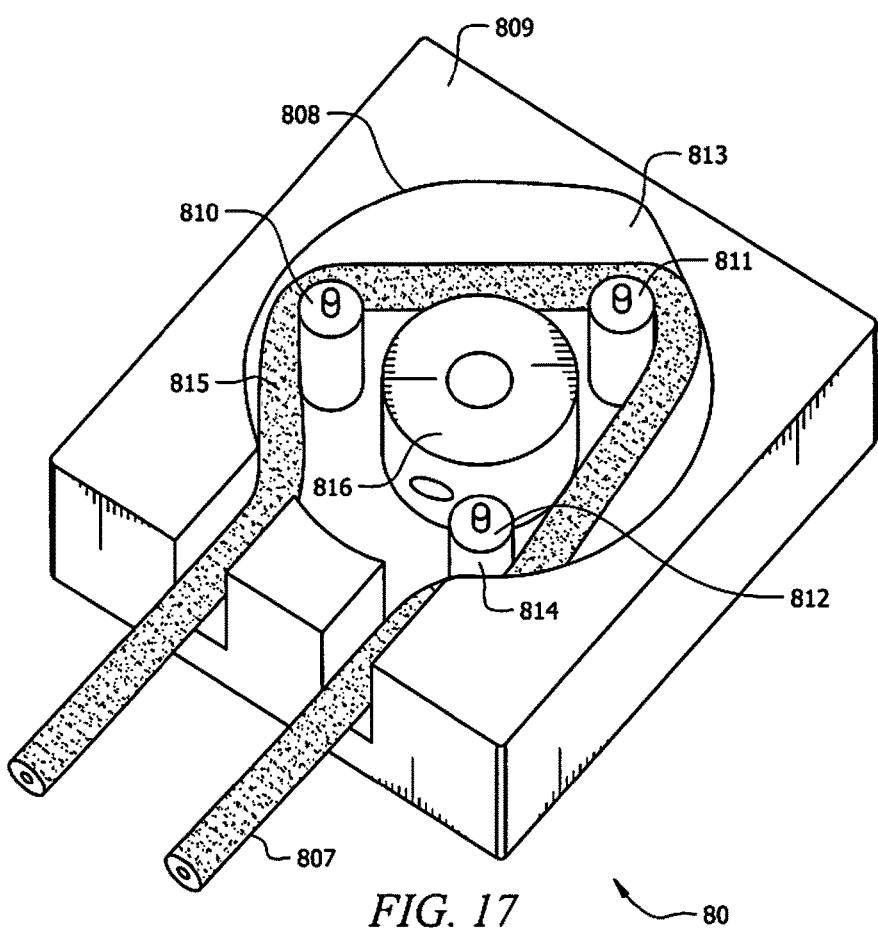

FIG. 17 is a perspective view of a 3-roller peristaltic pump in accordance with one aspect of the present disclosure depicting the pump's rollers, tube and surrounding pump housing.

FIGS. 18A through 18D depict simplified views for several states of the 3-roller peristaltic pump depicted in FIG. 17 with the rollers in different locations.

FIG. 19 is a detailed longitudinal cross-sectional view of the peristaltic pump's tube being partially compressed by the pump's roller.

FIGS. 19A and 19B are detailed cross-sectional views orthogonal to the peristaltic pump's tube's length taken along the lines 19A and 19B in FIG. 19 illustrating the tube's partial compression by the roller.

FIGS. 20A and 20B are schematic diagrams illustrating the pump's rollers and tube viewed along the pump's circular coordinates to depicting the pulseless flow provided by the peristaltic pump.

Figure 21:
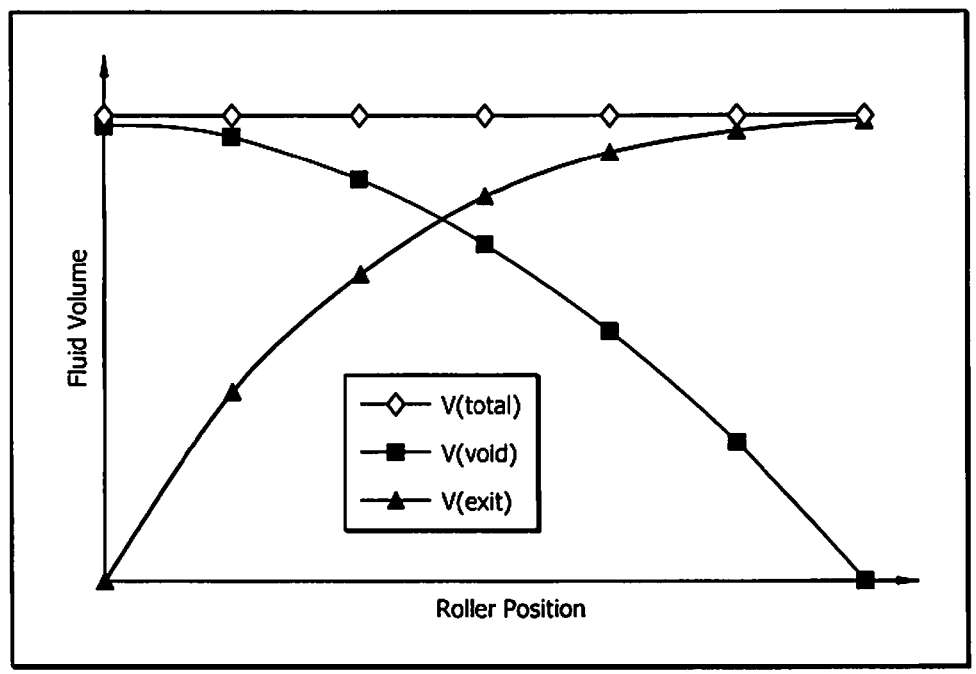

FIG. 21 is a graph depicting the functional relationship with respect to the roller position when it rolls off the exit section of the compressible tube of:
1. the total volume of liquid in the exit half of the pump; as well as
2. the liquid volumes in the pump's:
a. recess section; and
b. exit section.

Figure 22:
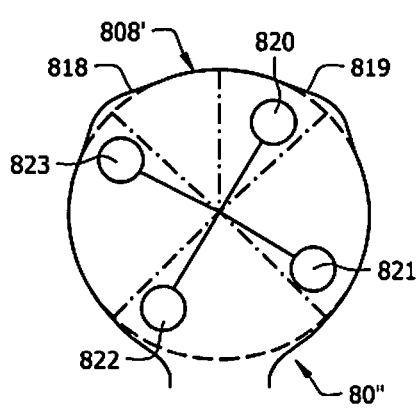

FIG. 22 is a simplified plan view of a 4-roller peristaltic pump in accordance with one aspect of the present disclosure.

Figure 23:
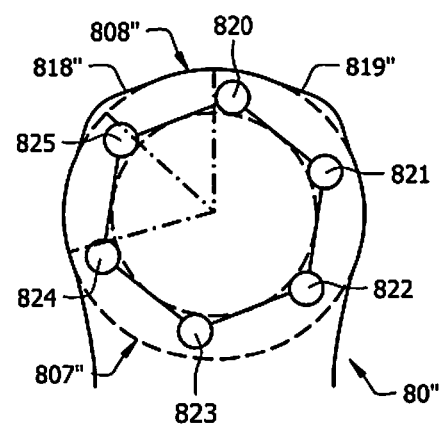

FIG. 23 is a simplified plan view of a 6-roller peristaltic pump in accordance with one aspect of the present disclosure.

Figure 24A:
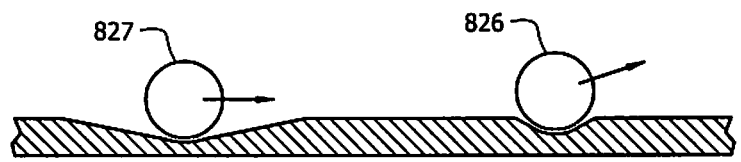

FIG. 24A is a longitudinal cross-sectional illustration of rollers and a compressible tube for a pulsation minimizing 3-roller peristaltic pump in accordance with one aspect of the present disclosure having a rotor with programmable speed.

Figure 24B:
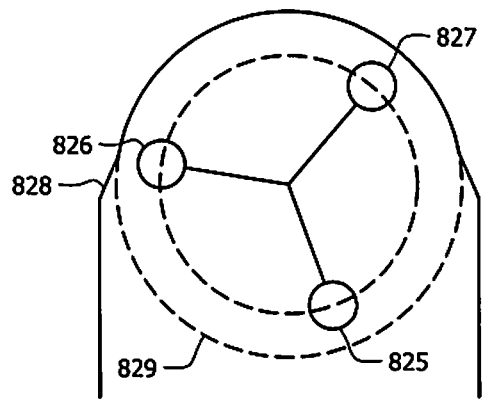

FIG. 24B is simplified plan view illustrating the pulsation minimizing 3-roller peristaltic pump in accordance with one aspect of the present disclosure having a rotor with programmable speed.

Figure 24C:
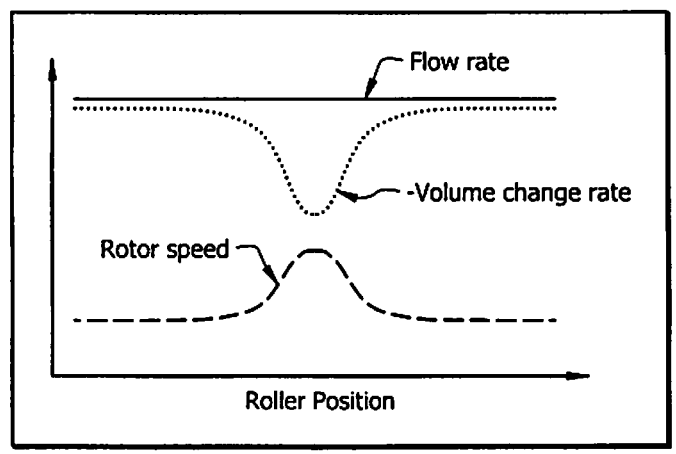

FIG. 24C is a graph depicting for the pulsation minimizing peristaltic pump depicted in FIG. 24B having a programmable speed rotor:
1. negative volume change rate with respect to the roller position;
2. rotor speed; and
3. pump flow rate.

Figure 25:
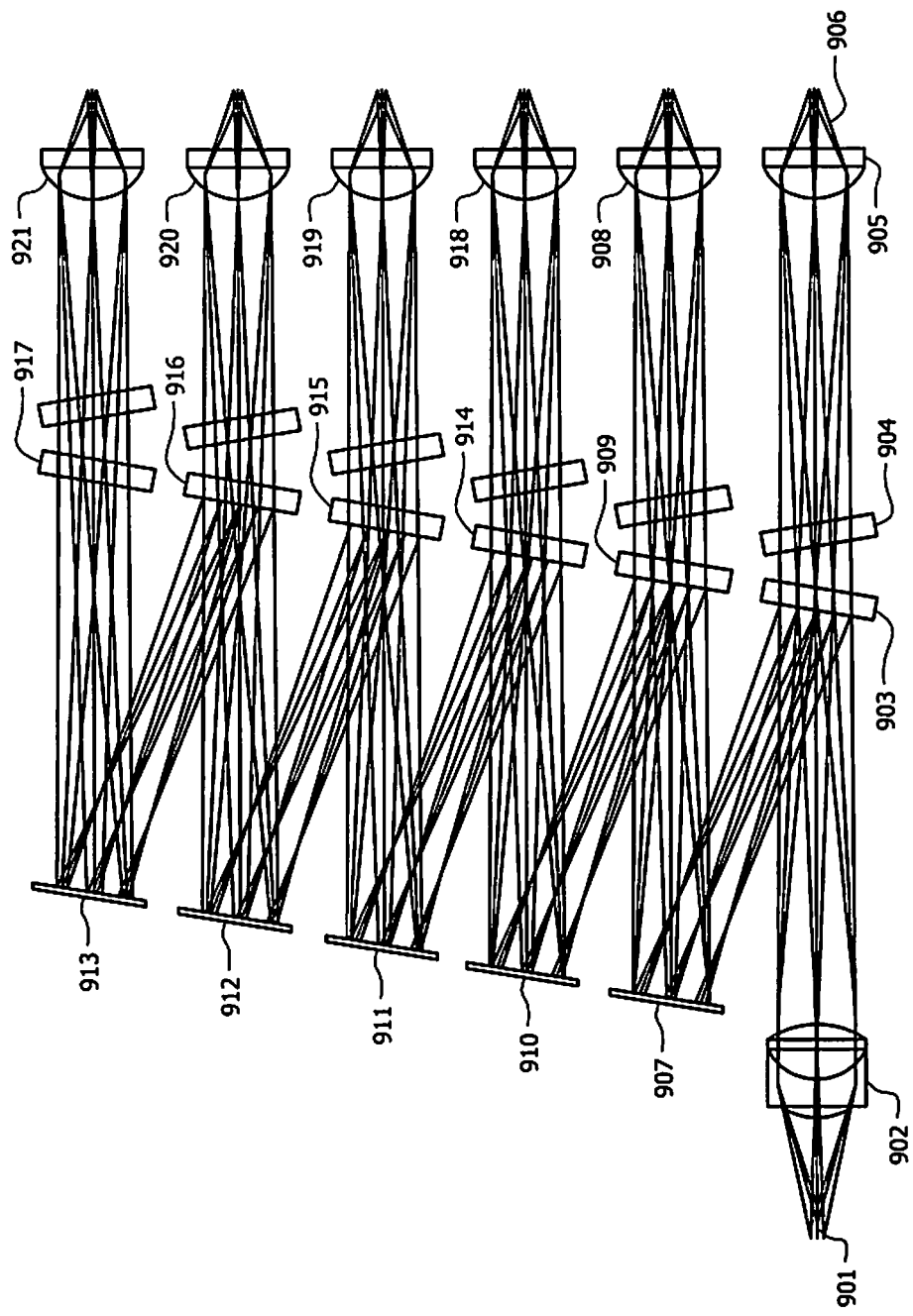

FIG. 25 is a diagram illustrating optical ray tracing for an exemplary 6 port wavelength division multiplexer ("WDM") using a zig-zag configuration in accordance with one aspect of the present disclosure.

Figure 25A:
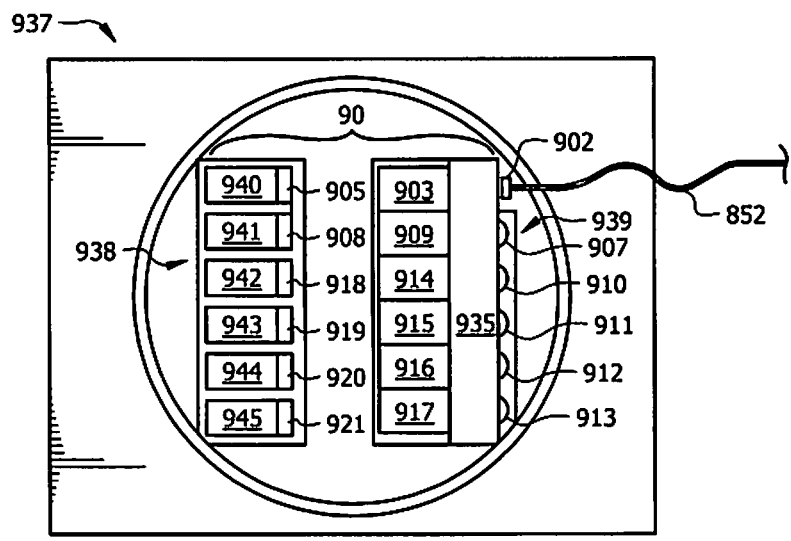

FIG. 25A illustrates a top view of a light detection assembly of the WDM illustrated in FIG. 25 in accordance with one aspect of the present disclosure.

Figure 25B:
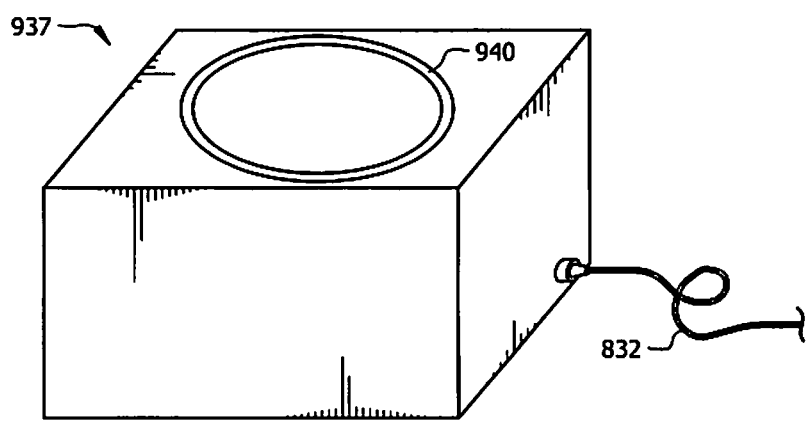

FIG. 25B illustrates a front perspective view of the light detection assembly of the WDM illustrated in FIGS. 25 and 25A.

Figure 26:
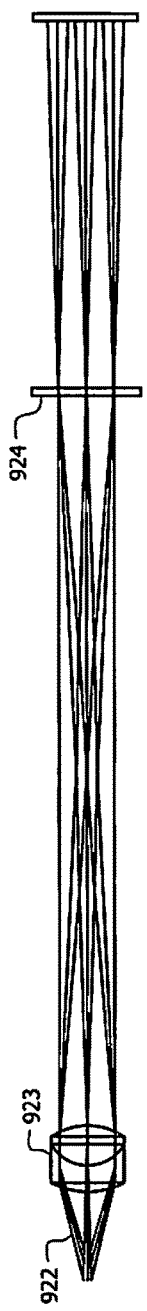

FIG. 26 is a diagram illustrating ray tracing of prior art collimating devices showing the device's limitation in collimating an extended light source.

Figure 27:
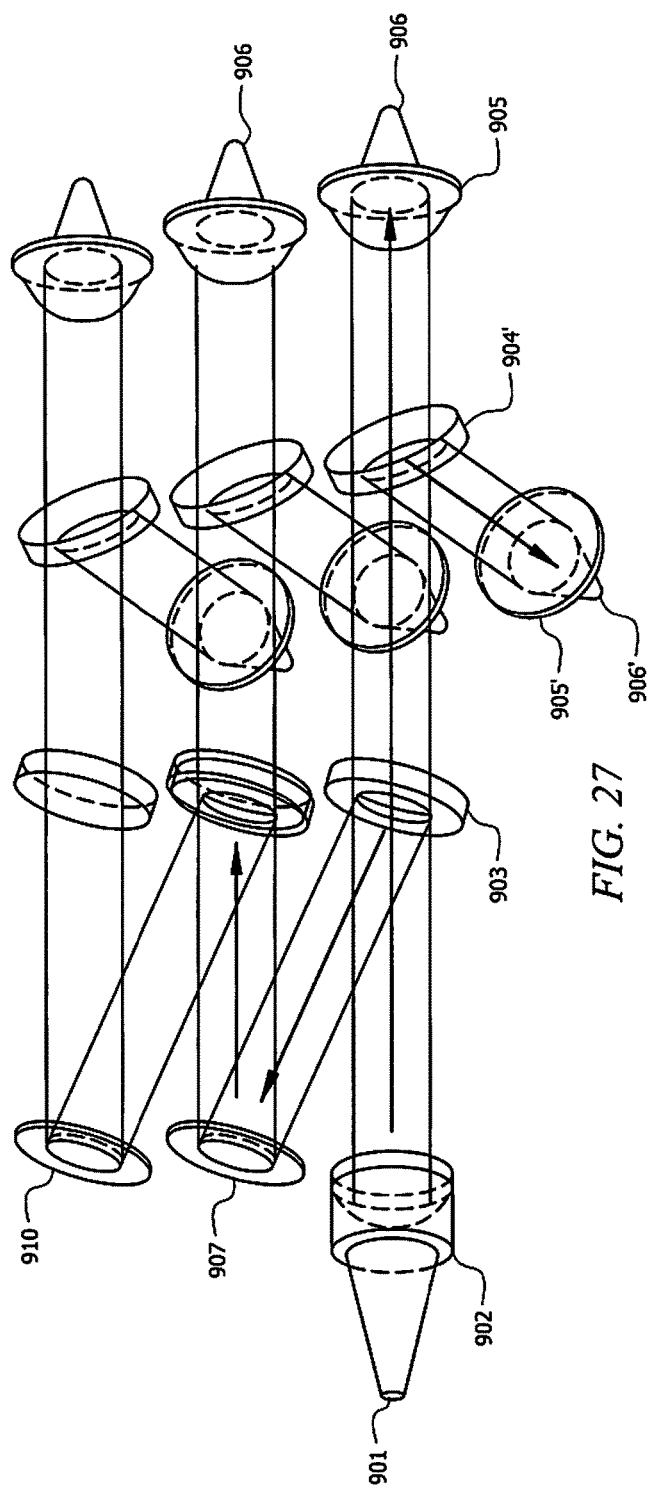

FIG. 27 is a perspective illustration of an embodiment of a 6 port WDM using a combination of zig-zag and branched configurations in accordance with one aspect of the present disclosure.

Figure 28:
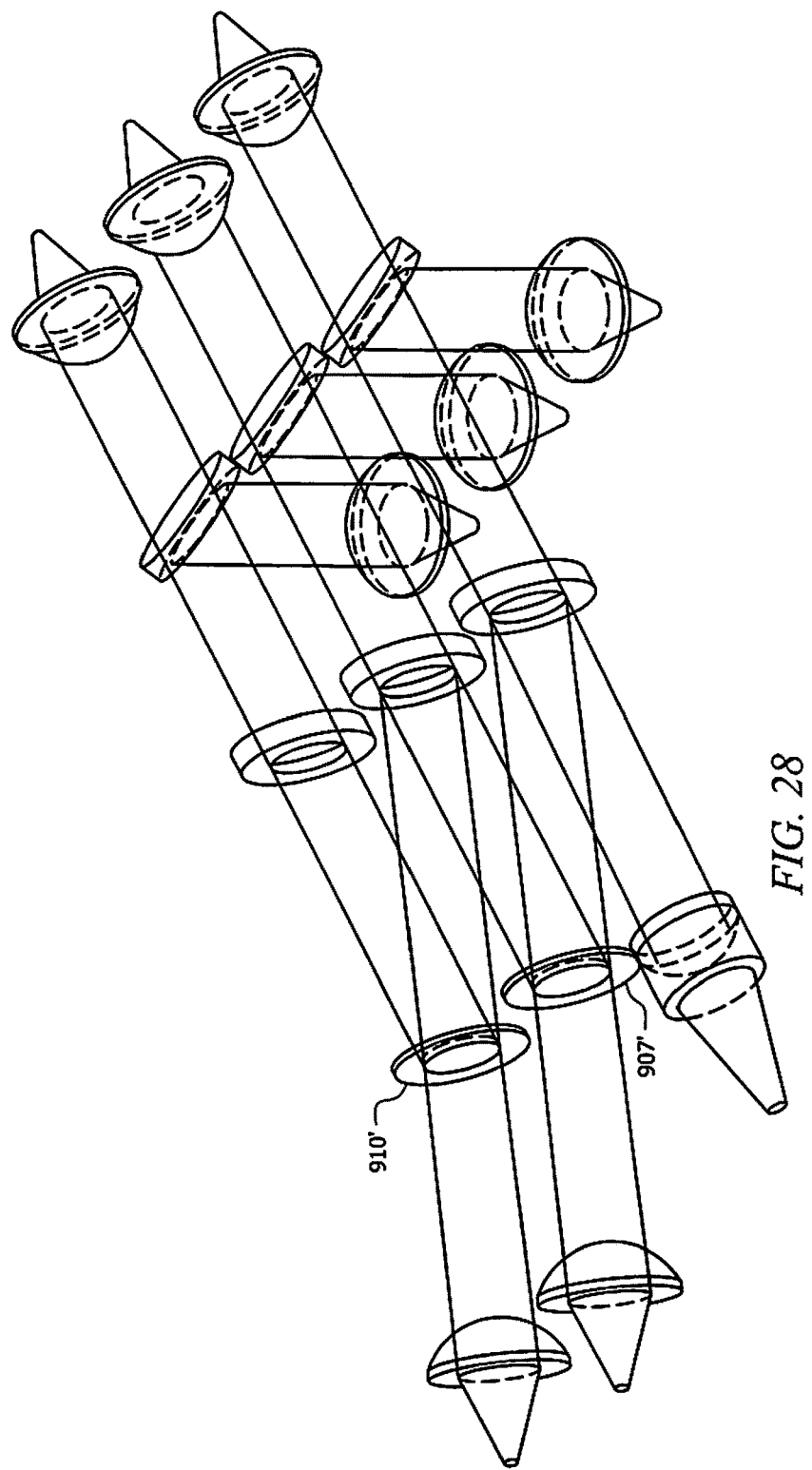

FIG. 28 is a perspective illustration of another embodiment of a WDM having concave dichroic filters in accordance with one aspect of the present disclosure.

Figure 29A:
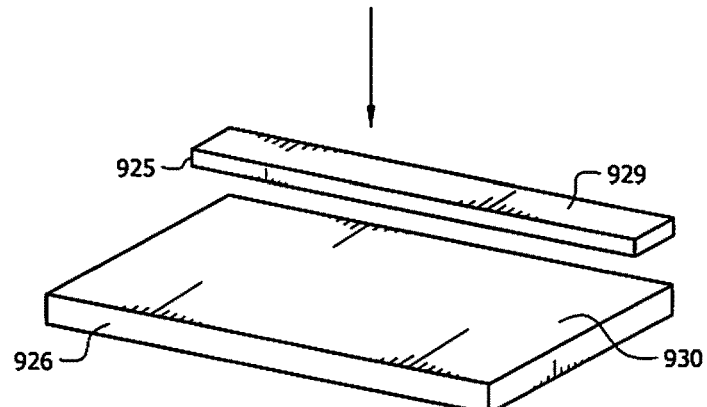
Figure 29B:
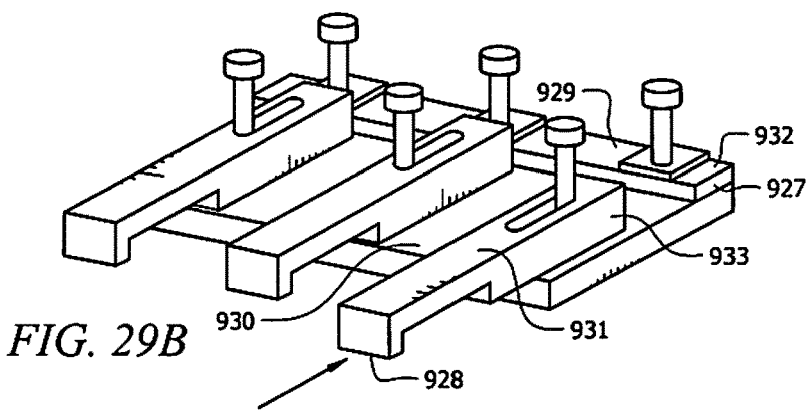

FIGS. 29A and 29B are perspective illustrations depicting an assembly process for constructing a replaceable dichroic filter assembly for a reconfigurable WDM in accordance with the present disclosure.

Figure 29C:
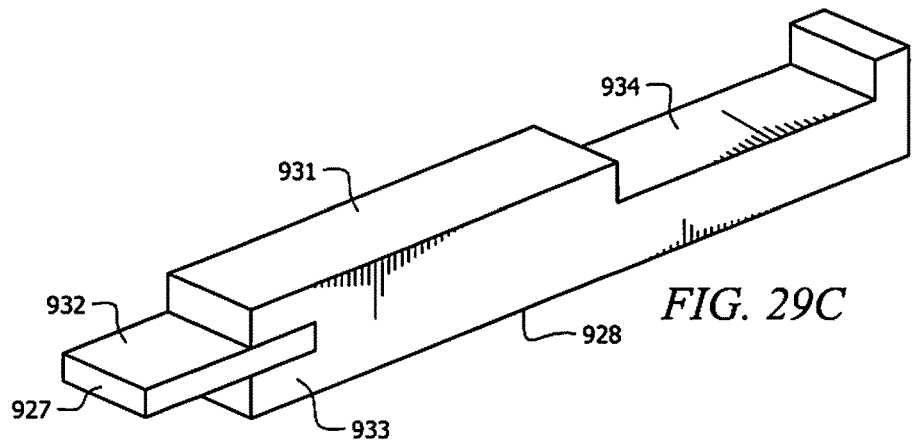

FIG. 29C is a perspective illustration of a replaceable dichroic filter assembly build in accordance with the illustrations of FIGS. 29A and 29B.

Figure 30A:
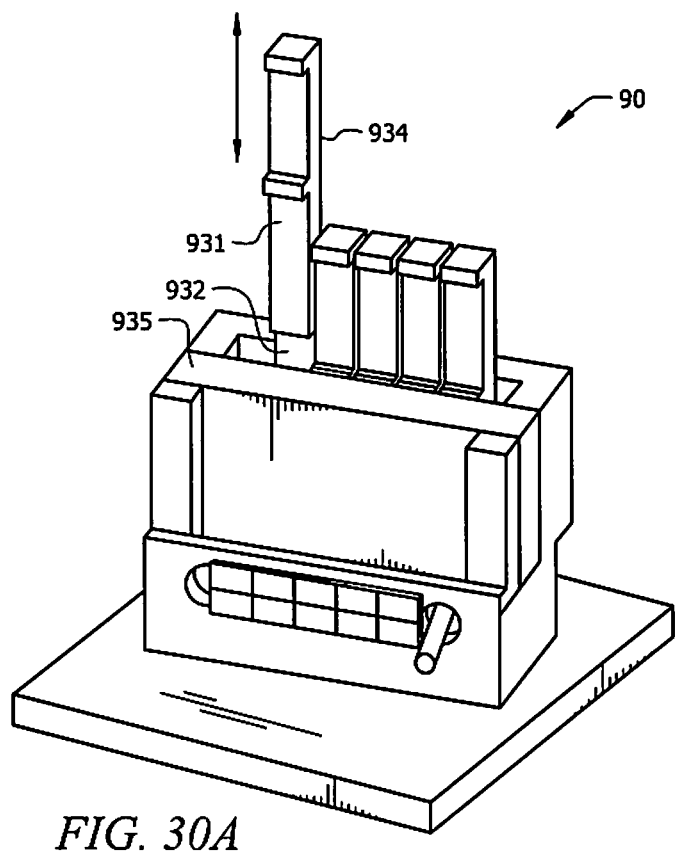
Figure 30B:
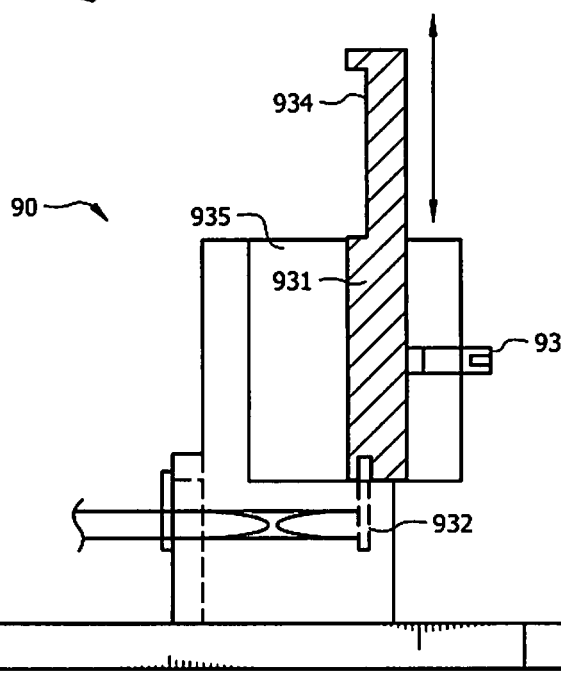

FIGS. 30A and 30B are perspective illustrations of a WDM in accordance with one aspect of the present disclosure depicting installing into the WDM the replaceable dichroic filter assembly depicted in FIG. 29C and its removal therefrom.

Figure 31:
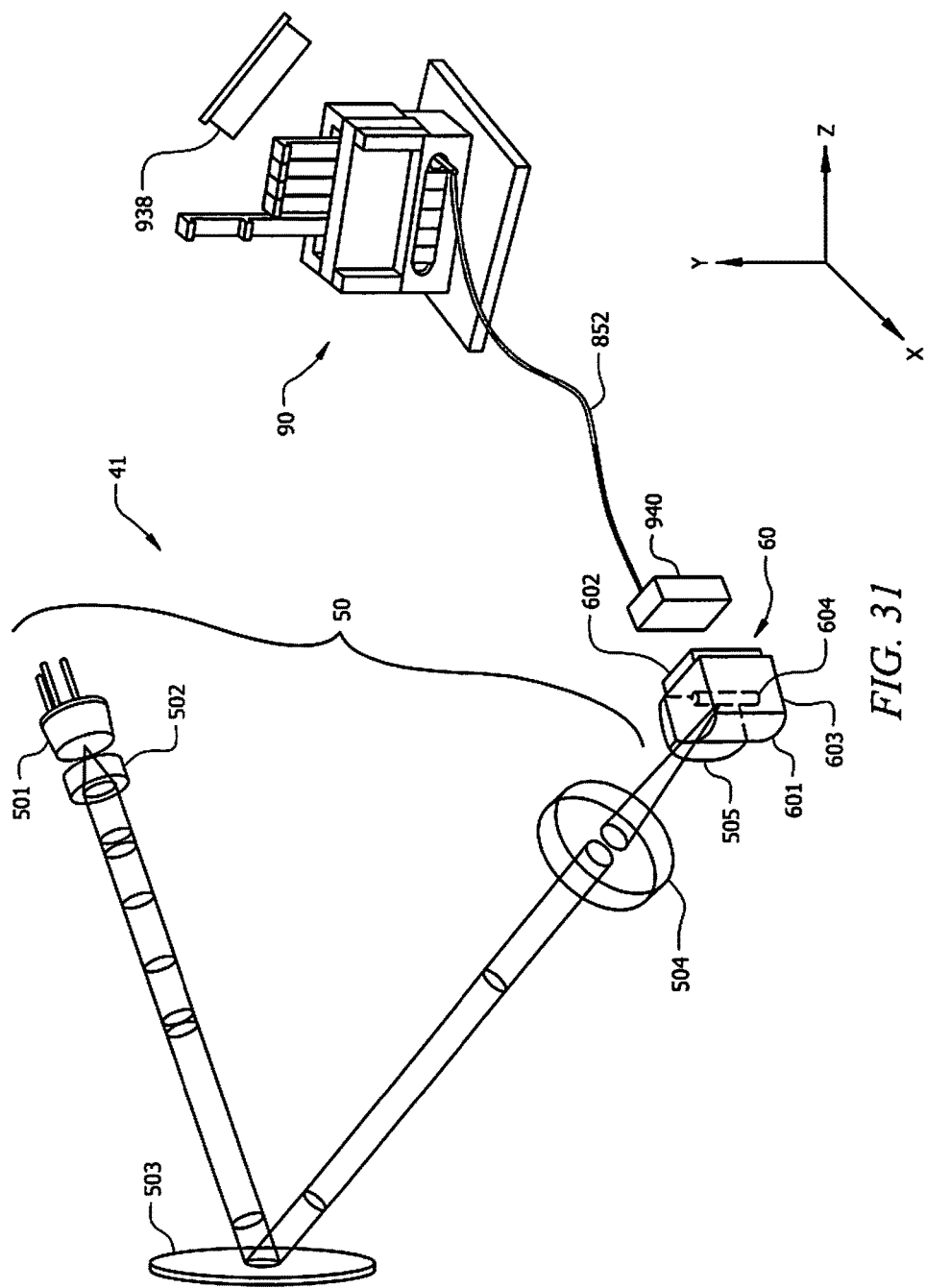

FIG. 31 is a diagram schematically illustrating an optical system with a single light source in accordance with one aspect of the present disclosure.

Figure 32:
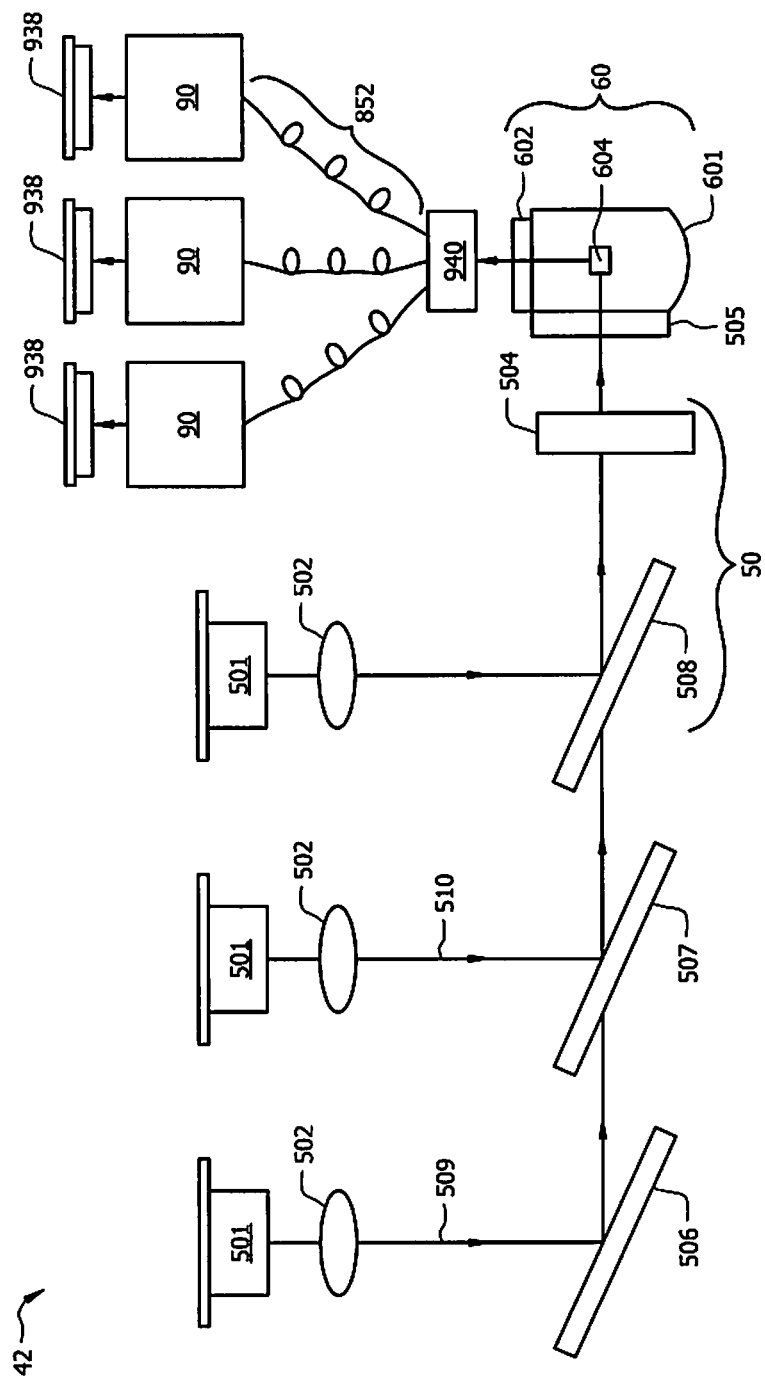

FIG. 32 is a diagram schematically illustrating an optical system with multiple light sources in accordance with one aspect of the present disclosure.

Figure 33:
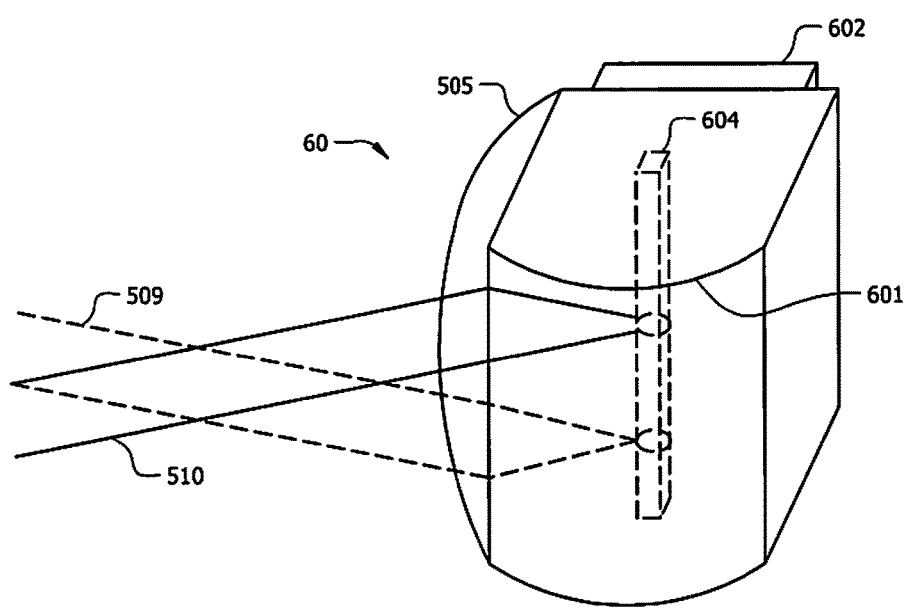

FIG. 33 illustrates an enlarged view of beams of light shown in FIG. 32.

Figure 34:
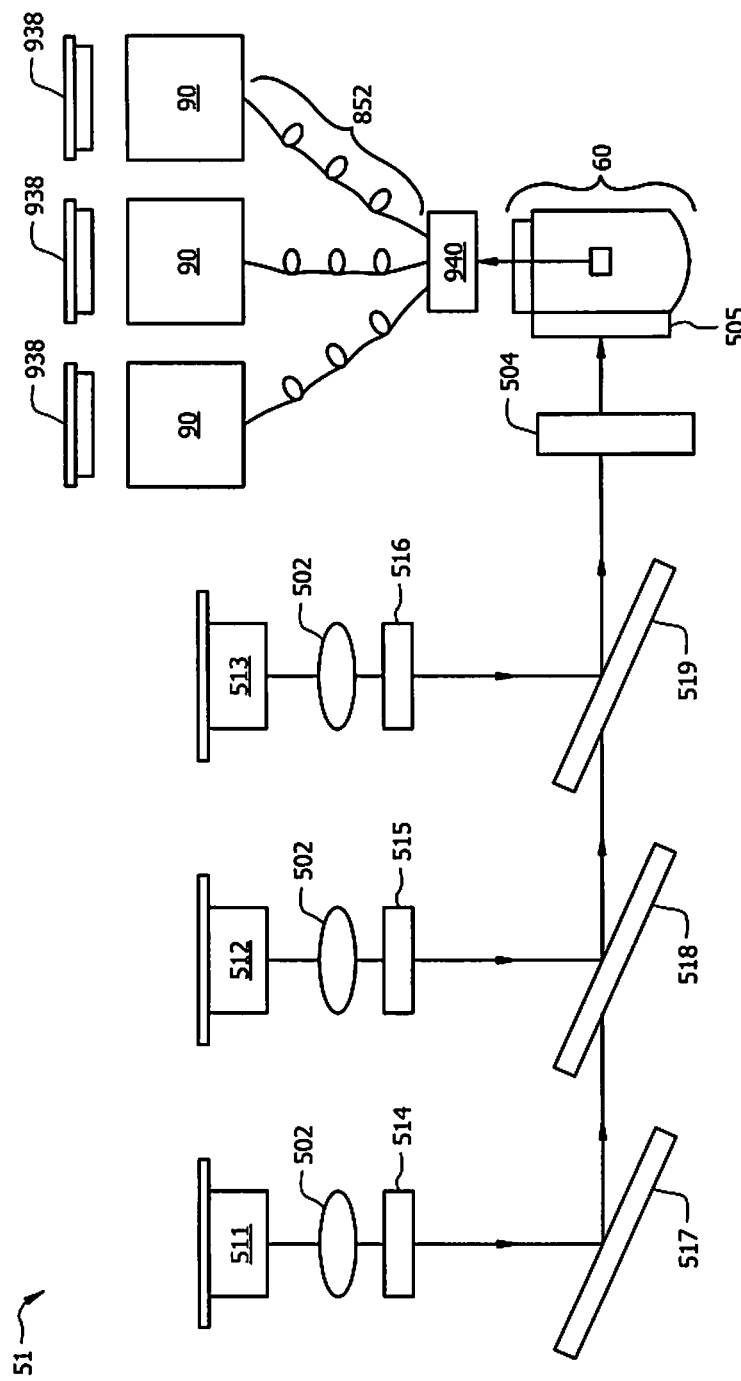

FIG. 34 is a diagram schematically illustrating an optical system with chromatic compensation elements in accordance with one aspect of the present disclosure.

Figure 35:
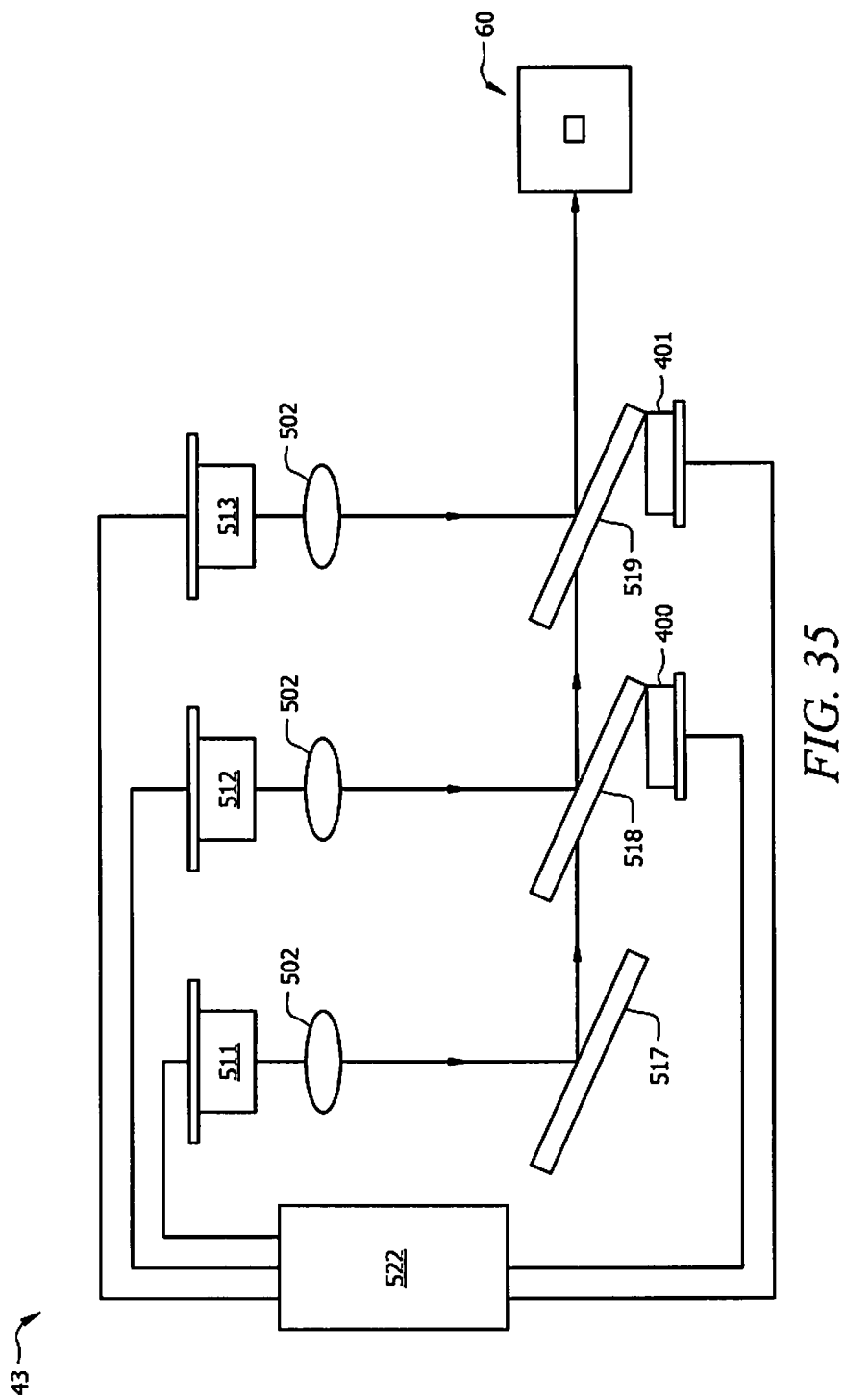

FIG. 35 is a diagram schematically illustrating a power monitoring system in accordance with one aspect of the present disclosure.

Figure 36:
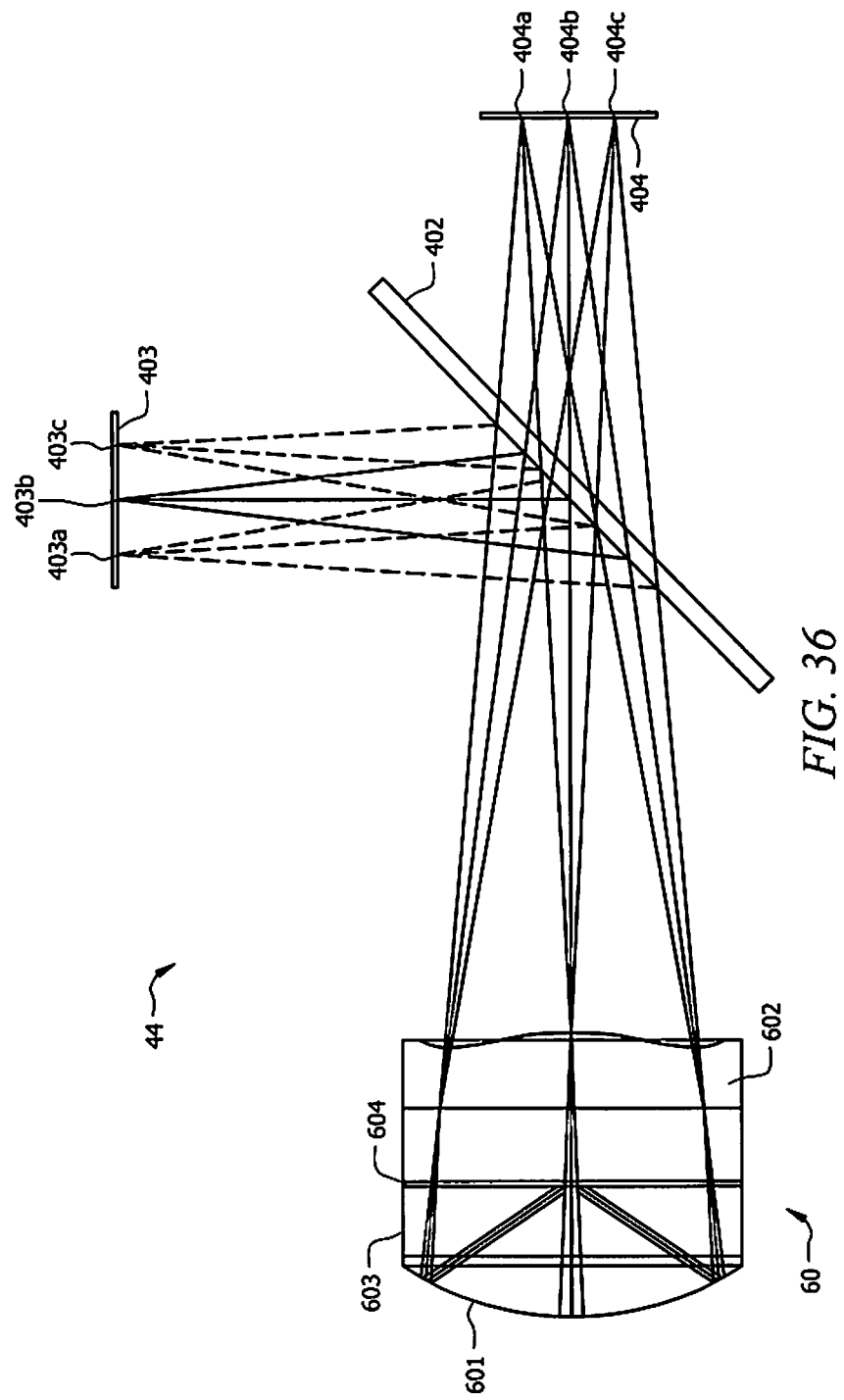

FIG. 36 is a diagram schematically illustrating an optical system in accordance with one aspect of the present disclosure.

Figure 37:
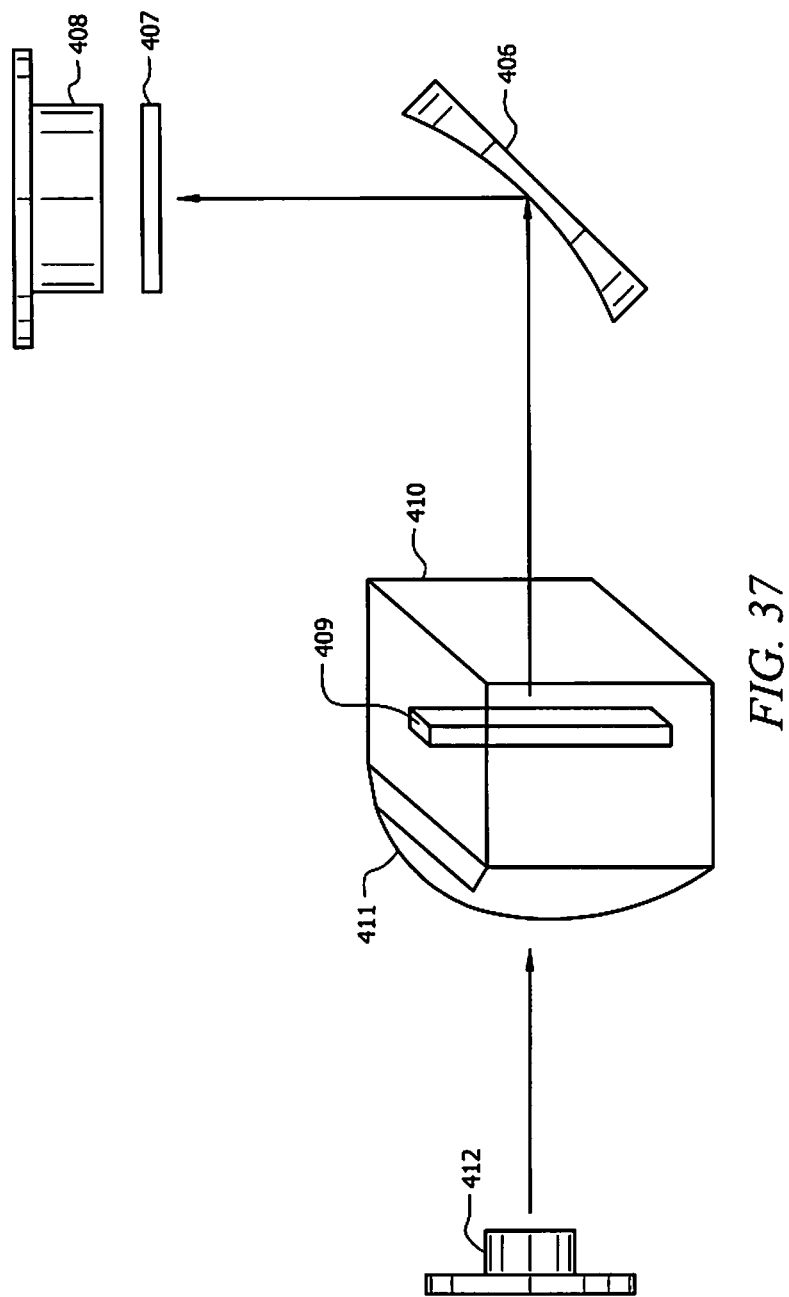

FIG. 37 is a diagram schematically illustrating an axial light loss detection system in accordance with one aspect of the present disclosure.

FIG. 38 is a diagram schematically illustrating an axial light loss detection system coupled with a second light detection system in accordance with one aspect of the present disclosure.

DETAILED DESCRIPTION

Flow Cytometer

A flow cytometer system may include one or more following components.

1. A flow cell through which a liquid stream, usually called a sheath flow, carries and hydrodynamically aligns cells or particles so that they pass single file through the flow cell.

2. A measuring subsystem system coupled to the flow cell that detects cells or particles passing through the flow cell and is usually either:

a. an impedance or conductivity measuring subsystem; or b. an optical illumination subsystem together with an optical sensing subsystem.

3. A conversion subsystem for converting the output signal from the measuring subsystem into computer processable data.

4. A computer for analyzing the data produced by the conversion subsystem.

The optical illumination subsystem provides a collimated and then focused beam of light, usually laser light of a single wavelength, that impinges upon the hydrodynamically-focused stream of liquid passing through the flow cell. Accordingly, the flow cytometer system may have one or more light sources that may include:

1. one or more lamps, e.g., mercury or xenon;
2. one or more high-power water-cooled lasers, e.g., argon, krypton or dye laser;
3. one or more low-power air-cooled lasers, e.g., argon (488 nm), HeNe (red-633 nm), HeNe (green) and HeCd (UV); and/or
4. one or more diode lasers (blue, green, red and violet).

The optical sensing subsystem includes one or more detectors aimed where the focused liquid stream passes through the light beam. Such detectors may include:

1. detectors in line with the light beam (Forward Scatter or FSC);
2. detectors perpendicular to it (Side Scatter or SSC); and
3. fluorescence detectors.

Each suspended particle passing through the beam scatters the light, and fluorescent material present in the particle or attached to the particle excited by the impinging light emit light at a longer wavelength than that of the impinging light.

Detecting and analyzing brightness changes in a combination of scattered and fluorescent light at each detector (one for each fluorescent emission peak) permits deriving various types of information about the physical and chemical structure of each individual particle. FSC correlates with cell volume. Due to light being scattered off of internal components within a cell, SSC depends on the inner complexity of the particle (i.e., shape of the nucleus, the amount and type of cytoplasmic granules or the membrane roughness). Some flow cytometers omit a fluorescence detector and detect only scattered light. Other flow cytometers form images of each cell's fluorescence, scattered light, and transmitted light. The flow cytometer system's conversion subsystem, which may include one or more amplifiers which may be either linear or logarithmic, generally includes one or more Analogue-to-Digital Converters ("ADCs") for converting the measuring subsystem's output signal into data that is then processed by the computer.

Modern flow cytometers usually include up to four (4) lasers and numerous fluorescence detectors. Increasing the number of lasers and detectors permits labeling cells with several different antibodies, and can more precisely identify a target population by their phenotypic markers. Some instruments can even capture digital images of individual cells, allowing for the analysis of a fluorescent signal location within or on the surface of cells.

FIG. 1 depicts a flow cytometer in accordance with one aspect of the present disclosure identified by the general reference number 40. The flow cytometer 40 may include:

1. a LD based optical subsystem 50;
2. a composite microscope objective 60;
3. a fluidic subsystem 70 for supplying a liquid sheath flow;
4. a peristaltic pump 80 for injecting a liquid sample flow that contains particles to be analyzed into the liquid sheath flow supplied by the fluidic subsystem 70, the liquid sample flow becoming hydrodynamically focused by the liquid sheath flow passes through a viewing zone with the composite microscope objective 60 gathering and imaging light scattered and/or fluoresced by particles in the viewing zone;

5. an optical fiber 852 that receives light scattered and/or fluoresced by particles in the viewing zone that the composite microscope objective 60 gathers and images;

6. a wavelength division multiplexer 90 ("WDM 90") for optically processing scattered and/or fluoresced light received from the optical fiber 852; and 7. a photodetector system 938 to detect the light processed by the WDM 90.

Optical Subsystem 50

In most of the instruments, particles of interest, such as blood cells or microspheres, are carried by the sheath flow using hydrodynamic focusing into a viewing zone inside a cuvette or jet stream and illuminated there by a focused laser beam. The technique provides the means to accurately identify and count particles of interest without being overwhelmed by background noise occurring outside a registration time window (Practical Flow Cytometry, Howard M. Shapiro, Wiley (2003) ISBN 0471411256). To increase detection sensitivity, the cross section of the focused laser beam is usually elliptical, with the minor axis along the direction of flow. In order to maintain the threshold integrity, the laser profile must have a smooth or bell shaped profile along the flow direction. One common method for producing such an beam is to elongate a 5 nearly collimated circular Gaussian beam along the direction of flow with a beam expander made of either prism or cylindrical lens pair, then focus the beam down with a spherical lens. Since the shape of the beam at the focus is the spatial Fourier transform of the beam at far field, this produces a Gaussian shaped elliptical spot with minor axis along the flow.

Conventional lasers are expensive, bulky and power hungry. More recently, laser diodes ("LD") have become available. Differing from conventional lasers, the new generation of LDs is cost effective, compact and power efficient, and shows great promise for new generation of compact biomedical instruments. A LD emits light having an elliptical cross-section with the ellipse's major axis, frequently called the fast axis, perpendicular to the LD's junction, and the ellipse's minor axis, frequently called the slow axis, parallel to the LD's junction. Unfortunately, the beam quality of a typical LD, particularly along its fast axis, leaves much to be desired, preventing its wide acceptance in flow cytometric applications.

In principle, the quality of the LD beam can be significantly improved by spatial filtering. If a small pinhole or a single mode optical fiber is positioned at the focal point of a lens, such that it only accepts the lowest order spatial mode, the beam passing through the pinhole or single mode optical fiber will be of nearly perfect Gaussian shape. U.S. Pat. No. 5,788,927 discloses that such a beam can then be collimated and expanded in the direction of flow through the cytometer, and finally focused down to an elliptical shaped Gaussian beam with minor axis along the flow direction. Unfortunately, the size of desktop instrumentation limits the diameter of a pinhole to less than 5 micron. The core size of a visible wavelength single mode optical fiber also has a similar dimension. The challenge to manufacture such a precision spatial filter and maintain its long-term stability not only increases the cost of LD based laser system, but also reduces its reliability.

More recently, in an effort to reduce the possible side lobes due to the edge effect of limited numerical aperture of collimating lens, U.S. Pat. No. 6,713,019 ("the '019 patent") discloses rotating the LD by ninety degrees)(90°) such that its slow axis is parallel to the direction of flow. A beam diffusing section, such as a concave cylindrical lens, is then introduced to diffuse the collimated beam in the direction perpendicular to the flow, followed by a beam spot forming section, such as a spherical focusing lens, to form an elliptical spot within the cytometer's particle viewing zone. As described in detail in the '019 patent, the laser beam after the spot forming section is extremely astigmatic. In particular, the width of the beam at the viewing zone in the direction perpendicular to the flow is comparable or even wider than the width of the flow channel. This not only reduces the amount of laser energy impinging upon the particle and consequently the signal intensity, but also increases undesired background scattering from the liquid-flow cell interface. Instead of rotating the LD, U.S. Pat. Nos. 7,385,682 and 7,561,267 disclose using a large numerical aperture aspheric lens for LD collimation. Such a design, however, cannot correct the fringe effect inherent in the LD's beam profile. Consequently, there presently exists a need for a simple LD based optical system for use in flow cytometers that can reliably produce a focused elliptical beam with near Gaussian shape along its minor axis and a width along major axis.

In accordance with one aspect of the present disclosure, the optical subsystem 50 may include a LD 501 that, as depicted in greater detail in FIG. 2, emits a diverging beam of light from an edge thereof. As more graphically depicted in FIGS. 2 and 2A, the diverging beam of light has an elliptically shaped cross-sectional profile with both a major axis, a.k.a. the fast axis, and a minor axis, a.k.a. the slow axis. The diverging beam of light emitted from the LD 501 may impinge upon a collimating lens 502 which converts the diverging beam of light emitted by LD 501 into a collimated beam of light having an elliptical cross-section. Although not essential, the optical subsystem 50 may also include an optional mirror 503 positioned to direct the collimated elliptical beam of light towards the composite microscope objective 60. A plano-convex lens 504, positioned near the composite microscope objective 60, may reduce the major axis of the elliptically shaped beam of light that is oriented perpendicular to the direction in which the liquid sample and the surrounding liquid sheath flow through the viewing zone within the composite microscope objective 60. At the viewing zone, the width of the elliptically shaped beam of light:

1. perpendicular to the direction in which the liquid sample flow passes through the viewing zone may be slightly less than the width of the liquid sheath flow; while 2. still sufficiently wide so particles in the sample flow pass through a nearly flat portion of the elliptically shaped beam of light at the beam's maximum intensity.

In accordance with one aspect of the present disclosure, it is apparent to those skilled in the art that the plano-convex lens 504 may be replaced by other types of optical elements such as an achromatic doublet lens or combination of spherical lenses, cylindrical lenses, and/or prism pairs. Alternatively, the mirror 503 and the lens 504 may also be replaced by a concave mirror. For polarization sensitive applications of the flow cytometer 40, an optional polarization conditioning element, such as a half-wave plate, may also be placed in the collimated section of the beam of light extending from the collimating lens 502 to the lens 504. Finally, before passing through the viewing zone the beam of light may pass through a high power cylindrical lens 505, positioned adjacent to the viewing zone. As depicted in FIG. 1, the axis of the cylindrical lens 505 is oriented perpendicular to the direction in which the liquid sample flow passes through the viewing zone, and the focal length of the cylindrical lens 505 produces a tight focusing of the beam of light's minor axis at the viewing zone.

An advantage of the optical subsystem 50 in comparison with conventional LD based optical subsystem may be discerned more clearly in FIGS. 2 and 2A. Most commercially available laser diodes suitable for use in a flow cytometer emit a beam of light from an edge thereof. As depicted in FIG. 2, a gain section 509 of such a LD chip 510 is highly confined in the transverse direction indicated by an arrow 511. Consequently, to achieve high output power LD manufacturers often sacrifice beam quality, particularly along the transverse or fast axis direction that is oriented parallel to the arrow 511. FIG. 2A shows this characteristic of light emitted from a LD wherein multiple fringes 512 due to gain confinement are clearly visible at the far field in the minor axis direction of the emitted beam of light. It should be noted that the fringes 512 appearing in the illustration of FIG. 2A contain only a minor amount of total energy in the beam of light, and therefore have little impact on the conventional M-square characterization of the corresponding beam profile. However, as discussed in greater detail below, the fringes 512 do have a detrimental effect on the performance of conventional flow cytometers. Alternatively, gain confinement along the slow axis direction of an edge emitting LD that is oriented perpendicular to the arrow 511 is much more relaxed. Consequently, as shown in FIG. 2A, the far field beam profile is much smoother along the slow axis of the LD's beam of light.

FIG. 3A depicts a conventional LD based optical subsystem for a flow cytometer. Those elements depicted in FIG. 3A that are common to the optical subsystem 50 illustrated in FIG. 1 carry the same reference numeral distinguished by a prime (') designation. As depicted in FIG. 3A, the conventional optical subsystem orients the fast axis of the LD 501 parallel to the direction in which the liquid sample flow passes through the viewing zone. In its most simplified configuration, the elliptical beam profile of the LD 501' is directly transposed by the spherical focusing lens 504' into the viewing zone. In an attempt to achieve optimal aspect ratio for the focused beam of light, various different conventional LD based optical subsystems have also included beam shaping optical elements in addition to those depicted in FIG. 3A.

The detrimental effect of fringes 512 along the fast axis of the LD 501' for conventional optical subsystem configurations clearly appears in the light scattering time profile depicted in FIG. 3B. Since scattering or fluorescence intensity is directly proportional to the local laser power impinging upon a particle, any fine structure in the beam of light's profile along the direction in which the liquid sample flow passes through the viewing zone will appear in the time profile of the signal produced by the flow cytometer. Such structures in the time profile are indistinguishable from signals generated by small particles, and will therefore cause the flow cytometer to trigger falsely and misidentify particles. In addition, the fringes 512 will also lead to uncertainty in the measurement of other cytometric parameters, such as in the area and width of the pulse depicted in FIG. 3B.

FIGS. 4A and 4B depict a yet another prior art optical subsystem for LD based flow cytometric applications disclosed in the '019 patent identified previously. Those elements depicted in FIGS. 4A and 4B that are common to the optical subsystem 50 illustrated either in FIG. 1 or 3A carry the same reference numeral distinguished by a double prime (") designation. As depicted in FIGS. 4A and 4B, by orienting the slow axis of the LD 501" parallel to the direction in which the liquid sample flow passes through the viewing zone the optical subsystem depicted in FIGS. 4A & 4B effectively overcomes the problem caused by the fringes 512 as described above. Unfortunately, the beam-diffusing element 513" placed before the spherical focusing lens 504" in FIGS. 4A and 4B to diffuse the beam of light perpendicular to the direction in which the liquid sample flow passes through the viewing zone produces a highly astigmatic beam of light near the viewing zone. Specifically, focusing this astigmatic beam of light at the viewing zone in the direction in which the liquid sample flow passes through the viewing zone increases the width of the beam of light perpendicular to the direction in which the liquid sample flow passes through the viewing zone so the beam's width become similar to or even wider than the sheath flow. Consequently, the optical subsystem depicted in FIGS. 4A and 4B not only diminishes the amount of light energy impinging upon particles flowing through the viewing zone, the optical subsystem also increases undesirable scattering of light from the interface between the liquid sheath flow and adjacent parts of the composite microscope objective 60.

FIG. 5 highlights the main differences between the optical subsystem disclosed in the '019 patent and the optical subsystem 50 depicted in FIG. 1. Instead of placing an out-of-plane beam-diffusing element 513" before the spherical beam focusing lens 504 as shown in FIG. 4, the high power cylindrical lens 505, depicted in FIGS. 5A and 5B as a cylindrical plano-convex lens, may be placed along the beam of light after the spherical beam focusing lens 504 and may be juxtaposed with the composite microscope objective 60. As shown in FIGS. 5A and 5B, the cylindrical lens 505 may focus the minor axis of the beam of light in the viewing zone while leaving the major axis of the beam of light essentially unchanged. Consequently, the optical subsystem 50 depicted in FIGS. 1, 5A and 5B may establish a beam of light profile at the viewing zone which is elliptical with:

1. a tightly focused minor axis that spans across the combined liquid sample and sheath flows; and
2. a smooth minor axis profile in the direction of the combined liquid sample and sheath flows that is the Fourier conjugate of the far field beam profile along the slow axis of LD 501.

Meanwhile, as shown in FIG. 5B, the out-of-plane beam width may be unaffected by the cylindrical lens 505. FIG. 5C shows a measured time profile of light scattered from a micro particle using the optical subsystem 50 depicted in FIGS. 1, 5A and 5B. The LD 501 used in making the measurement presented in FIG. 5C is the same as that used in generating the measured time profile of light scattered from a micro particle appearing in FIG. 3B. As shown in FIG. 5C, the side lobes caused by the fringes 512 along the fast axis of the LD 501 no longer have any material effect on performance of the flow cytometer 40.

FIG. 5D illustrates a perspective view of the cylindrical lens 505 of the LD based optical subsystem 50 coupled with the composite microscope objective 60 in accordance with some embodiments of the present disclosure. A beam of light may pass through the cylindrical lens 505 and a cuvette 603 of the microscope objective 60 substantially along the z axis and establish a beam profile 524 on a x-y plane at the viewing zone inside a flow channel 604 of the composite microscope objective 60.

FIG. 5E illustrates an enlarged view of the beam profile 524 shown in FIG. 5D in accordance with some embodiments of the present disclosure. FIG. 5E shows that the minor axis of the beam of light may be along the y axis and substantially parallel to the direction of liquid sample and sheath flows and the major axis of the beam of light may be along the x axis and substantially perpendicular to the direction of liquid sample and sheath flows.

FIG. 6 depicts yet another alternative diode laser based optical subsystem in accordance with some embodiments of the present disclosure adapted for use in a flow cytometer. Those elements depicted in FIGS. 6 and 6A that are common to the optical subsystem 50 illustrated in FIGS. 1, 5A and 5B carry the same reference numeral distinguished by a triple prime ('") designation. The optical subsystem 50'" depicted in FIGS. 6A and 6B is almost identical to that shown in FIGS. 1, 5A and 5B except that the viewing zone occurs without a composite microscope objective 60 because it occurs in a free-flowing jet stream 519 that includes both the sample and sheath flows that is emitted from a nozzle 518. Consequently, for the configuration of the optical subsystem 50'" depicted in FIGS. 6A and 6B, the high power cylindrical lens 505 is detached from the viewing zone that is located within the jet stream 519.

In the exemplary embodiments of the present disclosure depicted in FIGS. 1, 5A, 5B, 6A and 6B, the minor axis, i.e. the slow axis, of the LD 501 is substantially oriented perpendicular to the direction in which the liquid sample flow passes through the viewing zone. However, it will be apparent to those skilled in the art that using an alternative optical configuration the major axis, i.e. the fast axis, of the LD 501 may be reoriented to be perpendicular to the direction in which the liquid sample flow passes through the viewing zone. FIG. 7 depicts one example of such an alternative configuration of optical elements.

Those elements depicted in FIG. 7 that are common to the optical subsystem 50 illustrated in FIGS. 1, 5A, 5B, 6A and 6B carry the same reference numeral distinguished by a quadruple prime ('"") designation. As shown, the slow axis of the LD 501"" is oriented in the z-direction. The beam of light emitted from the LD 501"" is then rotated to the in-plane y-direction by a pair of ninety degrees)(90°) reflection mirrors 523a and 523b. In the illustration of FIG. 7, a normal to the first elliptically-shaped light beam reorienting mirror 523a is oriented in the x-y plane at forty-five degrees)(45°) to the x-axis, and a normal to the second elliptically-shaped light beam reorienting mirror 523b is oriented in the y-z plane at forty-five degrees)(45°) to the z-axis.

Composite Microscope Objective 60

Modern flow cytometers include a spatial filter, usually either a mechanical pinhole or a large core optical fiber, located at an image location of an objective lens to prevent undesired background light from entering the cytometer's detector(s). Because particles remain in the cytometer's viewing zone for a few microseconds, microscope objectives with large numerical aperture must be used to maximize light collection efficiency. To support multiple spatially separated excitation laser beams in flow cytometers, as disclosed in U.S. Pat. No. 4,727,020, it is also desirable to use an objective with large field of view. In order to achieve these goals, U.S. Pat. Nos. 6,510,007 and 7,110,192 disclose an objective design using a modified apochromat with a gel-coupled or epoxy bonded near hemisphere lens as the optical element closest to the sample that is followed by multiple meniscus lenses. While such microscope objectives provide both a satisfactory numerical aperture and field of view, they significantly sacrificed image quality thereby:

1. limiting effective use of the spatial filter; and
2. exhibiting poor background light discrimination.

Further, such refractive microscope objectives are bulky, expensive to manufacture and often exhibit severe chromatic aberration. To overcome these limitations, Published Patent Cooperation Treaty ("PCT") Patent Application No. WO 01/27590 discloses an alternative objective design based on a spherical concave mirror. The design offers large numerical aperture and good image quality along the optical axis. However, due to its poor off-axis characteristics, such a design is unsuitable for flow cytometers having multiple, spatially separated laser beams.

FIG. 8 depicts one embodiment in accordance with the present disclosure for the composite microscope objective 60 depicted in FIGS. 1, 5A, 5B and 7. As depicted in FIG. 8, the composite microscope objective 60 may image a viewing zone that is located inside a prismatically-shaped glass cuvette 603 within a small flow channel 604, that may have a rectangular cross-sectional shape, through which passes the particle carried by combined liquid sample and sheath flows. A plano-concave back-surface mirror 601 included in the composite microscope objective 60 may be made of an optically transparent material that may have a refractive index similar to that of the glass cuvette 603, such as glass or optical quality plastics. To minimize optical loss, the back-surface mirror 601 may include a flat front surface that is optically coupled to an abutting flat surface of the prismatically-shaped cuvette 603. Optical coupling of the back-surface mirror 601 to the cuvette 603 may employ an index-matching gel, optical adhesive or direct optical bonding. Alternatively, the back-surface mirror 601 may also be formed integrally with the cuvette 603.

The composite microscope objective 60 may also include a plano-aspheric corrector plate 602 that is also made of an optically transparent material that may have a refractive index similar to that of the glass cuvette 603, such as glass or optical quality plastics. To reduce optical loss, a flat surface of the corrector plate 602 may be optically coupled to an abutting flat surface of the prismatically-shaped cuvette 603 on a face thereof that is diametrically opposite to the back-surface mirror 601. Optical coupling of the corrector plate 602 to the cuvette 603 may employ an index-matching gel, optical adhesive or direct optical bonding. The aspheric surface of the corrector plate 602 furthest from the corrector plate 602 may carry an anti-reflective coating to reduce optical transmission loss, although such a coating is not a mandatory requirement for a composite microscope objective 60 in accordance with some embodiments of the present disclosure. The shape of the aspheric surface of the corrector plate 602 is similar to that in a classical Schmidt camera, (Schmidt, B., *Mitt. Hamburg Sternwart* 7 (36) 1932). As known by those skilled in the art, the corrector plate of a Schmidt camera includes a circularly shaped neutral zone where the corrector plate does not deviate rays of light passing through the plate. For use in the composite microscope objective 60, outside of the neutral zone of the corrector plate 602, where the plate thickness is thinnest, the corrector plate 602 may have negative optical power while inside the neutral zone the corrector plate 602 may have positive optical power. The exact shape of the aspheric corrector plate 602 may be readily obtained using any commercially available optical ray tracing tool by any person having ordinary skill in the art. Note that in the flow cytometer 40, the beam of light generated by the optical subsystem 50 depicted in FIGS. 1, 5A, 5B and 7 enters the cuvette 603 perpendicularly to the flow channel 604 through one (1) of the two (2) faces of the cuvette 603 that do not abut the back-surface mirror 601 or corrector plate 602.

Combined Microscope Objective 65

FIG. 8A illustrates a perspective view of a combined microscope objective 65 in accordance with some embodiments of the present disclosure. The combined microscope objective 65 may include the composite microscope objective 60, as illustrated in FIG. 8 and the cylindrical lens 505. The cylindrical lens 505 may direct a beam of light to the viewing zone in the flow channel 604 to illuminate particles in the sample flow. After particles are illuminated in the viewing zone, the composite microscope objective 60 then may collect imaging light scattered from and fluoresced by particles within the view zone.

FIG. 8B illustrates a perspective view of the combined microscope objective 65 coupled with a flow cell 619 in according with some embodiments of the present disclosure. Liquid sample 623 may be pumped up from a sample tube 621 into a flow section 620 of the flow cell 619 by a pump 624. The pump 624 may be the peristaltic pump 80, as illustrated in FIG. 17. Liquid sheath 622 may be also pumped into the flow section 620 of the flow cell 619. The pump for pumping the liquid sheath 622 into the flow cell 619 may be a part of the fluidic system 70, as illustrated in FIG. 14 or 15. The liquid sample 623 may be combined with the liquid sheath 622 in the flow section 620 of the flow cell 619 and then hydro-dynamically focused within the viewing zone inside the flow channel 604 of the combined microscope objective 65. The combined microscope objective 65 or the composite microscope objective 60 may be positioned on the flow cell 619. Persons skilled in the art may also refer to a combination of the microscope objective 65 or the composite microscope objective 60 and the flow cell 619 as a flow cell. The cross-sectional area of the flow section 620 at the top of the flow cell 619 may be smaller than the cross-sectional area of the flow section 620 at the bottom of the flow cell 619 to facilitate hydrodynamic focusing of the liquid sample 623 in the viewing zone. It should be noted that the various aspects of the present disclosure are not limited to specific direction of liquid sheath or sample flow and specific shape of the flow cell or the microscope objective.

FIG. 9A depicts the result of ray tracing for the embodiment of composite microscope objective 60 illustrated in FIG. 8. As depicted in FIG. 9A, scatter and fluorescence emissions from three (3) spatially separated locations in the flow channel 604 near the center of the cuvette 603 may:

1. initially propagate toward back-surface mirror 601 and pass first through the cuvette 603 to be internally reflected by the back-surface mirror 601;
2. then pass through the cuvette 603;
3. subsequently pass through the aspheric corrector plate 602; and
4. finally forms three (3) distinct images near an image plane 605.

Note that rays traversing the composite microscope objective 60 depicted in FIG. 9A are nearly optically-uniform and that light emitted near the center of the cuvette 603 traverses the corrector plate 602 at near normal incidence. Consequently, the composite microscope objective 60 introduces very little chromatic dispersion in light emitted near the center of the cuvette 603.

Further, it is well known in the astrophysics community that Schmidt camera offers the unparalleled combination of a fast focal ratio and a large field of view with near diffraction limited optical performance. The principal drawback in a conventional Schmidt camera is that the image surface lies inside the instrument. For the composite microscope objective 60, light near the center of the cuvette 603 propagates opposite to that of a conventional Schmidt camera and therefore the image surface lies outside the composite microscope objective 60. Consequently, the present disclosure takes full advantage of the optical performance of the Schmidt camera without experiencing its limitation. FIGS. 9B1 through 9B3 depict spot diagrams near the image plane 605 for three (3) emission locations, 606, 607, 608 in viewing zone within the flow channel 604 that may be separated 150 micron from each other. The diameters of all images depicted in FIGS. 9B1 through 9B3 may be less than 35 microns.

Light emitted from the viewing zone within the flow channel 604 of the composite microscope objective 60 depicted in FIGS. 8 and 9A that traverses the aspheric corrector plate 602 may suffer from a small amount of chromatic aberration. FIG. 10 depicts an alternative embodiment for the composite microscope objective 60 depicted in FIGS. 1, 5A, 5B and 7 in accordance with some embodiments of the present disclosure. Those elements depicted in FIG. 10 that are common to the composite microscope objective 60 illustrated in FIGS. 8 and 9A carry the same reference numeral distinguished by a prime (') designation. The shapes of the back-surface mirror 601' and the aberration corrector plate 602' depicted in FIG. 10 are modified slightly to produce collimated afocal images of the emission locations near the viewing zone within the flow channel 604'. In FIG. 10 the composite microscope objective 60' may include a chromatic compensating doublet lens 609 inserted between the corrector plate 602' and the image plane 605'. In addition to focusing the light emitted from the corrector plate 602' onto the image plane 605', the doublet lens 609 may also serve to further reduce the residual chromatic aberration introduced by the aspheric corrector plate 602'.

It is not essential that the flat surface of the corrector plate 602 to be optically coupled to the cuvette 603. FIG. 11 depicts an alternative embodiment of the composite microscope objective 60 in accordance with some embodiments of the present disclosure. Those elements depicted in FIG. 11 that are common to the composite microscope objective 60 illustrated in FIGS. 8 and 9A carry the same reference numeral distinguished by a double prime (") designation. FIG. 11 depicts the aberration corrector plate 602" optically decoupled from the cuvette 603". Although not essential for operation of the composite microscope objective 60", to improve the light transmission efficiency both surfaces of the corrector plate 602" and the exposed flat surface of the cuvette 603" may carry an anti-reflectively coating. It is understood that the corrector plate 602" shown in FIG. 11 may be held in fixed relationship to the combined back-surface mirror 601 and cuvette 603 by a mechanical support not depicted in FIG. 11. Similar to the composite microscope objective 60 and 60' depicted respectively in FIGS. 9A and 10, the composite microscope objective 60" with detached corrector plate 602" may be configured to provide either finite focal length image, or an afocal system which in turn is focused to a finite distance image plane by an additional chromatic compensating doublet lens 609.

FIG. 12 depicts yet another alternative embodiment of the composite microscope objective 60. Those elements depicted in FIG. 12 that are common to the composite microscope objective 60 illustrated in FIGS. 8, 9A and 11 carry the same reference numeral distinguished by a triple prime ("') designation. The composite microscope objective 60"' depicted in FIG. 12 is adapted for collecting scatter and fluorescence emissions from cells or other microscopic particles carried in the jet stream 519 emitted by the nozzle 518. The composite microscope objective 60"' may include a concave, spherically shaped, front surface mirror 610 and an aberration corrector plate 612. The front surface mirror 610 may be made of glass or other types of hard material with a highly reflective coating on the concave surface 611 or made of metal with polished concave surface 611. Similar to the corrector plate 602, the plano-aspheric corrector plate 612 may be made of a thin piece of transparent material, such as glass or optical quality plastics. The aspheric surface may be formed on either side of the corrector plate 612. Both surfaces of the corrector plate 612 may be coated with an anti-reflective coating to reduce optical transmission loss, although such a coating is not a mandatory requirement for a corrector plate 612 in accordance with some embodiments of the present disclosure. It is understood that the front surface mirror 610 and the corrector plate 612 may be held in fixed relationship to each other by a mechanical support not depicted in FIG. 12. Scatter and fluorescence light emitted from cells or other types of microscopic particles in the viewing zone inside the jet stream 519 may be reflected by the concave surface 611 of the front surface mirror 610. The aberration due to reflection from the concave surface 611 may be corrected by the corrector plate 612 after light traverses through the corrector plate 612. It is understood by those having skill in the art that the composite microscope objective 60"' may be configured to provide either a finite focused image similar to that depicted in FIG. 9A, or a collimated afocal image which is focused at finite distance from the composite microscope objective 60"' by a chromatic aberration correction doublet similar to the doublet lens 609 depicted in FIG. 10.

FIG. 13 depicts an adaptation of the composite microscope objective 60 for imaging specimens fixed to the surface of a transparent substrate such as a glass slide. Those elements depicted in FIG. 13 that are common to the composite microscope objective 60 illustrated in FIGS. 8, 9A and 11 carry the same reference numeral distinguished by a quadruple prime ("") designation. The composite microscope objective 60"" depicted in FIG. 13 may include two (2) optical elements, one a plano-concave back surface mirror 617 made of a transparent material, such as glass or optical quality plastics, and an aberration corrector plate 618. As depicted in FIG. 13, the specimen to be imaged may be fixed to a front surface 615 of a transparent, usually glass slide 616. The slide 616 may be optically coupled, for example, using a thin layer of index matching fluid, to the flat surface of the back surface mirror 617. Scatter and fluorescence light emitted by the specimen may:

1. initially propagate through the slide 616 and the back surface mirror 617;
2. be internally reflected by the back surface mirror 617 back through the slide 616;
3. then pass through the corrector plate 618; and
4. finally form an image at an image plane that is located beyond the corrector plate 618.

Fluidic Subsystem 70

The performance of a flow cytometer depends critically on a stable liquid sheath flow. In particular, flow cytometers that have multiple spatially separated excitation laser beams or perform droplet sorting rely on a constant velocity of the liquid sheath flow for timing synchronization. As disclosed in U.S. Pat. No. 5,245,318, conventional flow cytometers provide a stable liquid sheath flow by using an airtight fluidic system that either:

1. applies constant air pressure in a sheath liquid reservoir to push the fluid through the flow cell; or
2. by sucking the fluid from the sheath liquid reservoir through the flow cell using a vacuum pump.

These systems are bulky, expensive to manufacture, and prone to failure. More recently, U.S. Pat. No. 8,187,888 discloses including a sheath liquid subsystem that pumps the liquid sheath flow from the sheath liquid reservoir into the viewing zone and a waste sheath liquid pump that pumps waste sheath liquid from the viewing zone into the waste tank. Although it appears that the disclosed sheath liquid subsystem has never been used in velocity critical flow cytometers, this patent reports that the disclosed sheath liquid subsystem overcomes most of the drawbacks of conventional sheath liquid flow stabilization by:

1. damping pump pulsations by locating:
   a. one fluidic capacitor between the sheath liquid pump and the flow cell; and
   b. another fluidic capacitor between the flow cell and the waste pump; and
2. a pump controller whose operation is responsive to a pressure sensor that measures the pressure difference between the inlet and outlet of the flow cell.

However, the disclosed sheath liquid subsystem has other limitations. For example, the pressure sensor located near the outlet of the flow cell could be a potential source of contamination.

FIG. 14 depicts a fluidic subsystem 70 in accordance with some embodiments of the present disclosure that includes a sheath liquid reservoir 702 and a liquid pump 701 that draws sheath liquid from the sheath liquid reservoir 702. The liquid pump 701 may be a diaphragm pump, a peristaltic pump, a piston pump, or any types of continuous fluid pump. An outlet of the liquid pump 701 may connect to an inlet of a T-coupling 703 that receives sheath liquid from the liquid pump 701. The T-coupling 703 may have two (2) outlets. The first outlet may connect to a bypass conduit 710 for returning a fraction of the sheath liquid received by the T-coupling 703 from the liquid pump 701 back to the sheath liquid reservoir 702. Returning a fraction of the sheath liquid received by the T-coupling 703 from the liquid pump 701 back to the sheath liquid reservoir 702 is advantageous for two (2) reasons.

1. As depicted in FIG. 14, the bypass conduit 710 is left open to the surrounding atmosphere which effectively dampens pulsation to thereby significantly reducing the pulsation inherent in the operation of the liquid pump 701.
2. Returning a fraction of the sheath liquid received by the T-coupling 703 from the liquid pump 701 back to the sheath liquid reservoir 702 also effectively reduces the throughput of the liquid pump 701 thereby allowing the use of comparatively high flow rate, low cost pumps in the flow cytometer 40.

Denote the flow resistance of the bypass conduit 710 as "r" and the flow resistance of path from the T-coupling 703 to the flow channel 604 of the cuvette 603 as "R." The output resistance to the sheath pump $R_p$ is then equal to:

$$R_p \frac{rR}{r+R} \quad (1)$$

Since R>>r, the behavior of the liquid pump 701 is therefore dominated by the resistance of the bypass conduit 710 whose fluid dynamic properties may be temperature insensitive. Thus, the configuration of the fluidic subsystem 70 depicted in FIG. 14 may also provide a simple mechanism for achieving a temperature insensitive sheath liquid flow to the flow channel 604. As depicted in FIG. 14, the second outlet of the T-coupling 703 connects to the flow channel 604 that extends through the cuvette 603 first via a small reservoir capsule 704 and then via a filter cartridge 705. As depicted in FIG. 15, a piece of tubing 704', which may be, for example, about 4 ft. long may be substituted for the small reservoir capsule 704. During initialization of the fluidic subsystem 70, some air becomes trapped in the filter cartridge 705 near its inlet which as depicted in FIG. 15 is located above an outlet of the filter cartridge 705. The air trapped in the filter cartridge 705 may act as an additional fluidic capacitor effectively reducing to negligible level the pulsation in sheath liquid emitted into the flow channel 604. Due to the large fluidic resistance at the flow channel 604, the air trapped inside the filter cartridge 705 becomes compressed. When the liquid pump 701 is turned off, a trapped in the filter cartridge 705 is pushed back towards the T-coupling 703 analogous to a discharging capacitor. Without the small reservoir capsule 704, some air ejected from the filter cartridge 705 reaches the bypass conduit 710 due to its low fluidic resistance, and will be pushed out of the fluidic subsystem 70 once the liquid pump 701 is turned on again. Without additional air supply, such a scenario will repeat until most of the air becomes purged from the fluidic subsystem 70 causing the filter cartridge 705 to lose its effectiveness as a pulsation damper. The purpose of the small reservoir capsule 704 or the piece of tubing 704' is therefore to provide a reservoir for isolating the filter cartridge 705 from the bypass conduit 710 ensuring that air trapped inside the filter cartridge 705 remains within the fluidic subsystem 70 despite repeated on-off operations of the liquid pump 701.

The pulsation damping effect of the trapped air near the inlet of the filter cartridge 705 is clearly evident in the histograms depicted in FIGS. 16A and 16B. FIG. 16A depicts measured particle flight times at the flow channel 604 when a pocket of air is trapped near the inlet of the filter cartridge 705. FIG. 16B depicts measured particle flight times at the flow channel 604 when the trapped air is purged from the fluidic subsystem 70. The result depicted in the histograms of FIGS. 16A and 16B is made using two (2) knife edge shaped laser beams focused near the center of the flow channel 604 that are spaced approximately 200 micrometers apart. The horizontal axis of the FIGS. 16A and 16B is the flight time a particle takes from one laser beam to the other measured by recording the peak arrival time of light scattered from the particle at ninety degrees (90°) from the excitation beams. In both cases, the average flight time for particles to cross the two laser beams is the same. As shown in FIG. 16A, when the filter cartridge 705 retains some air, all particles take about the same amount of time to cross the two laser beams. If the filter cartridge 705 retains no air, as shown in FIG. 16B, the distribution of flight times not only broadens, but also becomes bimodal. In other words, some particles take less time while others take longer than average amount of time to cross the two laser beams, a phenomenon that can be easily attributed to sheath liquid velocity pulsation at the flow channel 604.

In the embodiments of the present disclosure discussed so far, the fluidic resistance along bypass conduit 710 as well as between the T-coupling 703 and the flow channel 604 may not be adjustable. As should be apparent to those ordinary skilled in the art, flow restrictors such a fixed restrictor or adjustable valves 712, 712' and 711, 711' and may be advantageously inserted in the bypass conduit 710 and between the T-coupling 703 and the flow channel 604 to permit adjusting the flow rate through the flow channel 604. Alternatively, the velocity of sheath liquid flowing through the flow channel 604 may also be adjusted using a liquid pump 701 that is driven by a variable speed brushless DC motor.

Peristaltic Pump 80

Peristaltic pumps are volumetric pumps in which a set of linearly or circularly moving rollers progressively compress a compressible tube to propel the fluid through the tube. Peristaltic pumps are widely used particularly to pump clean/sterile or aggressive fluids to avoid cross contamination with exposed pump components. Conventional peristaltic pump exhibits a pulsation. Each time a roller rolls off the tube near the pump outlet, caused by the temporary increase of tube volume when the compressed tube expands back to its original shape. The pulsation is undesirable in applications that require smooth flow. Many attempts have been made in the past to reduce the pulsation. For example, U.S. Pat. Nos. 3,726,613 and 3,826,593 introduced a cam operated pusher which synchronously exerts an external pressure on the tube to compensate for the tube expansion. In U.S. Pat. No. 4,834,630, a plurality of tubes mounted on segmented rollers are joined together at the pump inlet and outlet by T-shaped couplers such that pulsations from individual tubes would be reduced by averaging. U.S. Pat. No. 7,645,127 proposed a pump tube with slightly larger inner diameter near the inlet so that the tube decompression near the pump outlet is compensated by the compression of a larger volume tube near the inlet. The various methods either significantly increased the complexity of the peristaltic pump or had limited success in reducing the pulsation effect.

A peristaltic pump 80 in accordance with some embodiments of the present disclosure is illustrated in FIG. 17. The pump may include a housing 809 with arcuate curved track 808, three rollers 810, 811 and 812 attached to a rotor 816 rotatable within the housing 809, and a compressible tube 807 sandwiched between the arcuate curved track 808 of the housing 809 and the rollers 810, 811 and 812, in particular at the surface 814 of rollers 810, 811 and 812. As depicted schematically in FIGS. 18A through 18D, the rollers 810, 811 and 812 of the peristaltic pump 80 are spaced at substantially equal angular distances, separations or spacings from each other around the perimeter of the rotor 816. The rollers 810, 811, 812 may rotate about a longitudinal axis thereof, so that limited friction occurs between the rollers and the compressible tube. This may also apply for the subsequently described rollers. For simplicity, it is assumed in the following discussions that the rotor 816 rotates counterclockwise, although it is to be understood that the discussions apply equally well to a peristaltic pump with clockwise rotating rotor. The compressible tube 807 of the housing 809 may be divided into several sections:

1. an open section between point 801 and point 806 where the compressible tube 807 experiences no compression;

2. a pump inlet section between point 801 and point 802 where the compressible tube 807 is progressively compressed until fully closed when a roller rolls over the section;

3. two pumping sections between point 802 and point 803, as well as between point 804 and point 805 wherein the compressible tube 807 is fully closed by the roller;

4. a recess section between point 803 and point 804 in which the compressible tube 807 progressively expands from fully closed to fully open as a roller rolls through the expansion part of the recess section from point 803 to point 813;

5. then the compressible tube 807 is progressively compressed to fully closed as a roller rolls through a compression part of the recess section from point 813 to point 804; and 6. the exit section between point 805 and point 806 where the compressible tube 807 progressively expands from fully closed to fully open as a roller rolls through the section.

In other words, when a roller rolls anticlockwise over the compressible tube 807 from inlet point 801 to outlet point 806, the inner gap of the compressible tube 807 may:

1. progressively decrease from fully open at point 801, to fully closed at point 802 and remain closed until point 803;

2. then progressively expand back to fully open at point 813;

3. then progressively decrease to fully closed at point 804, and remain closed until the roller reaches point 805; and 4. finally progressively expand back to fully open at point 806.

Figure 18:
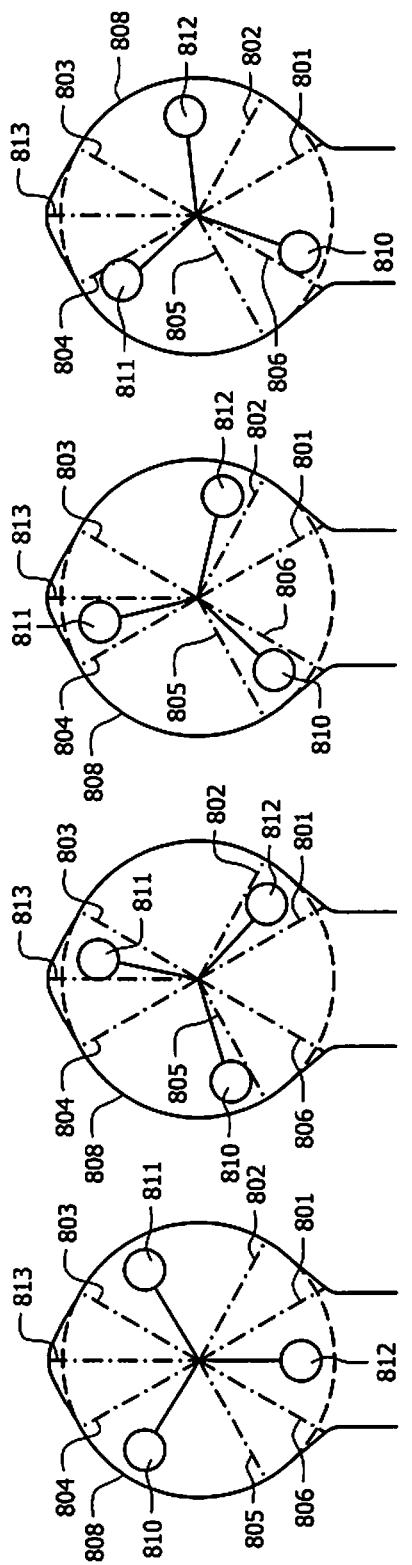

The size of the gap inside the compressible tube 807 is schematically illustrated in FIGS. 18A through 18D as the spacing between dashed circle and the solid compressible tube 807. As illustrated in FIGS. 18A through 18D, in this embodiment of the peristaltic pump 80, the angular distances, separations or spacings between points 801 and 803, points 802 and 813, point 813 and 805, as well as between point 804 and 806 may be identical to the angle between adjacent rollers. As a result, when the roller 810 rolls through the pumping section from point 804 to point 805, as depicted in FIGS. 18A through 18B, its interaction with the compressible tube 807 may completely determine the fluid flow rate of the peristaltic pump 80. Once the roller 810 reaches the exit section between point 805 and 806, as shown in FIG. 18C, the compressible tube 807 underneath the roller 810 may start to progressively expand and a gap may start to grow. Meanwhile, the roller 811 may arrive at the compression part of the recess section and start to progressively compress the compressible tube 807. In the peristaltic pump 80, the shape of the compression part of the recess section between point 813 and point 804 along the compressible tube 807 is such that the volume of liquid pushed out by the compression of the underneath roller 811 in the compression part of the recess section between point 813 and point 804 may substantially fill the volume created by the compressible tube 807 expansion underneath roller 810 in the exit section between point 805 and point 806. During this period, the compressible tube 807 is partially open underneath both rollers 810 and 811 and completely closed underneath roller 812. Consequently, the pumping action may be mainly delivered by roller 812. In particular, since by design the total volume of liquid in the section of the compressible tube 807 between point 813 and point 816 remains substantially constant during this period, the flow rate of the peristaltic pump 80 in the state shown in FIG. 18C may remain substantially the same as that in the state shown in FIGS. 18A and 18B. Once the roller 810 passes point 806, roller 811 reaches the pumping section between point 804 and point 805. Note there is no physical difference between the rollers 810, 811 and 812, the flow rate of the peristaltic pump 80 may therefore remain substantially constant throughout the entire process.

The mechanism of the pulseless peristaltic pump in accordance with some embodiments of the present disclosure may be understood more clearly if it is viewed along a circular coordinate following the movement of the rollers. Referring to FIG. 19, denote as V the volume of the fluid inside a compressible tube 819 from the outlet to a nearest roller 820 that closes off the compressible tube 819, i.e., the amount of fluid represented by the hatched area 818 shown in FIG. 19. Clearly, V depends on the angular position, θ, of the roller 820, as well as δ, the amount of tube compression exerted by all other downstream rollers.

$$V = V(\theta, \delta_1, \delta_2, \ldots) \quad (2)$$

Consequently, the flow rate, F, of a peristaltic pump is related to the time derivative of Vc by:

$$-F = \frac{dv}{dt} = \frac{\partial v}{\partial \theta} R + \sum_i \frac{\partial v}{\partial \delta_i} \frac{d\delta_i}{dt} \quad (3)$$

Here R is the rotational speed of the rotor and the subscripts are used to identify multiple downstream rollers. The first term on the right hand side of Eqn. (3) represents the contribution from the roller that closes off the tube. The partial derivative $$\frac{\partial v}{\partial \theta}$$

is therefore independent of θ. The summation term represents contributions from all other downstream rollers partially compressing the compressible tube 819. Now let ΔS be the cross sectional area change due to the compression of the compressible tube 819 by the roller 817, and L be the length of tube where its cross sectional shape is affected by the tube compression. Then, it is obvious to a person skilled in the art that L is proportional to the tube compression δ, and ΔS proportional to its square, $\delta^2$. Consequently, ΔV, the volume of fluid lost due to the compression of the compressible tube 807 by the roller, follows Eqn. (4):

$$\Delta V \propto L \cdot \Delta S \propto \delta^3 = (D-G)^3 \quad (4)$$

where D is the inner diameter of the compressible tube and G is the minimum gap indicated in FIGS. 19, 19A and 19B which is also represented in FIGS. 18A through 18D by the spacing between the dashed circle and the solid track 808 of the housing 809. FIG. 19A and 19B are detailed cross-sectional views orthogonal to the peristaltic pump's tube's length taken along the lines 19A and 19B in FIG. 19 illustrating the tube's partial compression by the roller. FIG. 19A shows the cross-sectional area 818a taken along the line 19A in FIG. 19. FIG. 19B shows the cross-sectional area 818b taken along the line 19B in FIG. 19. Now referring to FIGS. 20A and 20B, in the circular coordinate system, FIG. 20A corresponds to the state of pump shown in FIGS. 18A and 18B. During this period, there is no roller downstream of the roller 810' and the summation term in Eqn. (3) vanishes. FIG. 20B corresponds to the state of the pump shown in FIG. 18C. The compressible tube 807 is closed off by roller 812' and partially compressed by the rollers 810' and 811'. However, volumetric changes introduced by the two rollers 810' and 811' substantially cancel each other. Consequently, the summation term is Eqn. (3) vanishes as well. As a result, the flow rate of the peristaltic pump 80 may remain substantially constant regardless of roller positions.

The shape of the compressible tube 807 satisfying the above requirement can be readily derived from Eqn. (4). Referring to FIG. 18C, if the gaps of the arcuate curved track 808 in the compression part of the recess section between point 813 and point 804, $G_{13,4}$, and in the exit section between point 805 and point 806, $G_{5,6}$, follow the equation:

$$(D-G_{13,4})^3 + (D-G_{5,6})^3 = D^3 \quad (5)$$

then the total fluid volume in the two sections may remain substantially constant, as shown in FIG. 21. In the peristaltic pump 80, the shape of the pump housing 809 may be symmetrical with respect to its center line, such that the entrance half of the pump housing 809 is the mirror image of the exit half of the housing 809, as shown in FIG. 17. The peristaltic pump 80 can therefore be operated both in counterclockwise and clockwise rotation with very little pulsation, although it is understood that the symmetry is not required to realize a pulseless peristaltic pump in accordance with some embodiments of the present disclosure. For example, as long as the gaps of the arcuate curved track 808 in the section between point 813 and point 803, $G_{13,3}$, and in the section between point 802 and point 801, $G_{2,1}$, follow Eqn. (6)

$$(D-G_{13,3})^3 + (D-G_{2,1})^3 = D^3 \quad (6)$$

a peristaltic pump in accordance with some embodiments of the present disclosure will exhibit little pulsation when the rotor 816 rotates clockwise.

FIG. 22 depicts an alternative embodiment of a peristaltic pump in accordance with some embodiments of the present disclosure. Those elements depicted in FIG. 22 that are common to the peristaltic pump 80 illustrated in FIG. 17 carry the same reference numeral distinguished by a prime (') designation. The peristaltic pump 80' may include an arcuate curved track 808' having two (2) recesses 818 and 819, and four (4) rollers 820, 821, 822 and 823. In the embodiment depicted in FIG. 22, the fluid volume loss due to the tube expansion near the outlet of the pump is compensated by the combined effect of the compression of the compressible tube by rollers 820 and 823 near the two recesses 818 and 819.

FIG. 23 depicts yet another alternative embodiment of a peristaltic pump in accordance with the present disclosure. Those elements depicted in FIG. 23 that are common to the peristaltic pump 80 illustrated in FIG. 17 and the peristaltic pump 80' illustrated in FIG. 22 carry the same reference numeral distinguished by a double prime (") designation. The peristaltic pump 80" may include six (6) rollers 820, 821, 822, 823, 824, 825 and an arcuate curved track 808" having two recesses 818" and 819". In the peristaltic pump 80", the fluid volume loss due to the tube expansion near the outlet of the pump is compensated by the action of the roller immediately upstream of the one recess 818" or 819" near the pump outlet.

Pulsation due to the expansion of a compressed compressible tube near the outlet of a peristaltic pump may also be overcome by a peristaltic pump having a programmable rotor speed. FIGS. 24A through 24C illustrate pertinent aspects of an alternative embodiment mechanism for minimizing peristaltic pump pulsation in accordance with the present disclosure for a 3-roller peristaltic pump. As depicted in FIG. 24B, the track 828 is substantially circular between the pump inlet and pump exit section. Consequently, as indicated by the spacing between the dashed circle 829 and the solid curve of the track 828, the compressible tube is completely closed by various ones of the pump's three (3) rollers 825, 826, 827 between the pump inlet and pump outlet. FIG. 24A illustrates schematically in a circular coordinate system the roller positions for the peristaltic pump depicted in FIG. 24B. Since there is only one roller downstream of the one that closes off the tube, Eqn. (3) is much simplified:

$$-F = R\left(\frac{\partial V_c}{\partial \theta} + \frac{\partial V_c}{\partial \delta}\frac{d\delta}{d\theta}\right) \quad (7)$$

Here the tube compression δ (θ) is explicitly expressed as a function of roller position θ. The terms inside the parentheses represent the change rate of fluid volume with respect to roller position. The first term is the contribution from the roller that closes off the tube, i.e., roller 827 in FIG. 24A, and the second term the contribution from the roller in the exit section. Note that by definition, the volume change rate is negative and the second term inside the parentheses vanishes when there is no roller in the exit section. The dotted curve in FIG. 24C is a representative plot of the negative volume change rate with respect to the position of the roller. The bump along the curve, due to the tube expansion when a roller rolls off the tube near the pump outlet, is the cause for pulsation in conventional peristaltic pumps having a constant rotor speed. However, for the peristaltic pump depicted in FIGS. 24A through 24C, the rotor speed, R, shown as dashed curve in FIG. 24C, may be set to vary in synchronism with the rotor position and inversely proportional to the change rate of the fluid volume. Consequently, the flow rate of the pump, which is the product of the rotor speed and the change rate of the fluid volume, may remain constant, as indicated by the solid line at the top of FIG. 24C. Note the terms inside the parentheses of Eqn. (7) may be uniquely determined by the mechanical structure of the pump. The rotor speed profile can therefore be readily generated from the shape of the track 828 in accordance with Eqn. (4).

To those skilled in the art, there are many ways to realize a programmable rotor, for example, with stepping motor or DC servo motor.

WDM Device 90

In many multicolor fluorescence detection instrumentations, such as flow cytometers, (Practical Flow Cytometry, Howard M. Shapiro, Wiley (2003) ISBN 0471411256), the fluorescence light emitted from the object of interest is:

1. collected by a microscope objective;
2. reimaged through a small pinhole or a multimode optical fiber;
3. then collimated and separated into multiple colored bands; and
4. finally detected by photo detector, such as photomultiplier tube (PMT), PIN photodiode or avalanche photodiode (APD).

A PMT is essentially a special type of electron tube. This "pre-semiconductor age" device is bulky and expensive. In addition, it has poorer quantum efficiency and less reproducible spectral response than silicon based semiconductor detectors, particularly in the biologically important red to near infrared spectral region. Despite the disadvantages, PMT has excellent noise characteristics. For example, the dark current of a typical 13 mm PMT (e.g., the R9305 from Hamamatsu Corporation of Japan) is only about 1 nA. In contrast, an APD's dark current would be 10 times greater even if its active area were reduced to ½oth of that of the PMT. As a result, PMT has been the de-facto low-level light detector in many commercial fluorescence detection flow cytometers. Only in certain scientific applications where event rate is low and dark current may be discriminated against by expensive photon-counting techniques that the PMT has been replaced by APD detectors. (c.f., High-Throughput Flow Cytometric DNA Fragment Sizing, A. V. Orden, R. A. Keller, and W. P. Ambrose, *Anal. Chem.*, 2000, 72 (1), p 37-41). More recently, a Geiger mode APD array was also promoted as PMT replacement. (For example, the multi pixel photon counter of Hamamatsu Photonics of Japan and the solid-state photomultiplier of SensL Inc. of Ireland.) These detectors, however, also have high dark current and are nonlinear at high event rate.

The only industry where APD has found wide acceptance is in optical communication. It is known that if the APD's active area is reduced to less than 1 $mm^2$, the corresponding dark current will be reduced to the same level as a PMT. In optical communication, the light is a laser beam out of single mode optical fiber. Such a beam can be easily collimated then focused down to an area much smaller than 1 $mm^2$. It should be noted that the color separation devices used in the fluorescence light detection instruments, as described in U.S. Pat. No. 6,683,314 and references therein, are almost identical in function and architecture to the wavelength division multiplexers (WDM) widely used in optical communication, as described in U.S. Pat. Nos. 4,482,994, and 5,786,915. A fundamental reasons preventing the use of small area APD in fluorescence detection instrumentation is the well-known theorem of etendue conservation: the fluorescence light coming through a pinhole or multimode optical fiber is an extended light source with an etendue hundreds of times greater than that of a laser beam out of a single mode optical fiber. Consequently, as illustrated in FIG. 26, it cannot be collimated over an extended distance unless the diameter of the beam is significantly expanded. Unfortunately, the larger the beam diameter, the greater the technical challenge to focus it down to a small spot. Since efficient color separation can only be accomplished economically with collimated light beam, small area APD has not been considered viable for multicolor fluorescence light detection applications. Clearly, a technology capable of collimating a large etendue light beam over an extended distance without significantly expanding the beam diameter would be highly desirable. Such a technology would enable a WDM like device for fluorescence light detection with characteristics comparable to low noise semiconductor detectors.

FIG. 25 shows the optical ray trace for an exemplary 6 port wavelength division multiplexer of the present disclosure using zig-zag configuration. As shown in FIG. 25, fluorescence light going through a pinhole or emitted from the facet of a multimode optical fiber, such as the optical fiber 852 depicted in FIG. 1, forms an extended object or light source at location 901, i.e. the optical input of the WDM 90. The size of the object is defined by the diameter of the pinhole or the core diameter of the multimode optical fiber. Note that the practical size of the pinhole or the core diameter of the multimode optical fiber is measured in millimeters, in contrast to the diameter of single mode optical fibers that are measured in micrometers. Consequently, the etendue of the fluorescence light source, defined as the product of beam size and its divergence angle, is hundreds times greater than its counterpart in optical communication. According to the theorem of the conservation of etendue (Julio Chaves, *Introduction to Nonimaging Optics*, CRC Press, 2008 [ISBN 978-1420054293]), light from such an extended source, similar to that from a flash light, can only be kept collimated for a very limited distance, particularly when the diameter of the collimated portion needs to be small.

As depicted in FIG. 25, a collimating optical element, in this case an achromatic doublet lens 902, may capture the light from source 901, and project a magnified image of the object near a final focusing lens 905. The size of the image near 905 may be kept approximately the same as the effective size of the collimating optical element 902. Consequently, beam of light propagating between the collimating optical element 902 and the focusing lens 905 may be effectively collimated. As shown in FIG. 25, so long as the magnification factor is kept small, for example, less than around 10, using a simple singlet lens as the focusing lens 905, the collimated beam of light can readily focused down to a spot smaller than that of the beam of light received by the WDM 90 at location 901. The ability to focus the beam of light down to such a small size permits placing a small area semiconductor detector at a focal point 906 of the focusing lens 905 for efficient photo detection.

A dichroic filter 903, oriented at a slanted angle, may be inserted into the optical path in between the collimating optical element 902 and the focusing lens 905. The dichroic filter 903 may pass the color band of interest and reflects the remaining colors in the beam of light for further processing within the WDM 90. An optional band pass filter 904 may be inserted following the dichroic filter 903 to further improve the color isolation capability of the WDM 90.

Light reflected from the dichroic filter 903 may impinge upon a second optical element 907, such as a concave mirror. The concave mirror 907 may a radius of curvature approximately equal to the distance between the collimating optical element 902 and the image near focusing lens 905. The concave mirror 907 therefore creates a second image of the collimating lens 902 near a second focusing lens 908. The light beam between the concave mirror 907 and the second image at the lens 908 may have substantially the same diameter as the beam of light between the collimating lens 902 and the first image near the focusing lens 905. The relay imaging concave mirror 907 therefore effectively doubles the collimated beam path without expanding the beam's diameter. Again, the extended yet collimated beam can be easily focused down to a spot smaller than that of the light source at 901. The diameter of the spot may be smaller than 1 mm, for example, around 600 μm, A second dichroic filter 909 may then be inserted in between the relay imaging concave mirror 907 and the second image near focusing lens 908. The second dichroic filter 909 may pass another band of color in the beam of light received by the WDM 90 at location 901 and reflect the remainder of the impinging beam of light for further processing. The first and second dichroic filters 903 and 909 may be inserted approximately midway between the collimating optical element 902 and the focusing lens 905 and between the relay imaging concave mirror 907 and the second image near focusing lens 908, respectively.

As shown in FIG. 25, additional relay collimating optical elements 910, 911, 912, 913 and dichroic filters 914, 915, 916, 917 can be cascaded in the same way to produce multiple images near focusing lenses 918, 919, 920 and 921, each of these images corresponding to a specific color band of light received by the WDM 90 at location 901. As shown in FIG. 25, due to the present disclosure's 1:1 imaging relay architecture, the spots of light produced by focusing lenses 905, 908, 918, 919, 920 and 921 are all smaller than the source of the beam of light, and therefore can be easily captured by small area APD's.

Although FIG. 25 illustrates a 6-port wavelength division multiplexer for a beam of light from the extended light source, it is readily apparent to those skilled in the art that WDM's having different numbers of ports can be easily built in accordance with some embodiments of the present disclosure. It is also apparent to those skilled in the art that although the WDM 90 may use achromatic doublets as the first collimating optical element, singlet lens can also be used since the images created before the focusing lenses 905, 908, 918, 919, 920 and 921 are all nearly monochromatic. Instead of using concave mirrors for relaying the beam of light reflected from the dichroic filters, one may also use refractive optics, such as a convex lens, as a relay element to extend the path of the collimated beam of light. One of the advantages of the zig-zag architecture used in the WDM 90, however, is the possibility for using array detectors, which would lead to a more compact WDM suitable for portable instrumentation.

FIG. 25A illustrates a top view of a light detection assembly 937 with the WDM 90 illustrated in FIG. 25 in accordance with some embodiments of the present disclosure. The light detection assembly 937 may include the WDM 90 and a photodetector system 938. A beam of light which emits from the facet of the optical fiber 852 may be processed by the WDM 90 and detected by the photodetector system 938. The concave mirrors 907, 910, 911, 912, and 913 and the dichroic filters 903, 909, 914, 915, 916, and 917 may be formed on two sides of a reference block 935. The reference block 935 may be made of glass or any material which allows light to pass through it. Accordingly, a zig-zag optical pattern, as illustrated in FIG. 25 may be formed among the collimating optical element 902, the dichroic filters 903, 909, 914, 915, 916, and 917, the reference block 935, the concave mirrors 907, 910, 911, 912, and 913, and the focusing lens 905, 908, 918, 919, 920, and 921. After being processed by the WDM 90, the beam of light emitting from the facet of the optical fiber 852 may split into multiple colored bands with different wavelengths to be detected by photodetectors 940, 941, 942, 943, 944, and 945, respectively. The photodetector can be, but is not limited to, a semiconductor detector, an avalanche photodetector (APD), and a carbon nanotube detector.

In some embodiments, the concave mirrors 907, 910, 911, 912, and 913 may be structurally formed on a relaying assembly 939. It should be understood by those having skill in the art that the concave mirror can be replaced with a convex lens, which is also able to converge and relay the beam of light.

In some embodiments, the dichroic filter can be replaced with a mirror to prevent the beam of light from entering a photodetector when a user wants to decrease the number of light signal channels to be detected. It should be understood by those having skill in the art that the dichroic filter can also be replaced by a dichroic mirror, a beam splitter, or any optical element which is able to split or filter a beam of light.

FIG. 25B illustrates a front view of the light detection assembly 937 with the WDM 90 illustrated in FIGS. 25 and 25A in accordance with some embodiments of the present disclosure. The light detection assembly 937 may have a top cover 940 which is openable. Therefore, the user can open the top cover 940 to change the dichroic mirrors 903, 909, 914, 915, 916 and 917 and modify the light detection system 938 or the WDM 90 inside.

FIG. 26 illustrates an optical ray trace for a prior art collimating device. The technique depicted in FIG. 26 is extensively used in conventional multicolor fluorescence instruments, for example, in U.S. Pat. No. 6,683,314. As shown in FIG. 26, the beam of light diverges rapidly beyond the image 924 created by the collimating optical element 923. Consequently, the only option for constructing a multicolor device is to insert dichroic filters in between the collimating element 923 and its image 924.

Due to the constraint of etendue conservation, the diameter of the collimated beam must be significantly expanded to accept multiple dichroic filters in the section. The expanded beam creates serious challenge to refocusing the collimated beam down to small spots suitable for small area semiconductor detectors. To overcome these difficulties, some instrument manufacturers have chosen to use PMT exclusively for fluorescence detection such as in the main stream flow cytometers manufactured by Becton-Dickinson, Beckman Coulter and Partec's and the MegaBACE series of DNA sequencers by GE Amersham. Other instruments, such as the Luminex multiplexed bead analyzers, have selected certain color bands with known bright fluorescence, and uses large area APD for detecting light in the selected color bands.

FIG. 27 illustrates a perspective view of an alternative embodiment for a 6-port WDM 90 using a combination of zig-zag and branched configurations. The design is a modification of zig-zag configuration depicted in FIG. 25. In the alternative embodiment depicted in FIG. 27, band pass filter 904 of FIG. 25 may be replaced by a dichroic filter 904'. The filter 904' is positioned to let one color pass through and reflects other colors at ninety degrees (90°). The optical path length of the beam of light passing through the dichroic filter 904' and that being reflected from the 904' are substantially the same, such that one arm is focused by lenses 905 and the other by lens 905' to small spots compatible with small area semiconductor detectors placed at focal location 906 and 906'. As shown in FIG. 25, the remaining color of the light reflected by dichroic filter 903 is relay imaged by a concave mirror 907 and the configuration including optical elements 903, 904', 905 and 905' is cascaded two (2) more times to form a 6 port-WDM.

FIG. 28 illustrates a perspective view of an alternative embodiment for a 8-port WDM 90. By replacing the concave mirrors 907 and 910 in FIG. 27 with concave shaped dichroic filters 907' and 910', the WDM depicted in FIG. 28 may provide 2 more color bands in comparison with the WDMs depicted in FIGS. 25 and 27.

Numerous fluorescence probes for use in flow cytometry have been developed over the years. More recently, multiple fluorescence proteins have also become an important tool in biomedical studies. To accommodate different types of fluorescence probe, various techniques have been developed to enable user selection of dichroic filters suitable for their particular needs. A significant challenge for replaceable dichroic filters is avoiding direct contact of the coated filter surface with any hard flow cytometer reference frame. Repeated direct contact between the coated filter surface and any hard reference frame may damage a replaceable dichroic filter. Presently, most conventional solutions addressing this problem use precision-machined mechanical spacers for holding replaceable dichroic filters in place. One example of such a solution appears in U.S. Pat. No. 6,683,314. However, such a solution becomes unreliable if the detector's active area is smaller than 1.0 mm$^2$.

FIGS. 29A and 29B depict fabricating a replaceable dichroic filter assembly 934 illustrated in FIG. 29C suitable for small area detectors. Assembly of the replaceable dichroic filter assembly 934 begins in FIG. 29A which depicts constructing a reference template for its fabrication. The reference template may be a staircase made of two (2) optically parallel glass plates 925 and 926. Bonding the two (2) glass plates 925 and 926 together in optical contact can ensure that a surface 929 of the glass plate 925 becomes optically parallel to a surface 930 of the glass plate 926. A front surface 932 of a replaceable dichroic filter 927 may then be pressed against the surface 929 of the template. A filter holder 928, which loosely fits the dichroic filter 927, may include a reference surface 931 and a filter slot 933. During assembly of the replaceable dichroic filter, the filter slot 933 may be partially filled with epoxy adhesive and the reference surface 931 of the filter holder 928 may be pressed against the surface 930 of the template while filter holder 928 slides toward the dichroic filter 927. While the epoxy adhesive sets, part of the dichroic filter 927 remains seated within the filter slot 933 while pressure is applied against the dichroic filter 927 and filter holder 928. It should be apparent to those skilled in the art that the epoxy adhesive may be either UV or thermally curable, or made by blending together components of an AB mixture. FIG. 29C depicts a dichroic filter fabricated as depicted in FIGS. 29A and 29B and described above. The assembly process depicted in FIGS. 29A and 29B and described above can ensure that the front surface 932 of the replaceable dichroic filter assembly 934 can be optically parallel to the reference surface 931, and indented with respect to the latter at a spacing accurately determined by the thickness of the glass plate 925. The dichroic filter 927 depicted in FIGS. 29A, 29B, and 29C may be the dichroic filters 903, 909, 914, 915, 916, or 917 used with the WDM illustrated in FIG. 25 or the dichroic filter 903 or the filter 904' used with the WDM illustrated in FIG. 27.

FIGS. 30A and 30B depict an embodiment of the present disclosure where the fore-mentioned replaceable dichroic filter assembly 934 is used in the WDM 90 for optically processing a beam of light from an extended light source. A notable feature of the WDM 90 is a glass reference block 935 having an optically flat surface. As will be apparent to those skilled in the art, the glass reference block 935 may be made of other materials. As shown in FIG. 30B, when installing a dichroic filter 927 the reference surface 931 of the replaceable dichroic filter assembly 934 may slide against the flat surface of the glass reference block 935 and be kept in contact therewith by a spring loaded screw 936. Consequently, the coated front surface 932 of the replaceable dichroic filter assembly 934 can remain optically parallel to the optical flat and accurately located. In the meantime, the indentation of front surface 932 with respect to the reference surface 931 may protect it from in physical contact with any object during filter replacement. It is apparent to those skilled in the art that many modifications and variations of the described embodiments of the replaceable dichroic filter assembly 934 are possible. For example, an alternative embodiment of the present disclosure may be a pedestal assembled using a first and a second round optical flat. When assembling the replaceable dichroic filter assembly 934, the reference surface of a filter holder may rest against a surface of the first optical flat and the coated surface of the dichroic filter may rest against the flat surface of the second optical flat. Epoxy bonding then may hold the coated surface of the dichroic filter optically parallel to the reference surface of a filter holder, yet indented at a distance accurately determined by the thickness of the second optical flat.

Optical System with Single Light Source 41

FIG. 31 is a diagram schematically illustrating an optical system with a single light source 41 in accordance with some embodiments of the present disclosure. The optical system with a single light source 41 may include a LD based optical subsystem 50, a composite microscope objective 60, a WDM 90, and a light detection system 938. The beam of light may propagate substantially along the z axis and enter the composite microscope objective 60 from the LD based optical subsystem 50 to illuminate particles present within the viewing zone inside the composite microscope objective 60. The light scattered from and fluoresced by particles may then be reflected by the concave mirror 601, corrected by the corrector plate 602, and collected by the optical fiber 852 substantially along the x axis. The optical fiber 852 may be fixed by a fiber holder 940.

Common wavelengths of light sources may include, but not limited to, 375 nm, 405 nm, 440 nm, 488 nm, 502 nm, 534 nm, 561 nm, 591 nm, 637 nm, and 637 nm. The light detection system 938 may be coupled with circuits for processing light signals. The more ports the WDM 90 has, the more light signal channels the user can use.

Optical System with Multiple Light Sources 42

FIG. 32 is a diagram schematically illustrating an optical system with multiple light sources 42 in accordance with some embodiments of the present disclosure. The optical system with multiple light sources 42 may include multiple LD based optical subsystems 50, multiple WDMs 90, multiple light detection systems 938, and a composite microscope objective 60 with a viewing zone. The number of WDMs 90 may correspond to the number of LD based optical subsystems 50. In FIG. 32, the optical system with multiple light sources 42 includes three laser diodes 501 for emitting multiple beams of light with different wavelengths, three collimating lenses 502 in front of the three LDs for collimating the beams of light respectively, three dichroic filters 506, 507, and 508 for passing beams of light with certain wavelength range or reflecting beams of light with certain wavelength range, a plano-convex lens 504 for shaping the beams of light on the major axis, a cylindrical lens 505 for focusing the beams of light onto three spatially separated locations in the flow channel 604, a composite microscope objective 60 for directing the light scattered from and fluoresced by the illuminated particles at three spatially separated locations to be collected by three optical fibers 852, respectively, three optical fibers 852 for collecting scatter and fluorescence emissions and transmitting the emissions to three WDMs 90, respectively, and three WDMs 90 and light detection systems 938 for processing and detecting the scatter and fluorescence light, respectively. The direction of beams of light entering the composite microscope objective 60 may be perpendicular to the direction of scatter and fluoresce emissions to be collected by the optical fiber 852. It should be noted that the plano-convex lens 504 and the cylindrical lens 505 can be replaced with any conventional beam shaper and any focusing lens. It should also be noted that the various aspects of the present disclosure are not limited to specific numbers of laser diodes, collimating lenses, dichroic filters, plano-convex lenses, composite microscope objectives, optical fibers, WDMs, and light detection systems and specific wavelength and direction of each beam of light.

FIG. 33 illustrates an enlarged view of beams of light 509 and 510 shown in FIG. 32. The beams of light 509 and 510 are emitted from different laser diodes 501 with different wavelengths and then are focused onto spatially divided locations in the flow channel 604 inside the composite microscope objective 60.

Optical System with Chromatic Compensation Elements 51

FIG. 34 is a diagram schematically illustrating an optical system with chromatic compensation elements 51 in accordance with one aspect of the present disclosure in accordance with some embodiments of the present disclosure. The optical system with chromatic compensation elements 51 may include the optical system with multiple light sources 42, as shown in FIG. 32, and multiple chromatic compensation elements 514, 515, and 516. Each of the chromatic compensation elements 514, 515, and 516 may be positioned on the beam paths of beams of light emitting from light sources 511, 512, and 513, respectively, and compensate chromatic aberration in the viewing zone. As such, the beams of light emitting from the light sources 511, 512, and 513 with different wavelengths may be focused onto three spatially divided locations on a common plane which is in the viewing zone and substantially parallel to the direction of a sample flow. The optical properties of chromatic compensation elements 514, 515, and 516 may be different from each other. For example, their thicknesses and shapes may be different to accommodate various beams of light with different wavelengths.

In some embodiments, the optical system shown in FIG. 34 may only need one or two chromatic compensation elements to compensate chromatic aberration in the viewing zone. It should be noted that the various aspects of the present disclosure are not limited to specific numbers or optical properties of chromatic compensation elements.

Power Monitoring System 43

FIG. 35 is a diagram schematically illustrating a power monitoring system 43 in accordance with some embodiments of the present disclosure. The power monitoring system 43 may include a first light source 513 for emitting a first beam of light, a second light source 512 for emitting a second beam of light, a first dichroic filter 519 for reflecting the first beam of light and passing the second beam of light, a second dichroic filter 518 for reflecting the second beam of light, a first detector 401 for measuring residual power of the first and second beams of light downstream of the first dichroic filter 519 on a time-division multiplexing basis, and a control unit 522 coupled with the first detector 401, the first light source 513, and the second light source 512. The first detector 401 may be positioned near or coupled to the first dichroic filter 519. The first and second light sources 513 and 512 may emit beams of light with different wavelengths.

In order to reduce interference between the residual power of the first and second beams of light, the first detector 401 may measure the residual power of the first beam of light when the second light source 512 is off or measure the residual power of the second beam of light when the first light source 513 is off. The residual power of the first and second beams of light may include power of the first beam of light passing through the first dichroic filter 519 and power of the second beam of light reflected by the first dichroic filter 519.

In some embodiments, the control unit 522 may include a feedback circuit to increase the power of the light source when residual power of the light source drops below a certain level or to lower the power of the light source when the residual power of the light source increases above a certain level.

In some embodiments, a second detector 400 may be applied with the power monitoring system 43 and positioned near or coupled to the second dichroic filter 518 to measure the residual power of the second beam of light downstream of the second dichroic filter 518. The residual power of the second beam of light downstream of the second dichroic filter 518 may include power of the second beam of light passing through the second dichroic filter 518. The second detector 400 may also be coupled to the control circuit 522. When the second detector 400 is applied to the power monitoring system 43, the first detector 401 may only need to monitor the residual power of the first beam of light.

In some embodiments, a third light source 511 for emitting a third beam of light and a third dichroic filter 517 for reflecting the third light may be also applied with the power monitoring system 43. The third light source 511 may be also coupled to the control circuit 522. As such, the first detector 401 may measure residual power of the first, second, and third beams of light downstream of the first dichroic filter 519 on a time-division multiplexing basis.

In some embodiments, the second detector 400 may measure residual power of the second and third beams of light downstream of the second dichroic filter 518 on a time-division multiplexing basis. The residual power of the second and third beams of light downstream of the second dichroic filter 518 may include power of the second beam of light passing through the second dichroic filter 518 and power of the third beam of light reflected by the second dichroic filter 518.

In some embodiments, a third detector (not shown in FIG. 35) may also be applied with the power monitoring system 43 and positioned near or coupled to the third dichroic filter 517 to measure residual power of the third beam of light downstream of the third dichroic filter 517. The third detector may be also coupled to the control circuit 522. The residual power of the third beam of light at the downstream of the third dichroic filter 517 may include power of the third beam of light passing through the third dichroic filter 517.

The second beam of light can either be detected by the first detector 401 or the second detector 400. The third beam of light can be detected by the first detector 401, the second detector 400, or the third detector which is positioned near or coupled to the third dichroic filter 517. The control circuit 522 may control the operation of the detectors and light sources.

It should be understood by those having skill in the art that the dichroic filter can also be replaced by a dichroic mirror or a beam splitter. It should also be noted that the various aspects of the present disclosure are not limited to specific numbers of light sources, dichroic filters, and detectors.

Optical System 44

FIG. 36 is a diagram schematically illustrating an optical system 44 in accordance with some embodiments of the present disclosure. The optical system 44 may include a composite microscope objective 60, as shown in FIG. 8, a light source 403, and a beam splitter 402. The light source 403 may emit beams of light to illuminate objects in a viewing zone, which is located in a flow channel 604 inside a cuvette 603. The composite microscope objective 60 may image light scattered from and fluoresced by the objects in the viewing zone at an image plane 404 external to the composite microscope objective 60. The light source 403 and the image plane 404 may be located on two sides of the beam splitter 402.

The composite microscope objective 60 may include a concave mirror 601 and an aberration corrector plate 602 coupled to the two sides of the cuvette 603. The aberration corrector plate 602 may be an aspheric lens that has a first zone with negative optical power and a second zone with positive optical power radially inside the first zone. A neutral zone may be the thinnest portion of the aberration corrector plate 602 and located between the first zone and the second zone. The aspheric lens may be a plano-aspherical lens. The concave mirror may be a plano-concave back surface mirror or a front surface mirror. The concave mirror 604 and the aberration corrector plate 602 may be made of an optically transparent material.

In FIG. 36, the beam of light emitting from the light source 403 may be reflected by the beam splitter 402 and enter into the composite microscope objective 60 to illuminate objects in the viewing zone. The light scattered from and fluoresced by objects may be reflected by the concave mirror 604, transmit through the aberration corrector plate 602 and the beam splitter 402, and form an image at the image plane 404 external to the composite microscope objective 60. The light source 403 may include multiple laser diodes 403a, 403b, and 403c emitting multiple beams of light with different wavelengths to illuminate objects at multiple locations in the flow channel 604. Accordingly, multiple images 404a, 404b, 404c may be formed at the image plane 404.

In some embodiments, the locations of the light source 403 and the image plane 404 may be swapped. Accordingly, the beam of light emitting from the light source 403 may transmit through the beam splitter 402 and enter into the composite microscope objective 60 to illuminate objects in the viewing zone. The light scattered from and fluoresced by objects may be reflected by the concave mirror 604, transmit through the aberration corrector plate 602, be reflected by the beam splitter 402, and form an image at the image plane 404 external to the composite microscope objective 60.

In some embodiments, the viewing zone may be located in a jet stream or a surface of a substrate containing objects (not shown in FIG. 36). The objects may be delivered into the viewing zone by a fluidic system, such as a fluidic system shown in FIG. 14 or 15.

In some embodiments, the scattered and fluoresced light imaged at the image plane 404 may be received by a fiber (not shown in FIG. 36) which transmits the light to a photodetector. The scattered and fluoresced light may be processed by a wavelength division multiplexer (WDM) (not shown in FIG. 36) before being detected by the photodetector. The WDM may be configured as a WDM illustrated in FIGS. 25, 25A, and 25B. The photodetector can be, but not limited to, a semiconductor photodetector, a multipixel photon counter, and a carbon nanotube detector.

In some embodiments, the light source 403 may emit coherent light or incoherent light. The light source 403 can be single or multiple laser diodes, light emitting diodes, illumination devices emitting beam of light, or any combination of them.

In some embodiments, a chromatic compensating lens (not shown in the figure) may be inserted between the aberration corrector place 602 and the image plane 404 to serve to reduce the residual chromatic aberration.

Axial Light Loss Detection System 45

FIG. 37 is a diagram schematically illustrating an axial light loss detection system 45 in accordance with some embodiments of the present disclosure. The axial light loss detection system 45 may include a concave mirror 406 for reflecting light that propagates from a viewing zone and a detector 408 for measuring axial light loss produced by the object in the viewing zone by detecting light reflected by the concave mirror 406. The light reflected by the concave mirror 406 may include forward scattered light (FSC) and remaining light of beam of light entering into the viewing zone from a light source 412 to irradiate the object therein, which is so called axial light loss (ALL). The axial light loss of the beam of light along its propagation direction may result from the object passing through the beam of light. The beam of light may be blocked or absorbed by the object.

The axial light loss detection system 45 may utilize the concave mirror 406 to direct both FSC and remaining light into the detector 408 in order to determine the size of object. The FSC and remaining light may have the same wavelength, and therefore the signals of FSC and remaining light detected by the detector 408 may be proportional to square of the sum of their electric fields as follows:

$$(E_{FSC}+E_{ALL})^2 \tag{8}$$

$E_{FSC}$ represents the electric field of FSC. $E_{ALL}$ represents the electric field of remaining light.

On the contrary, a conventional ALL detection system disclosed in prior art usually requires a pinhole positioned along a laser beam path to block FSC in order to detect remaining light of the laser beam. Accordingly, the signals of remaining light detected by an ALL detector is proportional to square of its electric field as follows:

$$(E_{ALL})^2 \qquad (9)$$

Further, a conventional FSC detection system disclosed in prior art usually requires a mask positioned along a laser beam path to block remaining light of the laser beam in order to detect FSC. Accordingly, the light signals of FSC detected by a FSC detector is proportional to square of its electric field as follows:

$$(E_{FSC})^2 \qquad (10)$$

Apparently, neither of the conventional ALL detection system nor conventional FSC detection system could operate without using a pinhole or a mask.

In some embodiments, the concave mirror 406 may be an ellipsoidal mirror or a combination of a flat mirror and a lens. The detector 408 may be an axial light loss detector to determine the size of the object.

In some embodiments, the detector 408 may be in a heterodyne mode detecting the coherent interference of FSC and the remaining light. The wavelengths of FSC and remaining light may be the same.

In some embodiments, a light source 412 emitting beam of light may be used to illuminate the object in the viewing zone. The optical axis of the beam of light is substantially perpendicular to the flow direction of the object.

In some embodiments, multiple light sources 412 emitting beams of light with different wavelengths may be used to illuminate the objects in the viewing zone. When multiple light sources 412 are applied to the axial light loss detection system 45, a filter 407 may be positioned upstream of the detector 408 to separate the light irradiated by the first light source and reflected by the concave mirror 406 and the light irradiated by the second light source and reflected by the concave mirror 406. As such, the detector 408 may measure them separately, for example, on a time-division multiplexing basis.

In some embodiments, the viewing zone may be located within a microscope objective 410. The viewing zone may be located in a flow channel 409, a jet stream, or a substrate. In some embodiments, a cylindrical lens 411 may be coupled to the microscope objective 410 to focus beams of light emitting from the light source 412 to the viewing zone. The optical axis of the cylindrical lens 411 is substantially perpendicular to the optical axis of the light reflected by the concave mirror 406.

FIG. 38 is a diagram schematically illustrating an axial light loss detection system 45 coupled with a second light detection system 413 in accordance with some embodiments of the present disclosure. The axial light loss detection system 45 may utilize a composite microscope objective 60, as illustrated in FIG. 8 The composite microscope objective 60 may include a second concave mirror 415 and an aberration corrector plate 414 located on two sides of the viewing zone of the composite microscope objective 60. The optical axes of the second concave mirror 415 and the aberration corrector plate 414 are substantially parallel to the optical axis of the light reflected by the concave mirror 406. The FSC and remaining light propagating from the viewing zone may be reflected by the concave mirror 406 and detected by the detector 408 while the side-scattered fluoresced light may be reflected by the second concave mirror 415, propagate out of the composite microscope objective 60 via the aberration corrector plate 414, and be detected by the second light detection system 413.

In some embodiments, one or more control circuits may be coupled with one or more of the detector 408, the second light detection system 413, and the light source 412 to process detected light signals. As known by one skilled in the art, the control circuit may include an amplifier to amplify detected light signals, a noise filter to reduce noise interference, and a processor to process detected light signals and generate corresponding information regarding the properties of the object.

Alternative Combined Microscope Objective

FIGS. 11, 12 and 13 illustrate the build-up of a composite microscope objective 60 adapted for imaging light scattered from and fluoresced by an object present within a viewing zone. The illustrated composite microscope objective comprises a viewing zone, a concave mirror arrangement 601, 610, 617, an exit area and an illumination beam forming arrangement 505, as illustrated in FIG. 8A. It should be noted that in FIGS. 11, 12 and 13 the beam forming arrangement is not illustrated. The viewing zone in FIG. 11 may be located in e.g. a channel 604 of a cuvette 603. In FIG. 12, the viewing zone may be located e.g. along the droplets of the jet stream 519 leaving the nozzle 518. In FIG. 13, the viewing zone maybe located e.g. in the plane of the substrate. The exit area of the microscope objective is an area through which scattered light and fluoresced light impinging from an object present in the viewing zone passes, which scattered and fluorescent light is reflected by the concave mirror of the microscope objective. The aberration corrector plate 602 in FIG. 11, 612 in FIGS. 12 and 618 in FIG. 13 may be located in the exit area. It should be noted that the corrector plate may be used, in particular in combination with a spherical mirror 601, 610, 617. However the corrector plate may be omitted when using a concave mirror having already implemented a correcting shape. Thus, the exit area does not have to include a corrector, if a concave mirror has an appropriate shape and the gain of the corrector plate is not required. As can be seen in FIGS. 11, 12 and 13, the viewing zone is arranged between the concave mirror arrangement and the exit area. The concave mirror 601, 610, 617 is arranged to reflect scattered and fluoresced light impinging from an object present in the viewing zone to the exit area. The illumination beam forming arrangement 505 is illustrated e.g. in FIG. 8A. FIG. 8A illustrates an arrangement of FIG. 11 having attached illumination beam arrangement 505 to the cuvette 603. The illumination beam arrangement 505 is arranged so that an illumination beam entering the illumination beam forming arrangement is pre-definitely formed at the viewing zone. A path of an illumination beam from an illumination system can be seen e.g. in FIG. 1 or 3A. FIGS. 11, 12 and 13 as well as FIG. 8A illustrate that the concave mirror arrangement, the viewing zone and the exit area are arranged along a first axis, also referred to as x-axis. FIG. 9A illustrated that an optical image of the viewing zone, e.g. within channel 604 in FIG. 9A is formed outside the composite microscope objective in the image plane 605 with image locations 606, 607 and 608. The illumination beam forming arrangement 505 is arranged so that an illumination beam impinges the viewing zone along a second axis, also referred to as z-axis, which is substantially perpendicular to said x-axis. The above described cuvette 603 may be manufactured of an optical transparent material, wherein the viewing zone is formed in the cuvette, in particular in the channel 604 of the cuvette 603. The channel extends along a third axis, also referred to as y-axis being substantially perpendicular to the x-axis and the z-axis, so that a liquid flow in the channel flows along the y-axis, as illustrated e.g. in FIG. 5D, wherein the viewing zone is located within the channel. FIGS. 8 and 8A illustrated that the cuvette 603 may be of rectangular cross section in a plane of the first axis/x-axis and second axis/z-axis. It should be noted that the cross section of the cuvette 603 may also be of a form, that a sheath flow covering the sample flow forces the sample flow into a rectangular cross section. The cross section of the channel 604 may be constant along the y-axis, but may also vary along the y-axis. In particular the channel may have a focused cross section in the area of the viewing zone. The viewing area may include a plurality of predefined viewing points distributed along the y-axis for different illumination wavelengths, as can be seen in FIG. 33, or along the z-axis, which may be a varying focal point varying along the z-axis, when adjusting the objective 60 with respect to the illumination system 50, as will described later. Although element 505 may be allocated to the illumination system 50, element 505 may also be part of the objective 60, in particular it may be attached to the cuvette 603. The illumination beam forming arrangement 505 is adapted to compress an illumination beam, so that the illumination beam in the viewing zone has a compressed dimension along the y-axis. The illumination beam forming arrangement 505 may be a cylindrical lens, in particular having a cylindrical axis parallel to the x-axis, as can be seen in FIGS. 5D and 5E. It should be noted that the illumination beam forming arrangement can be assembled by a plurality of optical elements, so that the arrangement 505 may not have a defined axis. The aberration corrector arrangement 602, 612, 618 may be arranged in the exit area, as can be seen in FIGS. 11, 12 and 13. The aberration corrector arrangement may be an aspheric lens made of optically transparent material. As can be seen in FIG. 9A, said aberration corrector arrangement may have a first zone with negative optical power, a second zone radially inside the first zone with positive optical power, and a neutral zone between the first zone and the second zone. The neutral zone in FIG. 9A is thinner than each of the first zone and the second zone, so that light reflected from the concave mirror arrangement passing through said aberration corrector arrangement forms a focal area. Although FIG. 9A illustrates a corrector plate with convex and concave portions, it should be noted that the positive and negative optical power may be achieved by using different optical materials at different locations of the corrector plate. The concave mirror arrangement 601, the viewing zone and the aberration corrector arrangement 602 form a reversed Schmidt camera. The concave mirror arrangement may be formed by plane-convex lens, as can be seen in FIG. 11. The concave mirror may be a plano-concave back surface mirror. The plano-concave back surface mirror may be made from an optically transparent material. As can be seen in FIG. 8A a plano-surface of said plano-concave back surface mirror is optically coupled to a flat surface of said cuvette. Plano-concave back surface mirror means that although the optical lens body is a plano-convex lens body, the surface when seeing into the mirror, which is the inside of the optic body, is concave. The plano-surface of said plano-concave back surface mirror may also be optically coupled to said flat, transparent substrate, as can be seen in FIG. 13. Said concave mirror may also be a front surface mirror, as can be seen from FIG. 12. It should be noted that the mirror of FIG. 12 can also be used in combination with a cuvette, and the mirror of FIG. 11 can also be used for a jet stream. The concave mirror arrangement, the aberration corrector arrangement and the illumination beam forming arrangement may be attached to the cuvette by at least one of index matching gel, index matching fluid, optical adhesive material and optical contact bonding. It should be noted that also a combination may be used for attaching.

As can be seen in FIG. 1, 3A, 31, 32 or 34-38, the composite microscope objective 60 may be combined with or comprise an illumination system. Although not mandatory, the illumination may be an illumination system as described above, in particular with a laser source 501, an collimating optical arrangement 502 to form a collimated laser beam and a beam shaping arrangement 504, 505 being adapted to shape a collimated beam, wherein the beam shaping arrangement includes the illumination beam forming arrangement 505. The laser source may be a laser diode and the collimating arrangement may be arranged with respect to the laser diode so as to form a collimated beam. As an alternative, the laser source may be a conventional laser with an optic arrangement to form a collimated beam of a desired cross section. The laser diode and the collimation optical arrangement, or alternatively the conventional laser with the optics are adapted to form a beam having an elliptical cross section having a major axis and a minor axis, wherein the minor axis is oriented substantially along the y-axis and the major axis is oriented substantially along the x-axis, as can be seen in FIG. 5E. The beam shaping arrangement may include a major axis optical beam compressing arrangement 504 being adapted to compress at least the major axis of the collimated elliptical beam. The illumination beam forming arrangement 505 is adapted to compress at least the minor axis of the collimated elliptical beam. This can be seen for example in FIG. 1, 3A or 6.

The viewing zone may be movable along the z-axis with respect to the illumination system so as to vary a focus of the compressed elliptical beam within the viewing zone along the z-axis. This allows a scanning along the z-axis. In particular this allows to sense or scan properties of a cell in the viewing zone at different locations. It should be understood, that either the objective 60 may be controllably moved or the illumination system 50 or both. It should also be understood that the variation of the focus may also be achieved by moving single components of the illumination system, e.g. one of the mirrors 523*b*, 523*a* or the element 504, as illustrated in FIG. 7. Also single components of the objective may be moved to vary the focus along the z-axis. The actuation can be conducted by e.g. piezo actuators or acoustic actuators. In particular the varying focus can be achieved by a modulation or an sinusoidal oscillation of the respective component. Thus the cuvette is movable with respect to the laser source so as to spatially vary a focus of the laser source in the channel. For this purpose, a control unit can be provided being adapted to control the movement of components of the composite microscope objective along the z-axis so as to spatially vary a focus of the laser source in the channel. It should be noted that likewise also a variation of the focus can be achieved along the y-axis or even the x-axis.

Combined Wavelength Division Multiplexer (WDM) with Semiconductor Photo Detector FIGS. 25, 27, and 28 illustrate a wavelength division multiplexer (WDM) for separating light emitted from a light source into multiple colored bands. The wavelength division multiplexer may comprise an imaging optical arrangement 902, a dichroic filter arrangement 903, 904, a semiconductor photo detector 906 and a focusing optical arrangement 905. The imaging optical arrangement 902 forms a beam of light from the light emitted from a light source 901 and produces an image of substantially the same size as the effective size of said imaging optical arrangement. The light source may be an outlet of an optical fiber, which fiber may transfer detected light from the microscope objective 60 to the WDM. The dichroic filter arrangement 903, 904 may be located between said imaging optical arrangement 902 and said image, and separates the beam of light into a first branch and a second branch of distinctive colors. As can be seen in FIG. 25, the first branch travels toward element 905, whereas the second branch travels toward element 907. The semiconductor photo detector 906 is located in the first branch behind the focusing optical arrangement 905, which is located between the dichroic filter arrangement 903, 904 and the semiconductor photo detector 906 so as to focus the beam of light onto the semiconductor photo detector. Light means an electromagnetic wave, coherent or non-coherent, particularly having a wavelength which transits the used optical elements. In particular, the term light is not limited to the visible part of light, e.g., light between 380 nm and 780 nm. It should be noted that also infrared light and ultraviolet light may be used, if the used optical components are capable of being operated with such wavelengths. The focusing optical element arrangement 905 is located in or in proximity to an image plane of said image. It should be noted that the imaging arrangement 902 as well as the focusing arrangement 905 may be composed of more than one optical element. In particular, a plurality of lenses may be combined so as to form the imaging arrangement 902 or the focusing arrangement 905. Likewise the dichotic filters may be composed of more than one filter or optic element. In particular to compose particular properties of the respective arrangements. The focusing optical arrangement and the semiconductor photo sensor may be arranged to each other that the beam of light is focused to a spot having a diameter of less than 1.0 mm, particularly of less than 0.6 mm. In particular when using semiconductor sensors the signal to noise ration SNR can be significantly reduced. As can be seen in FIG. 25, the wavelength division multiplexer as described above may further comprise an image relay optical arrangement 907. This image relay optical arrangement may be located in or in proximity to an image plane produced by said imaging optical arrangement in the second branch, wherein said image relay optical arrangement is adapted to produce an image of said imaging optical arrangement in a third branch having substantially the same size as the image in the second branch. The third branch in FIG. 25 is the beam traveling from the element 907 toward element 909. The effective size of the optical element is the area where beams from the object transit the optical element. Consequently, producing an image of substantially the same size as the effective size of said optical element means that between the optical element and the image the beam is within a virtual parallel tube. For illustration purposes, in the hypothetical case the object is a pinhole the optical element produces a collimated beam. The image relay optical arrangement 907 may be a concave mirror. Alternatively the image relay optical arrangement 907 may be a combination of a lens and a mirror, in particular a plane mirror. The wavelength division multiplexer as described above may further comprise an additional dichroic filter arrangement 909, wherein the additional dichroic filter arrangement is located between said image relay optical arrangement 907 and an image produced by said image relay optical arrangement 907. Said additional dichroic filter arrangement 909 from the third branch produces a fourth branch and a fifth branch of the beam of light having distinctive colors. The fourth branch in FIG. 25 is the beam traveling from the dichroic filter 909 toward the focusing element 908, whereas the fifth branch is the beam traveling from the dichroic filter toward the element 910. The above described wavelength division multiplexer further may comprise an additional focusing optical arrangement 908 and an additional semiconductor photo detector, wherein the additional focusing optical arrangement 908 is located in the fourth branch and focuses the beam of light in the fourth branch so as to focus the beam of light onto the additional semiconductor photo detector. The wavelength division multiplexer may further comprise a plurality of image relay optical arrangements 910, 911, 912, 913, a plurality of dichroic filter arrangements 914, 915, 916, 917, a plurality of semiconductor photo detectors and a plurality of focusing optical arrangements 918, 919, 920, 921, wherein each of the plurality of focusing optical arrangements is arranged between a respective one of the plurality of dichroic filter arrangements and a respective one of the plurality of semiconductor photo detectors so as to form a cascaded arrangement, as can be seen in FIG. 25. The additional focused spots may have a diameter of less than 1.0 mm, particularly of less than 0.6 mm for multiple colored bands of said beam of light. The plurality of dichroic filter arrangements are arranged in a common plane, as can be seen in FIG. 25A. The wavelength division multiplexer may further comprise a plan-parallel optical basis having a first surface and second surface parallel thereto, wherein the plurality of dichroic filter arrangements are arranged parallel, preferably in abutment to the first surface of the plan-parallel optical basis, as described with respect to the WDM 90. The dichroic filter arrangements are assembled using a template that includes two optically flat glass plates bonded together in optical contact, wherein the dichroic filter arrangements are bonded to a filter holder using the template such that a coated filter surface of the dichroic filter arrangements are indented and optically parallel to a reference surface of the filter holder, as can be seen in FIGS. 29A, B and C. The reference surface of the filter holder rests against an optically flat surface of an reference block included in the wavelength division multiplexer thereby providing consistent optical alignment when installing the dichroic filter arrangements into the wavelength division multiplexer. The respective image relay optical arrangements may be formed into the second surface of the plan-parallel optical basis, as can be seen in FIG. 25A. At least one of the semiconductor photo detectors is an avalanche photo diode detector. As an alternative or in addition, at least one of the semiconductor photo detectors is a carbon nanotube detector.

INDUSTRIAL APPLICABILITY

Although an embodiment of the present disclosure of an LD based optical system for flow cytometric application has been described in some detail, and equally advantageous embodiments have also been described for a stream based flow cytometric instrument, it will be apparent to those of ordinary skill in the art that many modifications and variations of the described embodiment are possible in the light of the above teachings without departing from the principles and concepts of the disclosure as set forth in the claims.

Although an embodiment of the present disclosure of wavelength division multiplexing device for separating light beam from an extended light source into multiple color bands has been described in some detail, and several other equally advantageous embodiments have also been described, it will be apparent to those ordinary skilled in the art that many modifications and variations of the described embodiments are possible in the light of the above teachings without departing from the principles and concepts of the disclosure as set forth in the claims.

Although the present disclosure describes certain exemplary embodiments, it is to be understood that such disclosure is purely illustrative and is not to be interpreted as limiting. Consequently, without departing from the spirit and scope of the disclosure, various alterations, modifications, and/or alternative applications of the disclosure will, no doubt, be suggested to those skilled in the art after having read the preceding disclosure. Accordingly, it is intended that the following claims be interpreted as encompassing all alterations, modifications, or alternative applications as fall within the true spirit and scope of the disclosure.

What is claimed is:

1. A flow cytometer having a laser diode (LD) system, the LD system comprising:
    an LD for emitting a diverging beam of light from an edge thereof, the diverging beam of light having an elliptically-shaped cross-sectional profile with both a major axis and a minor axis;
    a collimating lens configured to convert the diverging beam of light emitted from the LD into a collimated elliptical beam of light, wherein the minor axis of the collimated elliptical beam of light is oriented parallel to a direction in which particles pass through a viewing zone;
    a beam compressing optical element configured to reduce a size of the collimated elliptical beam of light at the viewing zone whereby a width of the collimated elliptical beam of light oriented perpendicular to the direction in which the particles pass through the viewing zone is less than a width of a liquid sheath flow; and
    a cylindrical focusing element positioned adjacent to the viewing zone with an axis of the cylindrical focusing element being oriented perpendicular to the direction in which the particles pass through the viewing zone whereby the minor axis of the elliptical beam of light becomes focused at the viewing zone and the size of the major axis of the elliptical beam of light at the viewing zone remains essentially unchanged.

2. The flow cytometer of claim 1, wherein the beam compressing optical element is configured to reduce the size of both the major axis and the minor axis of the collimated elliptical beam of light.

3. The flow cytometer of claim 1, wherein the beam compressing optical element is a spherical focusing lens.

4. The flow cytometer of claim 1, wherein the beam compressing optical element is a plano-convex lens.

5. The flow cytometer of claim 1, wherein the beam compressing optical element is an achromatic doublet lens.

6. The flow cytometer of claim 1, wherein the beam compressing optical element is one of a combination of spherical lenses, cylindrical lenses, and/or prism pairs.

7. The flow cytometer of claim 1, wherein the beam compressing optical element is a concave mirror.

8. The flow cytometer of claim 1, wherein the LD system further comprises a polarization conditioning element disposed between the collimating lens and the beam compressing optical element through which the collimated elliptical beam of light passes.

9. The flow cytometer of claim 1, wherein the cylindrical focusing element is a cylindrical plano-convex lens.

10. The flow cytometer of claim 1 further having a cuvette, wherein the viewing zone is located within a channel located within the cuvette.

11. The flow cytometer of claim 10, wherein the cylindrical focusing element is attached to the cuvette.

12. The flow cytometer of claim 10, wherein the cylindrical focusing element is optically coupled to an abutting flat surface of the cuvette.

13. The flow cytometer of claim 1, wherein the viewing zone is located in a jet stream formed by sample liquid and the liquid sheath flow.

14. A flow cytometer having a laser diode (LD) system, the LD system comprising:
    an LD for emitting a diverging beam of light from an edge thereof, the diverging beam of light having an elliptically-shaped cross-sectional profile with both a fast axis and a slow axis;
    a collimating lens configured to convert the diverging beam of light emitted from the LD into a collimated elliptical beam of light, wherein the slow axis of the collimated elliptical beam of light is oriented parallel to a direction in which particles pass through a viewing zone;
    a beam compressing optical element configured to reduce the size of both the fast axis and the slow axis of the elliptical beam of light; and
    a cylindrical focusing element positioned adjacent to the viewing zone with an axis of the cylindrical focusing element being oriented perpendicular to the direction in which the particles pass through the viewing zone whereby the slow axis of the elliptical beam of light becomes focused at the viewing zone and the size of the fast axis of the elliptical beam of light at the viewing zone remains essentially unchanged.

15. The flow cytometer of claim 14, wherein the beam compressing optical element is configured to focus the fast axis of the elliptical beam of light at the viewing zone.

16. The flow cytometer of claim 15, wherein the fast axis of the elliptical beam of light is focused at the viewing zone to a size less than a width of a liquid sheath flow.

17. The flow cytometer of claim 16, wherein the cylindrical focusing element is optically coupled to a cuvette, wherein the viewing zone is located within a channel located within the cuvette.

18. The flow cytometer of claim 14, wherein the LD system further comprises a reflecting optical element configured to orient the slow axis of the collimated elliptical beam of light parallel to the direction in which particles pass through the viewing zone.

19. A method for delivering an elliptically shaped beam of light using a laser diode (LD) system, the elliptically shaped beam of light having a smooth profile at a focus of a minor axis thereof that is located at a viewing zone through which a sample liquid flows, the sample liquid being hydrodynamically focused within the viewing zone by a liquid sheath flow that also flows through the viewing zone, the method comprising the steps of:
    providing an LD that emits a diverging beam of light from an edge thereof, the diverging beam of light having an elliptically shaped cross-sectional profile with both a major axis and a minor axis;
    impinging the diverging beam of light emitted by the LD upon a collimating lens to convert the diverging beam of light emitted therefrom into a collimated elliptical beam of light wherein the minor axis of said collimated elliptical beam of light is oriented parallel to a direction in which sample liquid passes through the viewing zone;
    after passing through the collimating lens, impinging the collimated elliptical beam of light upon a beam compressing optical element to reduce a size of the collimated elliptical beam of light at the viewing zone whereby a width of the major axis of the collimated elliptical beam of light oriented perpendicular to the direction in which sample liquid passes through the viewing zone becomes less than a width of said liquid sheath flow; and after passing through the beam compressing optical element, impinging the elliptical beam of light upon a cylindrical focusing element positioned adjacent to the viewing zone with an axis of the cylindrical focusing element being oriented perpendicular to the direction in which sample liquid passes through the viewing zone, whereby the minor axis of the elliptical beam of light becomes focused at the viewing zone and the size of the major axis of the elliptical beam of light at the viewing zone remains essentially unchanged.

20. The method of claim 19, wherein the viewing zone is in a cuvette, wherein the beam compressing optical element is attached to the cuvette.

* * * * *